(12) United States Patent
Grant et al.

(10) Patent No.: US 8,425,471 B2
(45) Date of Patent: Apr. 23, 2013

(54) REAGENT SUPPLY FOR A HEMODIALYSIS SYSTEM

(75) Inventors: Kevin L. Grant, Litchfield, NH (US);
Michael J. Wilt, Windham, NH (US);
Jason A. Demers, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 1200 days.

(21) Appl. No.: 12/199,196

(22) Filed: Aug. 27, 2008

(65) Prior Publication Data
US 2010/0051551 A1 Mar. 4, 2010

Related U.S. Application Data

(63) Continuation-in-part of application No. 12/072,908, filed on Feb. 27, 2008, now Pat. No. 8,246,826, and a continuation-in-part of application No. 12/038,474, filed on Feb. 27, 2008, which is a continuation of application No. 11/871,821, filed on Oct. 12, 2007, now abandoned, application No. 12/199,196, which is a continuation-in-part of application No. 12/038,648, filed on Feb. 27, 2008, now Pat. No. 8,042,563, which is a continuation-in-part of application No. 11/871, 803, filed on Oct. 12, 2007, now Pat. No. 7,967,022, application No. 12/199,196, which is a continuation-in-part of application No. 11/871,793, filed on Oct. 12, 2007, and a continuation-in-part of application No. 11/871,787, filed on Oct. 12, 2007, now abandoned, and a continuation-in-part of application No. 11/871,712, filed on Oct. 12, 2007, and a continuation-in-part of application No. 11/871, 680, filed on Oct. 12, 2007, now Pat. No. 8,273, 049.

(60) Provisional application No. 60/904,024, filed on Feb. 27, 2007, provisional application No. 60/921,314, filed on Apr. 2, 2007, provisional application No. 60/903,582, filed on Feb. 27, 2007.

(51) Int. Cl.
*A61M 5/00* (2006.01)

(52) U.S. Cl.
USPC .............................. 604/258; 604/8; 604/410

(58) Field of Classification Search .................. 604/258, 604/410, 8; 210/198.1, 646
See application file for complete search history.

(56) References Cited

U.S. PATENT DOCUMENTS 1,693,526 A 11/1928 Owens
2,529,028 A 11/1950 Landon
(Continued)

FOREIGN PATENT DOCUMENTS

DE 3 328 744 A1 2/1985
EP 0 687 474 A1 12/1995
(Continued)

OTHER PUBLICATIONS

Written Opinion for Application No. PCT/US2008/002636 mailed Jul. 2, 2008.

(Continued)

*Primary Examiner* — Leslie Deak
*Assistant Examiner* — Jordan B Bailey
(74) *Attorney, Agent, or Firm* — Wolf, Greenfield & Sacks, P.C.

(57) ABSTRACT

A reagent supply arrangement for a hemodialysis system may include an E-prong connector having three parallel prongs with two outer prongs arranged in a common plane and a center prong arranged above the common plane, a first supply line for a first reagent connected in fluid communication with one of the outer prongs, a second supply line for a second reagent connected in fluid communication with the other of the outer prongs, a liquid line connected in fluid communication with the center prong, and a container for housing the first reagent having an inlet connected to the liquid line and an outlet connected to the first supply line for the first reagent. The E-prong connector may help prevent the improper connection to the dialysis unit, e.g., because the prong arrangement ensures connection in only one way to the dialysis unit.

14 Claims, 28 Drawing Sheets

U.S. PATENT DOCUMENTS

| | | | |
|---|---|---|---|
| 2,741,099 A | 4/1956 | Beane | |
| 2,816,514 A | 12/1957 | Freese | |
| 3,016,563 A | 1/1962 | De Jong | |
| 3,200,648 A | 8/1965 | Waggaman | |
| 3,508,656 A | 4/1970 | Serfass et al. | |
| 3,539,081 A | 11/1970 | Norton et al. | |
| 3,656,873 A | 4/1972 | Schiff | |
| 3,759,483 A | 9/1973 | Baxter | |
| RE27,849 E | 12/1973 | Wortman | |
| 3,827,561 A | 8/1974 | Serfass et al. | |
| 3,882,861 A | 5/1975 | Kettering et al. | |
| 3,936,729 A | 2/1976 | Winslow | |
| 4,096,211 A | 6/1978 | Rameau | |
| 4,096,859 A | 6/1978 | Agarwal et al. | |
| 4,133,312 A | 1/1979 | Burd | |
| 4,155,852 A | 5/1979 | Fischel et al. | |
| 4,161,264 A | 7/1979 | Malmgren et al. | |
| 4,266,814 A | 5/1981 | Gallagher | |
| 4,267,040 A | 5/1981 | Schal | |
| 4,282,099 A | 8/1981 | Jones | |
| 4,299,784 A | 11/1981 | Hense | |
| 4,309,592 A | 1/1982 | Le Boeuf | |
| 4,322,054 A | 3/1982 | Campbell | |
| 4,362,156 A | 12/1982 | Feller et al. | |
| 4,369,781 A | 1/1983 | Gilson et al. | |
| 4,398,908 A | 8/1983 | Siposs | |
| 4,439,188 A | 3/1984 | Dennehey et al. | |
| 4,441,357 A | 4/1984 | Kahn et al. | |
| 4,479,760 A | 10/1984 | Bilstad et al. | |
| 4,479,761 A | 10/1984 | Bilstad et al. | |
| 4,479,762 A | 10/1984 | Bilstad et al. | |
| 4,490,254 A | 12/1984 | Gordon et al. | |
| 4,501,405 A | 2/1985 | Usry | |
| 4,574,876 A | 3/1986 | Aid | |
| 4,585,442 A | 4/1986 | Mannes | |
| 4,623,334 A | 11/1986 | Riddell | |
| 4,623,450 A | 11/1986 | Vantard et al. | |
| 4,664,891 A | 5/1987 | Cosentino et al. | |
| 4,680,445 A | 7/1987 | Ogawa | |
| 4,695,385 A | 9/1987 | Boag | |
| 4,731,072 A | 3/1988 | Aid | |
| 4,770,769 A | 9/1988 | Schael et al. | |
| 4,778,451 A | 10/1988 | Kamen | |
| 4,784,495 A * | 11/1988 | Jonsson et al. | 366/151.1 |
| 4,808,161 A | 2/1989 | Kamen | |
| 4,822,343 A | 4/1989 | Beiser | |
| 4,826,482 A | 5/1989 | Kamen | |
| 4,828,543 A | 5/1989 | Weiss et al. | |
| 4,833,329 A | 5/1989 | Quint et al. | |
| 4,906,816 A | 3/1990 | van Leerdam | |
| 4,927,411 A | 5/1990 | Pastrone et al. | |
| 4,950,235 A | 8/1990 | Slate et al. | |
| 4,971,700 A | 11/1990 | Tsuji et al. | |
| 4,976,162 A | 12/1990 | Kamen | |
| 4,997,570 A | 3/1991 | Polaschegg | |
| 5,024,756 A | 6/1991 | Sternby | |
| 5,033,513 A | 7/1991 | Bartholomew | |
| 5,061,241 A | 10/1991 | Stephens, Jr. et al. | |
| 5,062,774 A | 11/1991 | Kramer et al. | |
| 5,074,838 A | 12/1991 | Kroyer | |
| 5,088,515 A | 2/1992 | Kamen | |
| 5,088,901 A | 2/1992 | Brauer | |
| 5,100,554 A | 3/1992 | Polaschegg | |
| 5,105,981 A | 4/1992 | Gehman | |
| 5,110,447 A | 5/1992 | MacWilliams et al. | |
| 5,110,477 A | 5/1992 | Howard et al. | |
| 5,116,316 A | 5/1992 | Sertic et al. | |
| 5,125,069 A | 6/1992 | O'Boyle | |
| 5,160,325 A * | 11/1992 | Nichols et al. | 604/247 |
| 5,178,182 A | 1/1993 | Kamen | |
| 5,245,693 A | 9/1993 | Ford et al. | |
| 5,247,434 A | 9/1993 | Peterson et al. | |
| 5,267,956 A | 12/1993 | Beuchat | |
| 5,278,072 A | 1/1994 | Wall et al. | |
| 5,300,044 A | 4/1994 | Classey et al. | |
| 5,306,242 A | 4/1994 | Joyce et al. | |
| 5,324,422 A | 6/1994 | Colleran et al. | |
| 5,326,476 A | 7/1994 | Grogan et al. | |
| D350,823 S | 9/1994 | Lanigan | |
| D350,850 S | 9/1994 | Angelini | |
| 5,349,896 A | 9/1994 | Delaney, III et al. | |
| 5,350,357 A | 9/1994 | Kamen et al. | |
| 5,351,686 A | 10/1994 | Steuer et al. | |
| 5,378,126 A | 1/1995 | Abrahamson et al. | |
| 5,381,510 A | 1/1995 | Ford et al. | |
| 5,385,540 A | 1/1995 | Abbott et al. | |
| 5,395,316 A * | 3/1995 | Martin | 604/43 |
| 5,410,255 A | 4/1995 | Bailey | |
| 5,411,472 A | 5/1995 | Steg, Jr. et al. | |
| 5,413,566 A | 5/1995 | Sevrain et al. | |
| 5,420,962 A | 5/1995 | Bakke | |
| 5,421,823 A | 6/1995 | Kamen et al. | |
| 5,423,738 A | 6/1995 | Robinson et al. | |
| 5,429,485 A | 7/1995 | Dodge | |
| 5,431,626 A | 7/1995 | Bryant et al. | |
| 5,438,510 A | 8/1995 | Bryant et al. | |
| 5,441,231 A | 8/1995 | Payne et al. | |
| 5,441,343 A | 8/1995 | Pylkki et al. | |
| 5,441,636 A | 8/1995 | Chevallet et al. | |
| 5,472,614 A | 12/1995 | Rossi | |
| 5,474,683 A | 12/1995 | Bryant et al. | |
| 5,476,368 A | 12/1995 | Rabenau et al. | |
| 5,476,444 A | 12/1995 | Keeling et al. | |
| 5,482,440 A | 1/1996 | Dennehey et al. | |
| 5,486,286 A | 1/1996 | Peterson et al. | |
| 5,487,827 A | 1/1996 | Peterson et al. | |
| 5,496,273 A | 3/1996 | Pastrone et al. | |
| 5,527,507 A | 6/1996 | Childers et al. | |
| 5,541,344 A | 7/1996 | Becker et al. | |
| 5,542,919 A | 8/1996 | Simon et al. | |
| 5,558,255 A | 9/1996 | Sancoff et al. | |
| 5,568,362 A | 10/1996 | Hansson | |
| 5,575,310 A | 11/1996 | Kamen et al. | |
| 5,578,012 A | 11/1996 | Kamen et al. | |
| 5,580,460 A | 12/1996 | Polaschegg et al. | |
| 5,586,438 A | 12/1996 | Fahy et al. | |
| 5,591,344 A | 1/1997 | Kenley et al. | |
| 5,591,389 A * | 1/1997 | Esrock | 264/171.12 |
| 5,593,290 A | 1/1997 | Greisch et al. | |
| 5,628,908 A | 5/1997 | Kamen et al. | |
| 5,632,894 A | 5/1997 | White et al. | |
| 5,634,896 A | 6/1997 | Bryant et al. | |
| 5,645,531 A | 7/1997 | Thompson et al. | |
| 5,651,765 A | 7/1997 | Haworth et al. | |
| 5,651,893 A | 7/1997 | Kenley et al. | |
| 5,651,898 A | 7/1997 | Imura | |
| 5,690,831 A | 11/1997 | Kenley et al. | |
| 5,692,729 A | 12/1997 | Harhen | |
| 5,729,653 A | 3/1998 | Magliochetti et al. | |
| 5,730,720 A | 3/1998 | Sites et al. | |
| 5,744,027 A | 4/1998 | Connell et al. | |
| 5,755,275 A | 5/1998 | Rose et al. | |
| 5,755,683 A | 5/1998 | Houle et al. | |
| 5,776,091 A | 7/1998 | Brugger et al. | |
| 5,782,508 A | 7/1998 | Bartholomew | |
| 5,797,897 A | 8/1998 | Jepson et al. | |
| 5,875,282 A | 2/1999 | Jordan et al. | |
| 5,879,316 A | 3/1999 | Safar et al. | |
| 5,882,047 A | 3/1999 | Ostrander et al. | |
| 5,899,873 A | 5/1999 | Jones et al. | |
| 5,902,476 A | 5/1999 | Twardowski et al. | |
| 5,931,648 A | 8/1999 | Del Canizo | |
| 5,932,103 A | 8/1999 | Kenley et al. | |
| 5,932,110 A | 8/1999 | Shah et al. | |
| 5,938,634 A | 8/1999 | Packard | |
| 5,947,931 A | 9/1999 | Bierman et al. | |
| 5,989,423 A | 11/1999 | Kamen et al. | |
| 6,041,801 A | 3/2000 | Gray et al. | |
| 6,042,784 A | 3/2000 | Wamsiedler et al. | |
| 6,047,108 A | 4/2000 | Sword et al. | |
| 6,062,068 A | 5/2000 | Bowling et al. | |
| 6,070,761 A | 6/2000 | Bloom et al. | |
| 6,101,406 A | 8/2000 | Hacker et al. | |
| 6,109,881 A | 8/2000 | Snodgrass et al. | |
| 6,136,201 A | 10/2000 | Shah et al. | |
| 6,139,819 A | 10/2000 | Unger et al. | |
| 6,142,164 A | 11/2000 | Wier et al. | |

| Patent No. | Date | Name |
|---|---|---|
| 6,142,446 A * | 11/2000 | Leinsing .................... 251/149.1 |
| 6,146,354 A * | 11/2000 | Beil ............................ 604/28 |
| 6,146,523 A | 11/2000 | Kenley et al. |
| 6,146,536 A | 11/2000 | Twardowski |
| 6,153,102 A | 11/2000 | Kenley et al. |
| 6,159,192 A | 12/2000 | Fowles et al. |
| 6,171,261 B1 | 1/2001 | Niermann et al. |
| 6,176,904 B1 | 1/2001 | Gupta |
| 6,210,361 B1 | 4/2001 | Kamen et al. |
| 6,213,996 B1 | 4/2001 | Jepson et al. |
| 6,223,130 B1 | 4/2001 | Gray et al. |
| 6,234,997 B1 | 5/2001 | Kamen et al. |
| RE37,324 E | 8/2001 | Esrock |
| 6,274,303 B1 | 8/2001 | Wowk et al. |
| 6,277,277 B1 | 8/2001 | Jacobi et al. |
| 6,284,131 B1 | 9/2001 | Hogard et al. |
| 6,302,653 B1 | 10/2001 | Bryant et al. |
| 6,321,597 B1 | 11/2001 | Demers et al. |
| 6,331,778 B1 | 12/2001 | Daily et al. |
| 6,336,003 B1 | 1/2002 | Mitsunaga et al. |
| 6,336,911 B1 | 1/2002 | Westerbeck |
| 6,347,633 B1 | 2/2002 | Groth et al. |
| 6,382,923 B1 | 5/2002 | Gray |
| 6,406,426 B1 | 6/2002 | Reuss et al. |
| 6,406,452 B1 | 6/2002 | Westerbeck |
| 6,413,233 B1 | 7/2002 | Sites et al. |
| 6,415,797 B1 | 7/2002 | Groth et al. |
| 6,416,293 B1 | 7/2002 | Bouchard et al. |
| 6,423,053 B1 | 7/2002 | Lee |
| 6,464,666 B1 | 10/2002 | Augustine et al. |
| 6,480,257 B2 | 11/2002 | Cassidy et al. |
| 6,485,263 B1 | 11/2002 | Bryant et al. |
| 6,491,656 B1 | 12/2002 | Morris |
| 6,497,676 B1 | 12/2002 | Childers et al. |
| 6,517,510 B1 | 2/2003 | Stewart et al. |
| 6,520,747 B2 | 2/2003 | Gray et al. |
| 6,527,758 B2 | 3/2003 | Ko |
| 6,529,775 B2 | 3/2003 | Whitebook et al. |
| 6,535,689 B2 | 3/2003 | Augustine et al. |
| 6,537,445 B2 | 3/2003 | Muller |
| 6,539,172 B2 | 3/2003 | Akahane |
| 6,543,814 B2 | 4/2003 | Bartholomew |
| 6,579,253 B1 | 6/2003 | Burbank et al. |
| 6,579,496 B1 | 6/2003 | Fausset et al. |
| RE38,203 E | 7/2003 | Kelly |
| 6,595,944 B2 | 7/2003 | Balschat et al. |
| 6,595,948 B2 | 7/2003 | Suzuki et al. |
| 6,604,908 B1 | 8/2003 | Bryant et al. |
| 6,608,968 B2 | 8/2003 | Bakke |
| 6,660,974 B2 | 12/2003 | Faries, Jr. et al. |
| 6,663,353 B2 | 12/2003 | Lipscomb et al. |
| 6,663,359 B2 | 12/2003 | Gray |
| 6,673,314 B1 | 1/2004 | Burbank et al. |
| 6,709,417 B1 | 3/2004 | Houle et al. |
| 6,722,865 B2 | 4/2004 | Domroese |
| 6,723,062 B1 | 4/2004 | Westberg et al. |
| 6,726,656 B2 | 4/2004 | Kamen et al. |
| 6,743,201 B1 | 6/2004 | Donig et al. |
| 6,749,403 B2 | 6/2004 | Bryant et al. |
| 6,752,172 B2 | 6/2004 | Lauer |
| 6,768,085 B2 | 7/2004 | Faries et al. |
| 6,775,473 B2 | 8/2004 | Augustine et al. |
| 6,788,885 B2 | 9/2004 | Mitsunaga et al. |
| 6,808,369 B2 | 10/2004 | Gray et al. |
| 6,814,547 B2 | 11/2004 | Childers et al. |
| 6,814,718 B2 * | 11/2004 | McGuckin et al. ............ 604/264 |
| 6,826,948 B1 | 12/2004 | Bhatti et al. |
| 6,858,019 B2 * | 2/2005 | McGuckin et al. ............. 604/43 |
| 6,860,866 B1 | 3/2005 | Graf et al. |
| 6,868,309 B1 | 3/2005 | Begelman |
| 6,877,713 B1 | 4/2005 | Gray et al. |
| 6,905,314 B2 | 6/2005 | Danby |
| 6,905,479 B1 | 6/2005 | Bouchard et al. |
| 6,929,751 B2 | 8/2005 | Bowman et al. |
| 6,939,471 B2 | 9/2005 | Gross et al. |
| 6,949,079 B1 | 9/2005 | Westberg et al. |
| 6,953,323 B2 | 10/2005 | Childers et al. |
| 7,029,245 B2 | 4/2006 | Maianti et al. |
| 7,083,719 B2 | 8/2006 | Bowman et al. |
| 7,122,210 B2 | 10/2006 | Elisabettini et al. |
| 7,124,996 B2 | 10/2006 | Clarke et al. |
| 7,147,613 B2 | 12/2006 | Burbank et al. |
| 7,168,334 B1 | 1/2007 | Drott |
| 7,169,303 B2 | 1/2007 | Sullivan et al. |
| 7,175,397 B2 | 2/2007 | Claude et al. |
| 7,175,606 B2 | 2/2007 | Bowman et al. |
| 7,214,210 B2 | 5/2007 | Kamen et al. |
| 7,238,164 B2 | 7/2007 | Childers et al. |
| 7,273,465 B2 | 9/2007 | Ash |
| 7,300,413 B2 | 11/2007 | Burbank et al. |
| 7,303,540 B2 | 12/2007 | O'Mahony et al. |
| 7,318,292 B2 | 1/2008 | Helbling et al. |
| 7,318,892 B2 | 1/2008 | Connell et al. |
| 7,410,294 B2 | 8/2008 | Shiraki et al. |
| 7,461,968 B2 | 12/2008 | Demers et al. |
| 7,465,285 B2 | 12/2008 | Hutchinson et al. |
| 7,488,448 B2 | 2/2009 | Wieting et al. |
| 7,500,962 B2 | 3/2009 | Childers et al. |
| 7,544,179 B2 | 6/2009 | Distler et al. |
| 7,559,524 B2 | 7/2009 | Gray et al. |
| 7,601,636 B2 | 10/2009 | Dumas et al. |
| 7,632,078 B2 | 12/2009 | Demers et al. |
| 7,632,080 B2 | 12/2009 | Tracey et al. |
| 7,662,286 B2 | 2/2010 | Childers et al. |
| 7,717,682 B2 | 5/2010 | Orr |
| 7,727,176 B2 | 6/2010 | Tonelli et al. |
| 7,744,553 B2 | 6/2010 | Kelly et al. |
| 7,776,301 B2 | 8/2010 | Comrie et al. |
| 7,794,141 B2 | 9/2010 | Perry et al. |
| 7,815,595 B2 | 10/2010 | Busby et al. |
| 7,867,214 B2 | 1/2011 | Childers et al. |
| 7,892,197 B2 | 2/2011 | Folden et al. |
| 7,896,830 B2 | 3/2011 | Gura et al. |
| 7,935,074 B2 | 5/2011 | Plahey et al. |
| 7,935,250 B2 | 5/2011 | Castellano et al. |
| 7,967,022 B2 | 6/2011 | Grant et al. |
| 8,002,726 B2 | 8/2011 | Karoor et al. |
| 8,042,563 B2 | 10/2011 | Grant et al. |
| 2002/0056672 A1 | 5/2002 | Lyle et al. |
| 2002/0103453 A1 | 8/2002 | Burbank et al. |
| 2002/0150476 A1 | 10/2002 | Lucke et al. |
| 2002/0179505 A1 | 12/2002 | Rovatti et al. |
| 2002/0179595 A1 | 12/2002 | Nagele |
| 2002/0182090 A1 | 12/2002 | Gray |
| 2003/0114795 A1 | 6/2003 | Faries et al. |
| 2003/0194332 A1 | 10/2003 | Jahn et al. |
| 2003/0195453 A1 | 10/2003 | Han et al. |
| 2003/0195454 A1 | 10/2003 | Wariar et al. |
| 2003/0220599 A1 | 11/2003 | Lundtveit et al. |
| 2003/0220607 A1 | 11/2003 | Busby et al. |
| 2003/0229302 A1 | 12/2003 | Robinson et al. |
| 2003/0230191 A1 | 12/2003 | Ohrle et al. |
| 2004/0001766 A1 | 1/2004 | Maianti et al. |
| 2004/0009096 A1 | 1/2004 | Wellman |
| 2004/0019313 A1 | 1/2004 | Childers et al. |
| 2004/0091374 A1 | 5/2004 | Gray |
| 2004/0101026 A1 | 5/2004 | Nitta et al. |
| 2004/0138607 A1 | 7/2004 | Burbank et al. |
| 2004/0245161 A1 | 12/2004 | Treu et al. |
| 2004/0262917 A1 | 12/2004 | Sunohara et al. |
| 2005/0020958 A1 | 1/2005 | Paolini et al. |
| 2005/0045540 A1 | 3/2005 | Connell et al. |
| 2005/0069425 A1 | 3/2005 | Gray et al. |
| 2005/0069427 A1 | 3/2005 | Roemuss et al. |
| 2005/0095141 A1 | 5/2005 | Lanigan et al. |
| 2005/0095154 A1 | 5/2005 | Tracey et al. |
| 2005/0126988 A1 | 6/2005 | Thacker et al. |
| 2005/0126998 A1 | 6/2005 | Childers |
| 2005/0130332 A1 | 6/2005 | Ishii et al. |
| 2005/0131332 A1 | 6/2005 | Kelly et al. |
| 2005/0230292 A1 | 10/2005 | Beden et al. |
| 2005/0234385 A1 | 10/2005 | Vandlik |
| 2005/0242034 A1 | 11/2005 | Connell et al. |
| 2005/0274658 A1 | 12/2005 | Rosenbaum et al. |
| 2006/0002823 A1 | 1/2006 | Feldstein |
| 2006/0093531 A1 | 5/2006 | Tremoulet et al. |
| 2006/0184084 A1 | 8/2006 | Ware et al. |
| 2006/0195064 A1 | 8/2006 | Plahey et al. |

| | | |
|---|---|---|
| 2006/0241550 A1 | 10/2006 | Kamen et al. |
| 2007/0060786 A1 | 3/2007 | Gura et al. |
| 2007/0077156 A1 | 4/2007 | Orr |
| 2007/0112297 A1 | 5/2007 | Plahey et al. |
| 2007/0135758 A1 | 6/2007 | Childers et al. |
| 2007/0166181 A1 | 7/2007 | Nilson |
| 2007/0253463 A1 | 11/2007 | Perry et al. |
| 2007/0255527 A1 | 11/2007 | Schick et al. |
| 2007/0278155 A1 | 12/2007 | Lo et al. |
| 2008/0015493 A1 | 1/2008 | Childers et al. |
| 2008/0033346 A1 | 2/2008 | Childers et al. |
| 2008/0058697 A1 | 3/2008 | Kamen et al. |
| 2008/0058712 A1 | 3/2008 | Plahey |
| 2008/0077068 A1 | 3/2008 | Orr |
| 2008/0097283 A1 | 4/2008 | Plahey |
| 2008/0105600 A1 | 5/2008 | Connell et al. |
| 2008/0125693 A1 | 5/2008 | Gavin et al. |
| 2008/0132828 A1 | 6/2008 | Howard |
| 2008/0161751 A1 | 7/2008 | Plahey et al. |
| 2008/0175719 A1 | 7/2008 | Tracey et al. |
| 2008/0202591 A1 | 8/2008 | Grant et al. |
| 2008/0204086 A1 | 8/2008 | Park et al. |
| 2008/0205481 A1 | 8/2008 | Faries, Jr. et al. |
| 2008/0208103 A1 | 8/2008 | Demers et al. |
| 2008/0208111 A1 | 8/2008 | Kamen et al. |
| 2008/0215898 A1 | 9/2008 | Lu et al. |
| 2008/0216898 A1 | 9/2008 | Grant et al. |
| 2008/0240929 A1 | 10/2008 | Kamen et al. |
| 2008/0253427 A1 | 10/2008 | Kamen et al. |
| 2008/0253911 A1 | 10/2008 | Demers et al. |
| 2008/0253912 A1 | 10/2008 | Demers et al. |
| 2008/0287854 A1 | 11/2008 | Sun |
| 2009/0004033 A1 | 1/2009 | Demers et al. |
| 2009/0007642 A1 | 1/2009 | Busby et al. |
| 2009/0008331 A1 | 1/2009 | Wilt et al. |
| 2009/0009290 A1 | 1/2009 | Kneip et al. |
| 2009/0012447 A1 | 1/2009 | Huitt et al. |
| 2009/0012448 A1 | 1/2009 | Childers et al. |
| 2009/0012449 A1 | 1/2009 | Lee et al. |
| 2009/0012450 A1 | 1/2009 | Shah et al. |
| 2009/0012452 A1 | 1/2009 | Slepicka et al. |
| 2009/0012453 A1 | 1/2009 | Childers et al. |
| 2009/0012454 A1 | 1/2009 | Childers |
| 2009/0012455 A1 | 1/2009 | Childers et al. |
| 2009/0012456 A1 | 1/2009 | Childers et al. |
| 2009/0012457 A1 | 1/2009 | Childers et al. |
| 2009/0012458 A1 | 1/2009 | Childers et al. |
| 2009/0012460 A1 | 1/2009 | Steck et al. |
| 2009/0012461 A1 | 1/2009 | Childers et al. |
| 2009/0024070 A1 | 1/2009 | Gelfand et al. |
| 2009/0043239 A1 | 2/2009 | Gagel et al. |
| 2009/0076434 A1 | 3/2009 | Mischelevich et al. |
| 2009/0088683 A1 | 4/2009 | Roger et al. |
| 2009/0095679 A1 | 4/2009 | Demers et al. |
| 2009/0101549 A1 | 4/2009 | Kamen et al. |
| 2009/0101566 A1 | 4/2009 | Crnkovich et al. |
| 2009/0105621 A1 | 4/2009 | Boyd et al. |
| 2009/0105629 A1 | 4/2009 | Grant et al. |
| 2009/0107335 A1 | 4/2009 | Wilt et al. |
| 2009/0107902 A1 | 4/2009 | Childers et al. |
| 2009/0112151 A1 | 4/2009 | Chapman et al. |
| 2009/0113335 A1 | 4/2009 | Sandoe et al. |
| 2009/0114582 A1 | 5/2009 | Grant et al. |
| 2009/0154524 A1 | 6/2009 | Girelli |
| 2009/0173682 A1 | 7/2009 | Robinson et al. |
| 2009/0182263 A1* | 7/2009 | Burbank et al. ............... 604/28 |
| 2009/0192367 A1 | 7/2009 | Braig et al. |
| 2009/0202367 A1 | 8/2009 | Gray et al. |
| 2010/0051529 A1 | 3/2010 | Grant et al. |
| 2010/0056975 A1 | 3/2010 | Dale et al. |
| 2010/0057016 A1 | 3/2010 | Dale et al. |
| 2010/0133153 A1 | 6/2010 | Beden et al. |
| 2010/0137782 A1 | 6/2010 | Jansson et al. |
| 2010/0185134 A1 | 7/2010 | Houwen et al. |
| 2010/0187176 A1 | 7/2010 | Lopez |
| 2010/0192686 A1 | 8/2010 | Kamen et al. |
| 2010/0296953 A1 | 11/2010 | Gray |
| 2010/0327849 A1 | 12/2010 | Kamen et al. |
| 2011/0009797 A1 | 1/2011 | Kelly et al. |
| 2011/0092875 A1 | 4/2011 | Beck |
| 2011/0105877 A1 | 5/2011 | Wilt et al. |
| 2011/0218600 A1 | 9/2011 | Kamen et al. |
| 2011/0299358 A1 | 12/2011 | Wilt et al. |
| 2011/0303588 A1 | 12/2011 | Kelly et al. |
| 2011/0303598 A1 | 12/2011 | Lo et al. |
| 2012/0106289 A1 | 5/2012 | Wilt et al. |

FOREIGN PATENT DOCUMENTS

| | | |
|---|---|---|
| EP | 0 815 882 A2 | 1/1998 |
| EP | 0 992 255 A2 | 4/2000 |
| EP | 2 319 551 A2 | 5/2011 |
| WO | WO 94/20158 A1 | 9/1994 |
| WO | WO 98/37801 A1 | 9/1998 |
| WO | WO 98/39058 A1 | 9/1998 |
| WO | WO 99/10028 A1 | 3/1999 |
| WO | WO 01/37895 A2 | 5/2001 |
| WO | WO 02/03879 A1 | 1/2002 |
| WO | WO 02/30267 A2 | 4/2002 |
| WO | WO 2004/041081 A1 | 5/2004 |
| WO | WO 2005/044339 A1 | 5/2005 |
| WO | WO 2005/044435 A2 | 5/2005 |
| WO | WO 2006/120415 A1 | 11/2006 |
| WO | WO 2007/120812 A2 | 10/2007 |
| WO | WO 2007/126360 A1 | 11/2007 |
| WO | WO 2008/028653 A2 | 3/2008 |
| WO | WO 2008/106191 A2 | 9/2008 |
| WO | WO 2008/106440 A1 | 9/2008 |
| WO | WO 2008/106452 A1 | 9/2008 |
| WO | WO 2008/106538 A2 | 9/2008 |
| WO | WO 2008/118600 A1 | 10/2008 |
| WO | WO 2009/051669 A1 | 4/2009 |
| WO | WO 2009/094179 A2 | 7/2009 |
| WO | WO 2009/094183 A1 | 7/2009 |
| WO | WO 2010/027435 A1 | 3/2010 |
| WO | WO 2010/027437 A2 | 3/2010 |
| WO | WO 2011/053810 A2 | 5/2011 |

OTHER PUBLICATIONS

International Preliminary Report on Patentability for Application No. PCT/US2008/002636 mailed Sep. 11, 2009.
International Search Report and Written Opinion for Application No. PCT/US2008/055000 mailed Aug. 1, 2008.
International Preliminary Report on Patentability for Application No. PCT/US2008/055000 mailed Sep. 11, 2009.
Invitation to Pay Additional Fees for Application No. PCT/US2008/055168 mailed Aug. 5, 2008.
International Search Report and Written Opinion for Application No. PCT/US2008/055168 mailed Nov. 10, 2008.
International Preliminary Report on Patentability for Application No. PCT/US2008/055168 mailed Sep. 11, 2009.
International Search Report and Written Opinion for Application No. PCT/US2008/055136 mailed Jul. 24, 2008.
International Preliminary Report on Patentability for Application No. PCT/US2008/055136 mailed Sep. 11, 2009.
Invitation to Pay Additional Fees for Application No. PCT/US2009/004866 mailed Nov. 27, 2009.
International Search Report and Written Opinion for Application No. PCT/US2009/004866 mailed Jan. 27, 2010.
International Preliminary Report on Patentability for Application No. PCT/US2009/004866 mailed Mar. 10, 2011.
Invitation to Pay Additional Fees for Application No. PCT/US2009/004877 mailed Dec. 8, 2009.
International Search Report and Written Opinion for Application No. PCT/US2009/004877 mailed Feb. 12, 2010.
International Preliminary Report on Patentability for Application No. PCT/US2009/004877 mailed Mar. 10, 2011.
Written Opinion for Application No. PCT/US2007/009107 mailed Aug. 17, 2007.
International Preliminary Report on Patentability for Application No. PCT/US2007/009107 mailed Oct. 23, 2008.
Partial European Search Report for Application No. 11150584.8 mailed Mar. 30, 2011.
Extended European Search Report for Application No. 11150584.8 mailed Jul. 26, 2011.

International Search Report and Written Opinion for Application No. PCT/US2008/011663 mailed Feb. 20, 2009.
International Preliminary Report on Patentability for Application No. PCT/US2008/011663 mailed Apr. 22, 2010.
Invitation to Pay Additional Fees for Application No. PCT/US2009/000433 mailed Jun. 4, 2009.
International Search Report and Written Opinion for Application No. PCT/US2009/000433 mailed Sep. 25, 2009.
International Preliminary Report on Patentability for Application No. PCT/US2009/000433 mailed Aug. 5, 2010.
International Search Report and Written Opinion for Application No. PCT/US2008/055021 mailed Jul. 23, 2008.
International Preliminary Report on Patentability for Application No. PCT/US2008/055021 mailed Sep. 11, 2009.
Office Action for U.S. Appl. No. 12/072,908, filed Feb. 27, 2008, published as US 2009-0008331 on Jan. 8, 2009 which Office Action is dated Oct. 15, 2010, and claims as pending for U.S. Appl. No. 12/072,908 as of Oct. 15, 2010.
Office Action for U.S. Appl. No. 12/072,908, filed Feb. 27, 2008, published as US 2009-0008331 on Jan. 8, 2009 which Office Action is dated Jul. 15, 2011, and claims as pending for U.S. Appl. No. 12/072,908 as of Jul. 15, 2011.
Office Action for U.S. Appl. No. 11/871,712, filed Oct. 12, 2007, published as US 2009/0004033 on Jan. 1, 2009, which Office Action is dated Feb. 4, 2010, and claims as pending for U.S. Appl. No. 11/871,712 as of Feb. 4, 2010.
Office Action for U.S. Appl. No. 11/871,712, filed Oct. 12, 2007, published as US 2009-0004033 on Jan. 1, 2009, which Office Action is dated Oct. 15, 2010, and claims as pending for U.S. Appl. No. 11/871,712 as of Oct. 15, 2010.
Office Action for U.S. Appl. No. 11/871,712, filed Oct. 12, 2007, published as US 2009-0004033 on Jan. 1, 2009, which Office Action is dated Feb. 7, 2011, and claims as pending for U.S. Appl. No. 11/871,712 as of Feb. 7, 2011.
Notice of Allowance for U.S. Appl. No. 11/871,803, filed Oct. 12, 2007, published as 2008-0202591 on Aug. 28, 2008, which Notice of Allowance is dated Sep. 14, 2010, and claims as allowed for U.S. Appl. No. 11/871,803 as of Sep. 14, 2010.
Notice of Allowance for U.S. Appl. No. 11/871,803, filed Oct. 12, 2007, published as 2008-0202591 on Aug. 28, 2008, which Notice of Allowance is dated Jan. 10, 2011, and claims as allowed for U.S. Appl. No. 11/871,803 as of Jan. 10, 2011.
Office Action for U.S. Appl. No. 12/038,648, filed Feb. 27, 2008, published as US 2008-0216898 on Sep. 11, 2008, which Office Action is dated Oct. 1, 2010, and claims as pending for U.S. Appl. No. 12/038,648 as of Oct. 1, 2010.
Ex Parte Quayle Action for U.S. Appl. No. 12/038,648, filed Feb. 27, 2008, published as 2008-0216898, on Sep. 11, 2008, which Office Action is dated Mar. 29, 2011, and claims as pending for U.S. Appl. No. 12/038,648 as of Mar. 29, 2011.
Notice of Allowance for U.S. Appl. No. 12/038,648, filed Feb. 27, 2008, published as US 2008-0216898 on Sep. 11, 2008, which Notice of Allowance is dated Jun. 13, 2011, and claims as allowed for U.S. Appl. No. 12/038,648 as of Jun. 13, 2011.
Office Action for U.S. Appl. No. 12/199,176, filed Aug. 27, 2008, published as 2010-0056975 on Mar. 4, 2010, which Office Action is dated Nov. 22, 2010, and claims as pending for U.S. Appl. No. 12/199,176 as of Nov. 22, 2010.
Office Action for U.S. Appl. No. 12/199,176, filed Aug. 27, 2008, published as 2010-0056975 on Mar. 4, 2010, which Office Action is dated Sep. 2, 2011, and claims as pending for U.S. Appl. No. 12/199,176 as of Sep. 2, 2011.
Office Action for U.S. Appl. No. 11/787,212, filed Apr. 13, 2007, published as 2008-0175719 on Jul. 24, 2008, which Office Action is dated May 26, 2010, and claims as pending for U.S. Appl. No. 11/787,212 as of May 26, 2010.
Office Action for U.S. Appl. No. 11/787,212, filed Apr. 13, 2007, published as 2008-0175719 on Jul. 24, 2008, which Office Action is dated Feb. 7, 2011, and claims as pending for U.S. Appl. No. 11/787,212 as of Feb. 7, 2011.
Office Action for U.S. Appl. No. 11/787,213, filed Apr. 13, 2007, published as 2008-0058697 on Mar. 6, 2008, which Office Action is dated Mar. 18, 2010, and claims as pending for U.S. Appl. No. 11/787,213 as of Mar. 18, 2010.
Office Action for U.S. Appl. No. 11/787,112, filed Apr. 13, 2007, published as US 2007/0253463 on Nov. 1, 2007, which Office Action is dated Nov. 21, 2008, and claims as pending for U.S. Appl. No. 11/787,112 as of Nov. 21, 2008.
Notice of Allowance for U.S. Appl. No. 11/787,112, filed Apr. 13, 2007, published as US 2007/0253463 on Nov. 1, 2007, which Notice of Allowance is dated Jun. 30, 2009, and claims as allowed for U.S. Appl. No. 11/787,112 as of Jun. 30, 2009.
Notice of Allowance for U.S. Appl. No. 11/787,112, filed Apr. 13, 2007, published as US 2007/0253463 on Nov. 1, 2007, which Notice of Allowance is dated Jan. 12, 2010, and claims as allowed for U.S. Appl. No. 11/787,112 as of Jan. 12, 2010.
Notice of Allowance for U.S. Appl. No. 11/787,112, filed Apr. 13, 2007, published as US 2007/0253463 on Nov. 1, 2007, which Notice of Allowance is dated Apr. 29, 2010, and claims as allowed for U.S. Appl. No. 11/787,112 as of Apr. 29, 2010.
Notice of Allowance for U.S. Appl. No. 11/787,112, filed Apr. 13, 2007, published as US 2007/0253463 on Nov. 1, 2007, which Notice of Allowance is dated Jul. 19, 2010. and claims as allowed for U.S. Appl. No. 11/787,112 as of Jul. 19, 2010.
Office Action for U.S. Appl. No. 11/871,821, filed Oct. 12, 2007, published as US 2008-0240929 on Oct. 2, 2008, which Office Action is dated Sep. 23, 2009, and claims as pending for U.S. Appl. No. 11/871,821 as of Sep. 23, 2009.
Office Action for U.S. Appl. No. 11/871,828, filed Oct. 12, 2007, published as US 2008-0208111 on Aug. 28, 2008, which Office Action is dated Mar. 11, 2010, and claims as pending for U.S. Appl. No. 11/871,828 as of Mar. 11, 2010.
Office Action for U.S. Appl. No. 11/871,828, filed Oct. 12, 2007, published as US 2008-0208111 on Aug. 28, 2008, which Office Action is dated Nov. 26, 2010, and claims as pending for U.S. Appl. No. 11/871,828 as of Nov. 26, 2010.
Notice of Allowance for U.S. Appl. No. 11/871,828, filed Oct. 12, 2007, published as US 2008-0208111 on Aug. 28, 2008, which Notice of Allowance is dated Oct. 13, 2011, and claims as allowed for U.S. Appl. No. 11/871,828 as of Oct. 13, 2011.
Bengtsson et al., Haemo dialysis software architecture design experiences. Proceedings of the 1999 International Conference on Software Engineering. ACM New York, NY. 1999:516-525.
Choppy et al., Architectural patterns for problem frames. IEE Proceedings: Software. Aug. 2005;152(4): 190-208.
Gentilini et al., Multitasked closed-loop control in anesthesia. IEEE Eng Med Biol Mag. Jan.-Feb. 2001;20(1):39-53.
Harel, Statecharts: A visual formalism for complex systems. Science of Computer Programming. 1987;8:231-274.
Krasner et al., A cookbook for using the model-view-controller user interface paradigm in smalltalk-80. JOOP. Aug. 1988;1(3):26-49.
U.S. Appl. No. 12/916,021, filed Oct. 29, 2010, Wilt et al.
U.S. Appl. No. 13/352,250, filed Jan. 17, 2012, Demers et al.
U.S. Appl. No. 13/480,236, filed May 24, 2012, Grant et al.
U.S. Appl. No. 13/480,444, filed May 24, 2012, Wilt et al.
U.S. Appl. No. 13/480,454, filed May 24, 2012, Wilt et al.
PCT/US2010/054772, May 9, 2011, International Search Report and Written Opinion.
PCT/US2010/054772, May 1, 2012, International Preliminary Report on Patentability.
International Search Report and Written Opinion for International Application No. PCT/US2010/054772 mailed May 9, 2011.
International Preliminary Report on Patentability for International Application No. PCT/US2010/054772 issued May 1, 2012.
Office Action for U.S. Appl. No. 11/871,680, filed Oct. 12, 2007, published as US 2008-0208103 on Aug. 28, 2008 which Office Action is dated Aug. 22, 2011, and claims as pending for U.S. Appl. No. 11/871,680 as of Aug. 22, 2011.
Notice of Allowance for U.S. Appl. No. 11/871,680, filed Oct. 12, 2007, published as US 2008-0208103 on Aug. 28, 2008, which Notice of Allowance is dated May 22, 2012, and claims as allowed for U.S. Appl. No. 11/871,680 as of May 22, 2012.

Notice of Allowance for U.S. Appl. No. 11/871,712, filed Oct. 12, 2007, published as US 2009-0004033 on Jan. 1, 2009, which Notice of Allowance is dated Jan. 11, 2012, and claims as allowed for U.S. Appl. No. 11/871,712 as of Jan. 11, 2012.

Office Action for U.S. Appl. No. 11/871,787, filed Oct. 12, 2007, published as US 2008-0253911 on Oct. 16, 2008, which Office Action is dated Apr. 14, 2011, and claims as pending for U.S. Appl. No. 11/871,787 as of Apr. 14, 2011.

Office Action for U.S. Appl. No. 12/038,474, filed Feb. 27, 2008, published as US 2008-0253427 on Oct. 16, 2008, which Office Action is dated Feb. 7, 2011, and claims as pending for U.S. Appl. No. 12/038,474 as of Feb. 7, 2011.

Office Action for U.S. Appl. No. 12/038,474, filed Feb. 27, 2008, published as US 2008-0253427 on Oct. 16, 2008, which Office Action is dated Sep. 1, 2011, and claims as pending for U.S. Appl. No. 12/038,474 as of Sep. 1, 2011.

Office Action for U.S. Appl. No. 12/038,474, filed Feb. 27, 2008, published as US 2008-0253427 on Oct. 16, 2008, which Office Action is dated May 15, 2012, and claims as pending for U.S. Appl. No. 12/038,474 as of May 15, 2012.

* cited by examiner

REAGENT SUPPLY FOR A HEMODIALYSIS SYSTEM

RELATED APPLICATIONS

This application is a continuation-in-part of prior U.S. application Ser. No. 12/072,908, filed Feb. 27, 2008, which claims the benefit of U.S. Provisional Application Serial No. 60/903,582, filed Feb. 27, 2007 and U.S. Provisional Application Ser. No. 60/904,024, filed Feb. 27, 2007. This application is a continuation-in-part of prior U.S. application Ser. No. 12/038,474, filed Feb. 27, 2008, which is a continuation-in-part of prior U.S. application Ser. No. 11/871,821, filed Oct. 12, 2007, which claims the benefit of U.S. Provisional Application Ser. No. 60/921,314, filed Apr. 2, 2007 and U.S. Provisional Application Ser. No. 60/904,024, filed Feb. 27, 2007. This application is a continuation-in-part of prior U.S. application Ser. No. 12/038,648, filed Feb. 2008, which is a continuation-in-part of prior U.S. application Ser. No. 11/871,803, filed Oct. 12, 2007, which claims the benefit of U.S. Provisional Application Ser. No. 60/921,314, filed Apr. 2, 2007 and U.S Provisional Application Ser. No. 60/904,024, filed Feb. 27, 2007. This application is a continuation-in-part of prior U.S. application Ser. No. 11/871,793, filed Oct. 12, 2007, which claims the benefit of U.S. Provisional Application Ser. No. 60/921,314, filed Apr. 2, 2007 and U.S. Provisional Application Ser. No. 60/904,024, filed Feb. 27, 2007. This application is a continuation-in-part of prior U.S. application Ser. No. 11/871,787, filed Oct. 12, 2007, which claims the benefit of U.S. Provisional Application Ser. No. 60/921,314, filed Apr. 2, 2007 and U.S. Provisional Application Ser. No. 60/904,024, filed Feb. 27, 2007. This application is a continuation-in-part of prior U.S. application Ser. No. 11/871,712, filed Oct. 12, 2007, which claims the benefit of U.S. Provisional Application Ser. No. 60/921,314, filed Apr. 2, 2007 and U.S. Provisional Application Ser. No. 60/904,024, filed Feb. 27, 2007. This application is a continuation-in-part of prior U.S. application Ser. No. 11/871,680, filed Oct. 12, 2007, which claims the benefit of U.S. Provisional Application Ser. No. 60/921,314, filed Apr. 2, 2007 and U.S. Provisional Application Ser. No. 60/904,024, filed Feb. 27, 2007.

FIELD OF INVENTION

The present invention generally relates to hemodialysis and similar dialysis systems, e.g., systems able to treat blood or other bodily fluids extracorporeally.

BACKGROUND

Many factors make hemodialysis inefficient, difficult, and expensive. These factors include the complexity of hemodialysis, the safety concerns related to hemodialysis, and the very large amount of dialysate needed for hemodialysis. Moreover, hemodialysis is typically performed in a dialysis center requiring skilled technicians. Therefore any increase in the ease and efficiency of the dialysis process could have an impact on treatment cost or patient outcome.

SUMMARY OF INVENTION

Aspects of the invention generally relate to hemodialysis and similar dialysis systems. Illustrative embodiments described herein involve, in some cases, interrelated products, alternative solutions to a particular problem, and/or a plurality of different uses of one or more systems and/or articles. Although the various systems and methods described herein are described in relation to hemodialysis, it should be understood that the various systems and method described herein are applicable to other dialysis systems and/or in any extracorporeal system able to treat blood or other bodily fluids, such as hemofiltration, hemodiafiltration, etc.

In one aspect of the invention, an enclosure for containing a portable hemodialysis unit is provided, where the hemodialysis unit includes suitable components for performing hemodialysis including a dialyzer, one or more pumps to circulate blood through the dialyzer, a source of dialysate, and one or more pumps to circulate the dialysate through the dialyzer. The enclosure may include a housing that supports the components of the hemodialysis unit and has a front panel at which blood circuit connections and dialysate fluidic connections are located. For example, the front panel may support blood line connections for patient blood access, connections for a reagent supply, dialyzer connections for both blood flow and dialysate, etc. Thus, in one embodiment, an operator may complete all necessary fluid circuit connections for the blood circuit and reagent supply at the housing front panel. The enclosure may also include a pair of vertical, side-by-side doors hingedly mounted to the housing at opposite sides of the front panel so that the doors are movable between open and closed positions. With the doors in an open position, an operator may have access to the blood circuit connections and dialysate fluidic connections. Also, with the doors in the closed position, access to the patient access and dialysate fluidic connections may be blocked, and the doors may allow for the retention of heat in the housing suitable for disinfection during a disinfection cycle. For example, at least one of the doors may include a seal to resist air exchange between an interior and an exterior of housing when the doors are in the closed position to help retain heat and/or help resist entry of dust, dirt or other contaminants.

In one embodiment, each of the vertical, side-by-side doors is mounted to the housing via a hinge plate that is pivotally mounted to the door at a first end, and is pivotally mounted to the housing at a second end opposite the first end. Thus, the doors may be positionable at two open positions, e.g., a first open position in which blood circuit connections and dialysate fluidic connections are exposed and the hinge plate is adjacent the housing, and a second open position in which the hinge plate is positioned away from the housing. One or more retainer members may be included to maintain the doors in an open position relative to a corresponding hinge plate. For example, the retainer member may include at least one magnet attached to the door or the hinge plate that tends to keep the door in an open position relative to the hinge plate and the housing. Also, one or more retainer members may maintain the hinge plates in a closed position relative to the housing, e.g., in a position close to the housing, and/or maintain the hinge plates in an open position away from the housing.

In one embodiment, at least one of the doors may include a container holder that is movable between a folded position and an extended position in which the container holder is arranged to support a container, such as reagent supply container. In addition, or alternately, one or both of the doors may include a hook to support a control interface for the hemodialysis unit, such as a remote interface unit that is connected to the housing by a communication cable. These features may make use of the dialysis unit easier by supporting components in a convenient location.

In another embodiment, the front panel may include at least one flanged portion to support blood lines of a blood circuit assembly. For example, the front panel may include several flanged sections arranged at a periphery of the front panel, such as at lower corners and at a top edge of the front panel. Blood circuit lines that connect to a patient may be relatively long (e.g., up to 3-4 feet or more), and may be wrapped around the periphery of the front panel and retained in place by the flanged portions. The flanged portions may be arranged to support the blood lines and allow the doors to be moved to the closed position without contacting the blood lines, e.g., to avoid pinching of the blood lines at door hinge points.

In one embodiment, the blood circuit connections at the front panel include arterial and venous blood line connectors for the blood circuit, and the dialysate fluidic connections at the front panel include a connection point for a reagent supply, dialyzer dialysate connections, and a blood line connection point for connecting the arterial and venous blood lines to a directing circuit of the dialysis unit.

The hemodialysis unit may include a control interface that is connected to the housing by a flexible cable and that is arranged to allow a user to receive information from and provide information to the hemodialysis unit. In one embodiment, the Is enclosure may include a control interface mounting area at a top of the enclosure where the control interface is mountable. For example, the control interface may include a foldable leg or other support that permits the control interface to be stood in a near vertical orientation on the top of the housing.

In another embodiment, the enclosure may include an electronics section that is separated and insulated from a disinfection section that is heated to disinfect components of the hemodialysis unit. For example, the disinfection section may include all of the liquid circuit components, such as valves, pumps, conduits, etc., of the various portions of the dialysis unit. The electronics section may include motors, computers or other data processing devices, computer memory, and/or other temperature sensitive electronics or other components. By isolating the electronics section from the disinfection section (at least to some degree), components in the electronics section may be spared exposure to the heat or other environmental conditions in the disinfection section whether during a disinfection operation or otherwise.

In another aspect of the invention, a portable hemodialysis system may be arranged so that power for the fluid circuit pumps of a dialysis unit may be provided by a modular power unit, e.g., a unit that can be selectively connected to or disconnected from the dialysis unit. As a result, failure of a power unit need not necessarily disable the entire dialysis system. Instead, the power unit may be replaced with another power unit, allowing for treatment to continue. For example, a modular assembly for a portable hemodialysis system may include a dialysis unit, e.g., including a housing that contains suitable components for performing hemodialysis, such as a dialyzer, one or more pumps to circulate blood through the dialyzer, a source of dialysate, and one or more pumps to circulate the dialysate through the dialyzer. The housing may have a front panel at which blood circuit connections and dialysate fluidic connections are located, e.g., where an operator may make patient blood access connections, connect a reagent supply, and/or connect a dialyzer. The modular assembly may also include a power unit having a housing that contains suitable components for providing operating power to the pumps of the dialysis unit. The power unit may be selectively connected to the dialysis unit and provide power to the dialysis unit for the pumps when connected to the dialysis unit, but may be incapable of providing power to the dialysis unit when disconnected from the dialysis unit. The power unit may be selectively connected to and disconnected from the dialysis unit by operation of a single handle, e.g., an operator may turn or otherwise operate a single handle to disconnect the power unit from the dialysis unit. In one embodiment, the dialysis unit and the power unit are sized and weighted to each be carried by hand by a human.

In one embodiment, the pumps of the dialysis unit are pneumatic pumps and the power unit provides pneumatic power to the dialysis unit. For example, the power unit may provide air pressure and/or vacuum to the dialysis unit to power the pumps. The power unit may include one or more air pressure pumps and/or air vacuum pumps, and the dialysis unit may include a plurality of valves to control application of pneumatic power to the pumps. To aid with use of the hemodialysis system in the home, the power unit and dialysis unit electrical power requirements may be provided by standard residential electrical power, e.g., approximately 110V, 15 amp electrical power. The dialysis unit may provide electrical power to the power unit, and the power unit may use the electrical power to generate operating power for the pumps.

In another aspect of the invention, a blood circuit assembly for a dialysis unit may be arranged to allow the replacement of most or all blood circuit components in a single operation. For example, the blood circuit assembly may include an organizing tray, a pair of pneumatic pumps mounted to the organizing tray for circulating blood received from a patient through a circuit including a dialyzer unit and returned to the patient, an air trap mounted to the organizing tray arranged to remove air from blood circulating in the circuit, a pair of dialyzer connections arranged to connect to the inlet and outlet of a dialyzer unit, and a pair of blood line connectors, one inlet blood line connector for receiving blood from the patient and providing blood to the pneumatic pumps and the other outlet blood line connector for returning blood to the patient.

In one embodiment, an anticoagulant connection is provided for engaging with an anticoagulant source and providing anticoagulant into the blood circuit. For example, the anticoagulant connection may include a pump for pumping anticoagulant from the anticoagulant source, such as heparin from a vial of heparin, to the circuit. The anticoagulant connection may include a vial holder arranged to hold two or more differently sized vials, and a spike to pierce the vial. In one embodiment, the pair of pneumatic pumps, the anticoagulant connection, and the anticoagulant pump are part of a pump cassette.

In another embodiment, the blood circuit assembly may be selectively mounted to and removed from a dialysis unit. To aid in handling of the blood circuit assembly, the organizing tray may include a pair of handles arranged for gripping by a user. The organizing tray may also include openings adjacent each of the handles for receiving retaining tabs on a dialysis unit that engage with the blood circuit assembly and retain the blood circuit assembly on the dialysis unit.

In one embodiment, the inlet blood line connector is connected to an inlet for the pump cassette, an outlet for the pump cassette is connected to a dialyzer inlet connector, a dialyzer outlet connector is connected to an inlet of the air trap, and an outlet of the air trap is connected to the outlet blood line connector. The inlet of the air trap may be located above the outlet of the air trap when the blood circuit assembly is mounted to a dialysis unit, e.g., to aid in trapping of air circulating in the circuit during treatment. The blood line connectors may be arranged for a threaded luer-type connection to a patient access, as well as be arranged for a press-in type connection to the dialysis unit. Such an arrangement may make it easier for an operator to connect the blood line connectors to the dialysis unit after treatment (e.g., for later disinfection and/or priming of the blood circuit) while allowing the connectors to engage with standard luer-type connectors at a patient blood access.

In one embodiment, the organizing tray may include circuit tube engagement members having a hole or slot through which a respective circuit tube passes. The engagement members may engage with the respective circuit tube to allow the circuit tube to be pulled and stretched for engagement with an occluder of the dialysis unit. For example, the circuit tubes of the blood circuit assembly may include silicone tubing that has to be stretched (and thereby reduced in diameter) to engage with an occluder. The circuit tube engagement members may resist the pull of an operator on the tubes, allowing the tubes to be stretched and placed in engagement with the occluder.

In another aspect of the invention, a method for replacing a blood circuit assembly of a dialysis unit includes grasping a pair of handles on an organizing tray of a blood circuit assembly that is mounted to a dialysis unit, disengaging locking tabs of the dialysis unit from the blood circuit assembly to free the blood circuit assembly from the dialysis unit, and pulling on the handles on the organizing tray of the blood circuit assembly to remove the blood circuit assembly from the dialysis unit. Disengagement of the locking tabs may be performed by flexing the locking tabs away from each other such that each locking tab is moved toward a nearest one of the handles. After removal of the blood circuit assembly, a replacement blood circuit assembly may be provided, openings in the organizing tray of the replacement blood circuit assembly may be aligned with the locking tabs so that each locking tab is received into a respective opening, and the organizing tray may be pushed relative to the dialysis unit such that the locking tabs engage with the replacement blood circuit assembly to mount the replacement blood circuit assembly to the dialysis unit. Mounting the replacement blood circuit assembly may also involve connecting control ports on the dialysis unit to mating ports on the assembly so that fluid control signals may be provided for pumps and valves of the blood circuit assembly. Other blood circuit connections may be made, such as inlet and outlet connections for the dialyzer, and the blood line connectors may be connected to receive dialysate into the blood circuit.

In another aspect of the invention, an air trap for a blood circuit in a dialysis unit includes a blood inlet supply line, a blood outlet supply line, and a container having an approximately spherical internal wall, an inlet at a top end of the container connected to the blood inlet supply line, and an outlet at a bottom end of the container connected to the blood outlet supply line. The inlet may be offset from a vertical axis of the approximately spherical internal wall such that blood entering the container through the inlet is directed to flow in around the approximately spherical wall in a spiral-like path. Such flow in the container may help to remove air bubbles from the blood as it flows from the inlet to the outlet, with any removed air remaining near the top of the container. The inlet port may be arranged to introduce blood into the container in a direction that is approximately tangential to the approximately spherical inner wall of the container and/or in a direction that is approximately perpendicular to the vertical axis of the container.

In one embodiment, a self-sealing port may be located at a top of the container, e.g., in the form of a split septum that is arranged to permit introduction of fluid into, and withdrawal of liquid from, the container by inserting a needleless device through the split septum. The self-sealing port may be arranged to be self-cleaning when disinfection liquid is circulated through the container, e.g., the port may be suitably exposed to flowing disinfection liquid to remove debris and/or heat material on the port to achieve desired disinfection.

In another aspect of the invention, a tube securing arrangement of a blood circuit assembly includes a organizing tray that supports components of a blood circuit assembly and includes a pair of tube engagement members each having a hole, a pair of patient inlet and outlet lines arranged to connect with patient access points for receiving liquid from and/or providing liquid to the patient, and a pair of stops on the patient inlet and outlet lines, respectively. The patient inlet and outlet lines may each pass through a hole of a respective tube engagement member so that the stop engages with the tube engagement member. With this arrangement, the tube engagement members may resist pulling and stretching of the inlet and outlet lines when engaging the lines with an occluder. The tube engagement members may be flexible to allow a user to press inwardly on the engagement member and seat the respective inlet or outlet line in the occluder, yet resist downward pulling of the line.

In another aspect of the invention, a hemodialysis system includes a dialyzer mount arranged to support a plurality of differently sized and/or shaped dialyzer units and to accommodate different distances between dialysate connections on the dialyzer units. The dialyzer mount, which may be located on a front panel of the dialysis unit, may include a pair of flange portions that are each arranged to engage with a respective dialysate quick-connect fitting connected to a dialysate port of the dialyzer. Each flange portion may be arranged to engage with a groove on the quick connect fitting that is located between a portion of the base of the quick connect fitting and a slide element of the quick connect fitting. For example, the dialyzer mount may include a pair of keyhole features with each keyhole feature having an upper insertion area sized to receive a portion of the base of the quick-connect fitting inserted into the upper insertion area, and a lower flanged portion having a width that is smaller than an overall a width of the base of the quick-connect fitting and that engages with a groove on the quick connect fitting. The lower flanged portion may include a pair of opposite flanges that engage with the groove and allow the quick-connect fitting to slide along the flanges.

In one embodiment, the bottom keyhole feature may include an adjustable support that is moveable in a vertical direction. For example, the adjustable support may be movable along the opposed flanges. Thus, the adjustable support may be fixable in a plurality of different positions on the flanges to support the weight of the dialyzer. In one arrangement, the adjustable support includes a "U" shaped member and at least one thumb screw that may be tightened to fix the "U" shaped member in place.

In another aspect of the invention, a blood line connector for a blood circuit of a hemodialysis unit may have the ability to make two different types of fluid tight connections, e.g., a screw-type connection with a luer connector at a patient access and a press-in type connection with a dialysate circuit of the hemodialysis unit. For example, the blood line connector may include a tube connection end arranged to sealingly engage with a blood circuit tube, and a patient access connection end with a frustoconical member having an internally threaded portion arranged to engage with an externally threaded patient access, and a pair of locking arms extending rearwardly from the frustoconical member. The locking arms may each have a finger depression portion and a barbed portion, and may be arranged to engage with a mating connector on the dialysis unit at the barbed portions to lock the frustoconical member in sealing engagement with the mating connector when making a press-in type connection. The barbed portions may disengage from the mating connector when the finger depression portions are urged toward each other. In one embodiment, the patient access connection end may include a central tube extending from the center of the frustoconical member. The internally threaded portion of the frustoconical member and the central tube may be arranged to mate with a female luer-type patient access connector or any other suitable screw-type connection.

In another aspect of the invention, a method for operating a dialysis unit includes connecting blood line connectors of arterial and venous blood lines for a dialysis unit to patient access connectors in communication with a patient blood system. In one embodiment, the patient access connectors may require a corresponding blood line connector to establish a threaded engagement with the patient access connector, thereby forming a luer or screw-type connection between the blood line connectors and the patient access connectors. The dialysis unit may be operated to withdraw blood from a patient access connector and into an arterial blood line, subject the withdrawn blood to a dialysis process to produce treated blood, and return the treated blood to the patient via the venous blood line and the other patient access connector. Thereafter, the blood line connectors may be disconnected from the patient access connectors by unscrewing the blood line connectors from a corresponding patient access connector, and the blood line connectors may be connected to a directing circuit of the dialysis unit. The blood line connectors may be connected to the directing circuit by a press-in connection with a corresponding connection point on the dialysis unit, e.g., by pushing the blood line connectors into the connection points to establish the press-in connection.

In another aspect of the invention, a reagent supply arrangement for a hemodialysis system may be arranged to provide two or more reagent materials for use in preparing a dialysate and may include a connector arranged to help prevent the connection of a reagent material to the wrong port. For example, the reagent supply may include an E-prong connector having three parallel prongs with two outer prongs arranged in a common plane and a center prong arranged above the common plane, a first supply line for a first reagent connected in fluid communication with one of the outer prongs, a second supply line for a second reagent connected in fluid communication with the other of the outer prongs, a liquid line connected in fluid communication with the center prong, and a container for housing the first reagent having an inlet connected to the liquid line and an outlet connected to the first supply line for the first reagent. The E-prong connector may help prevent the improper connection of the first and second supply lines to the dialysis unit, e.g., because the central prong being located out of the plane of the two outer prongs ensure connection of the E-prong connector in only one way to the dialysis unit.

In one embodiment, the container includes a bicarbonate material suitable for use in generating a dialysate for the hemodialysis system. The liquid line may be a water supply line that provides water to the container, allowing the water to mix with the bicarbonate (which may be in powder or other solid form) and flow to the first supply line. The second supply line may be an acid supply line that includes a connector and provides acid material to the E-prong connector. The reagent supply may also include an acid bag spike that is removably engaged with the connector of the acid supply line. The acid bag spike may include a spike member and a pair of spring clips at an end of the acid bag spike opposite the connector of the acid supply line, allowing the acid bag spike to be fluidly connected with an acid bag or other acid source.

In another aspect of the invention, a method for operating a hemodialysis system includes providing a dialysis unit having an enclosure containing suitable components for performing hemodialysis including a dialyzer, one or more pumps to circulate blood through the dialyzer, a source of dialysate, and one or more pumps to circulate the dialysate through the dialyzer. The enclosure may include a housing that supports the components and has a front panel at which blood circuit connections and dialysate fluidic connections are made. A reagent supply may be provided including an E-prong connector, a first supply line for a first reagent connected in fluid communication with one of the outer prongs, a second supply line for a second reagent connected in fluid communication with the other of the outer prongs, a liquid line connected in fluid communication with the center prong, and a container for housing the first reagent having an inlet connected to the liquid line and an outlet connected to the first supply line for the first reagent. The E-prong connector may be engaged with a connection point at the front panel of the dialysis unit, thereby allowing the dialysis unit to provide water to the liquid line of the reagent supply, and allowing the dialysis unit to receive the first and second reagents from the first and second supply lines.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF THE DRAWINGS

Aspects of the invention are described with reference to illustrative embodiments, which are described with reference to the drawings in which like numerals reference like elements, and wherein.

DETAILED DESCRIPTION

Figure 1:
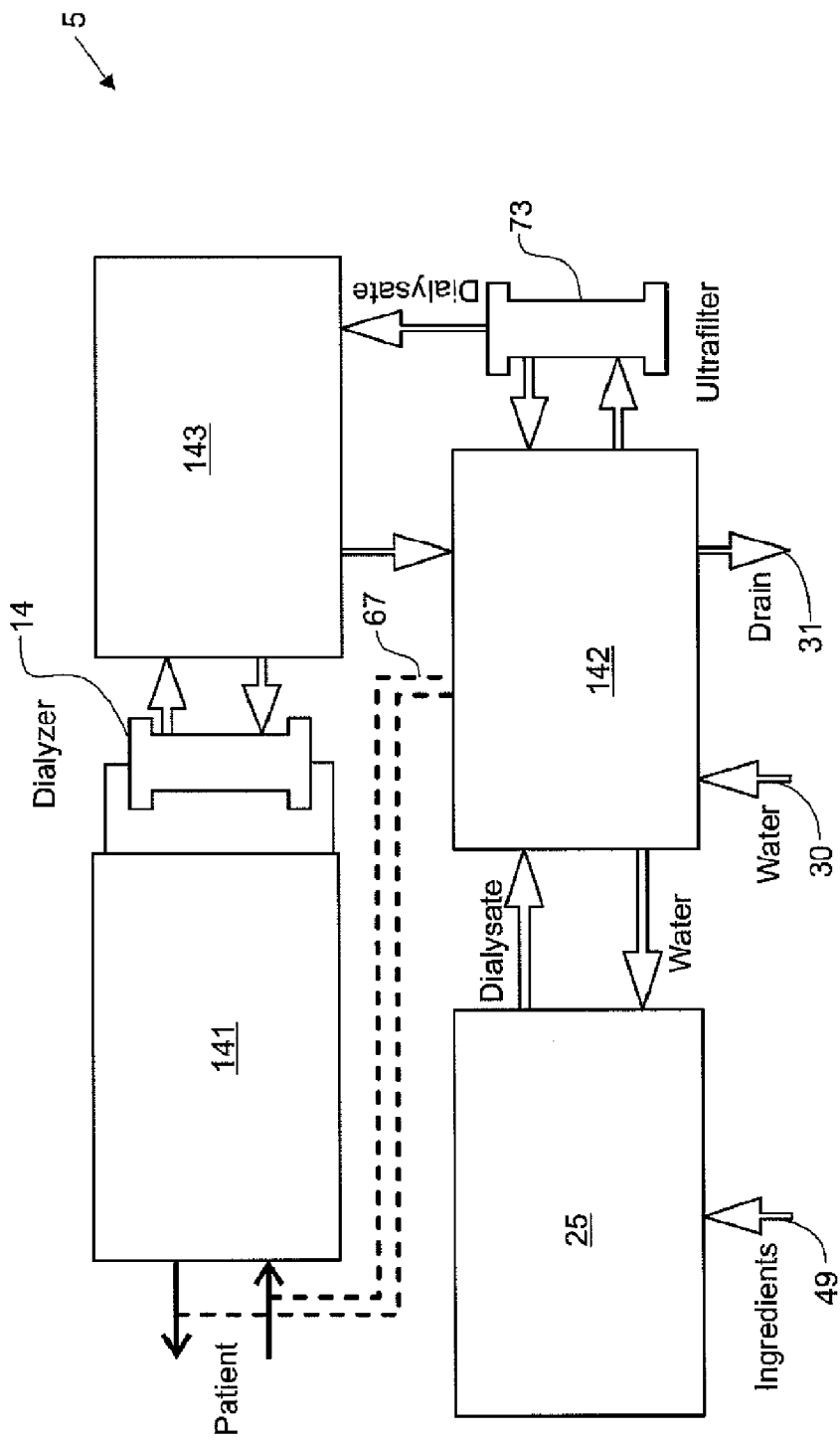
FIG. 1 is a schematic representation of fluid handling components of a hemodialysis system in an illustrative embodiment.

Various aspects of the invention are generally directed to new systems for hemodialysis and the like, such as hemofiltration systems, hemodiafiltration systems, plasmapheresis systems, etc. Accordingly, although the various systems and methods described herein are described in relation to hemodialysis, it should be understood that the various systems and method described herein are applicable to other dialysis systems and/or in any extracorporeal system able to treat blood or other bodily fluids, such as plasma.

As discussed below, a hemodialysis system typically includes a blood flow path and a dialysate flow path. It should be noted that within such flow paths, the flow of fluid is not necessarily linear, and there may be any number of "branches" within the flow path that a fluid can flow from an inlet of the flow path to an outlet of the flow path. Examples of such branching are discussed in detail below. In the blood flow path, blood is drawn from a patient, and is passed through a dialyzer, before being returned to the patient. The blood is treated by the dialyzer, and waste molecules (e.g., urea, creatinine, etc.) and water are passed from the blood, through a semi-permeable membrane in the dialyzer, into a dialysate solution that passes through the dialyzer by the dialysate flow path. In various embodiments, blood may be drawn from the patient from two lines (e.g., an arterial line and a venous line, i.e., "dual needle" flow), or in some cases, blood may be drawn from the patient and returned through the same or catheter needle (e.g., the two lines or lumens may both be present within the same needle, i.e., a form of "dual lumen" flow). In still other embodiments, a "Y" site or "T" site is used, where blood is drawn from the patient and returned to the patient through one patient connection having two branches (one being the fluid path for the drawn blood, the second the fluid path for the return blood, i.e., a form of "single needle" flow). The patient may be any subject in need of hemodialysis or similar treatments, including non-human subjects, such as dogs, cats, monkeys, and the like, as well as humans.

In the dialysate flow path, fresh dialysate is prepared and is passed through the dialyzer to treat the blood from the blood flow path. The dialysate may also be equalized for blood treatment within the dialyzer (i.e., the pressure between the dialysate and the blood are equalized), often exactly, or in some embodiments, at least within about 1% or about 2% of the pressure of the blood. In some cases, it may be desirable to maintain a greater pressure difference (either positive or negative) between the blood flow path and dialysate flow path. After passing through the dialyzer, the used dialysate, containing waste molecules (as discussed below), is discarded in some fashion. The dialysate in some cases may be re-circulated in a "multi-pass" arrangement, which may be beneficial in capturing larger molecules having low mobility across the dialyzer. In some cases, the dialysate is heated prior to treatment of the blood within the dialyzer using an appropriate heater, such as an electrical resistive heater. The dialysate may also be filtered to remove contaminants, infectious organisms, debris, and the like, for instance, using an ultrafilter. The ultrafilter may have a pore size chosen to prevent species such as these from passing therethrough. For instance, the pore size may be less than about 0.3 micrometers, less than about 0.2 micrometers, less than about 0.1 micrometers, or less than about 0.05 micrometers, etc. The dialysate is used to draw waste molecules (e.g., urea, creatinine, ions such as potassium, phosphate, etc.) and water from the blood into the dialysate through osmosis or convective transport, and dialysate solutions are well-known to those of ordinary skill in the art.

The dialysate typically contains various ions such as sodium, chloride, bicarbonate, potassium and calcium that are similar in concentration to that of normal blood. In some cases, the bicarbonate, may be at a concentration somewhat higher than found in normal blood. Typically, the dialysate is prepared by mixing water from a water supply with one or more ingredients: an "acid" (which may contain various species such as acetic acid, dextrose, NaCl, CaCl, KCl, MgCl, etc.), sodium bicarbonate ($NaHCO_3$), and/or sodium chloride (NaCl). The preparation of dialysate, including using the appropriate concentrations of salts, osmolarity, pH, and the like, is well-known to those of ordinary skill in the art. As discussed in detail below, the dialysate need not be prepared at the same rate that the dialysate is used to treat the blood. For instance, the dialysate can be made concurrently or prior to dialysis, and stored within a dialysate storage vessel or the like.

Within the dialyzer, the dialysate and the blood typically are separated by a semi-permeable membrane. Typically, the semipermeable membrane is formed from a polymer such as cellulose, polyarylethersulfone, polyamide, polyvinylpyrrolidone, polycarbonate, polyacrylonitrile, or the like, which allows the transport of ions or small molecules (e.g., urea, water, etc.), but does not allow bulk transport or convection during treatment of the blood. In some cases (such as high-flux dialyzers), even larger molecules, such as beta-2-microglobulin, may pass through the membrane. In some cases, for example, ions and molecules may pass through the dialyzer by convective flow if a hydrostatic pressure difference exists across the semi-permeable membrane.

It should be noted that, as used herein, "fluid" means anything having fluidic properties, including but not limited to, gases such as air, and liquids such as water, aqueous solution, blood, dialysate, etc.

FIG. 1 shows a schematic block diagram of fluid circuitry for a hemodialysis system that incorporates various aspects of the invention. In this illustrative embodiment, the dialysis system 5 includes a blood flow circuit 141 that draws blood from a patient, passes the blood through a dialyzer 14, and returns the treated blood to the patient. A balancing circuit or an internal dialysate circuit 143 receives dialysate from an ultrafilter 73, passes the dialysate through the dialyzer 14, and receives used dialysate from the dialyzer 14. A directing circuit or an external dialysate circuit 142 provides fresh dialysate to the ultrafilter 73, and receives used dialysate from the internal dialysate circuit 143 (which may be directed to a drain 31). The directing circuit 142 can also receive water from a water supply 30 and pass it to a mixing circuit 25. The mixing circuit 25 forms dialysate using water from the directing circuit 142 and reagent ingredients 49, such as citric acid, salt and a bicarbonate, that may be received from a renewable source. The mixing circuit 25 may prepare dialysate, for example, on an as-needed basis, during and/or in advance of dialysis. New dialysate prepared by the mixing circuit 25 may be provided to the directing circuit 142, which may provide the dialysate to the ultrafilter 73, as described above. The directing circuit 142 may include a heater to heat the dialysate to a suitable temperature and/or to heat fluid in the system for disinfection. Conduits 67 (shown in dotted line) may be connected between the blood flow circuit 141 and the directing circuit 142, e.g., for disinfection of the hemodialysis system.

Figure 2:
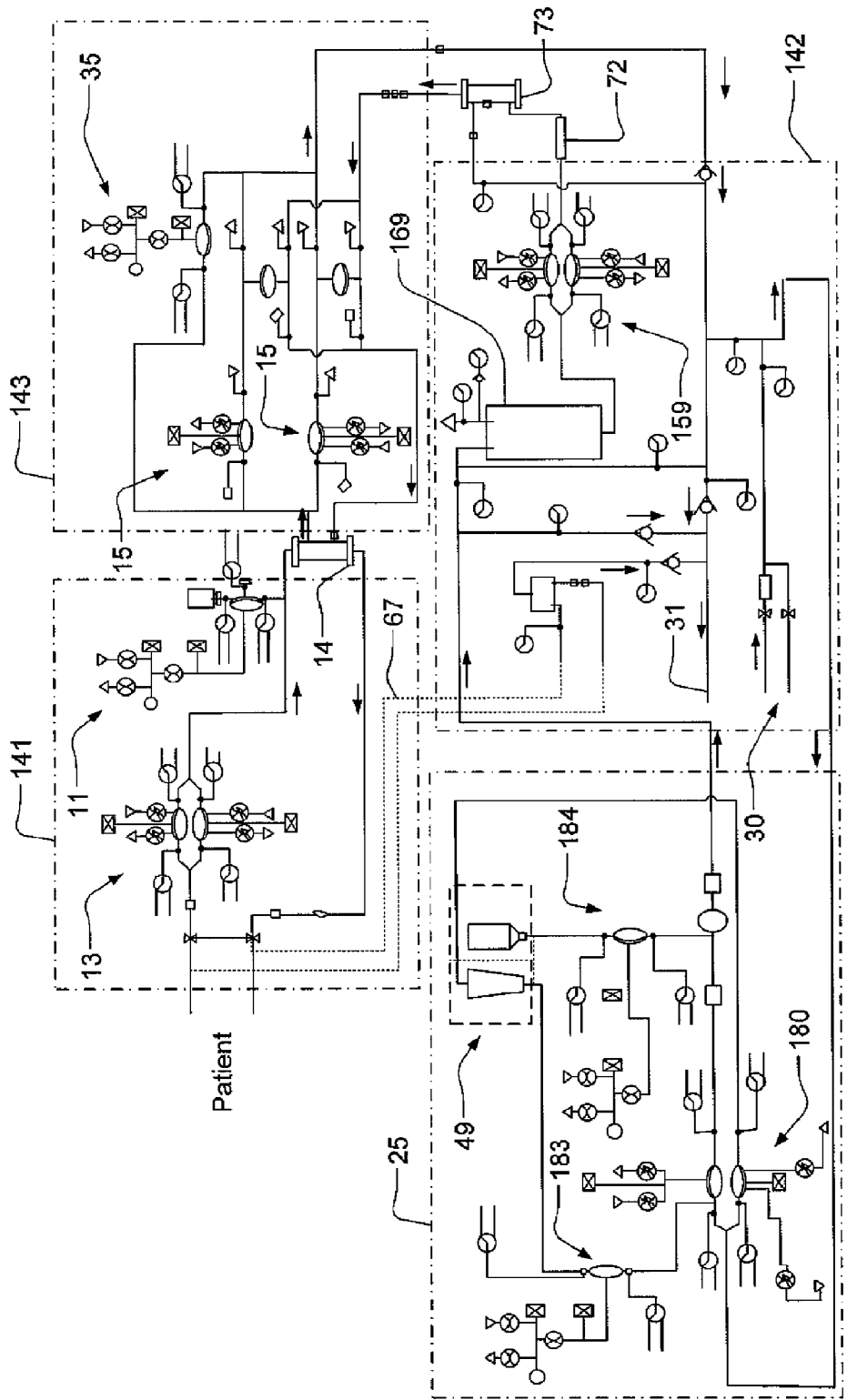
FIG. 2 shows a schematic fluid flow diagram for the dialysis system of FIG. 1.

FIG. 2 is a schematic diagram showing a more detailed circuit arrangement for the dialysis system 5 shown in FIG. 1. It should be understood, of course, that FIG. 2 is only one possible embodiment of the general hemodialysis system of FIG. 1, and in other embodiments, other fluid circuits, modules, flow paths, layouts, etc. are possible. Examples of such systems are discussed in more detail below, and also can be found in the following, each of which is incorporated herein by reference: U.S. application Ser. No. 12/072,908, filed Feb. 27, 2008, U.S. Provisional Application 60/903,582, filed Feb. 27, 2007, U.S. Provisional Application 60/904,024, filed Feb. 27, 2007, U.S. Patent application Ser. No. 11/871,680, filed Oct. 12, 2007 and published as U.S. Patent Application Publication No. 2008/0208103 on Aug. 28, 2008, U.S. patent application Ser. No. 11/871,712, filed Oct. 12, 2007, U.S. patent application 11/871,787, filed Oct. 12, 2007 and published as U.S. Patent Application Publication No. 2008/0253911 on Oct. 16, 2008, U.S. patent application 11/871,793, filed Oct. 12, 2007 and published as U.S. Patent Application Publication No. 2008/0253912 on Oct. 16, 2008, or U.S. patent application Ser. No. 11/871,803, filed Oct. 12, 2007 and published as U.S. Patent Application Publication No. 2008/0202591 on Aug. 28, 2008.

The blood flow circuit 141 includes an anticoagulant supply 11 and a blood flow pump 13 which pumps blood from a patient through a dialyzer 14 and returns the blood to the patient. The anticoagulant supply 11, although shown in the path of blood flowing towards the dialyzer, may be instead located in another suitable location. e.g., any location upstream or downstream from blood flow pump 13. The balancing circuit 143 includes two dialysate pumps 15, which pump dialysate into the dialyzer 14, and a bypass pump 35. The flow of blood through the blood flow circuit 141 in some cases, is synchronized with the flow of dialysate in the dialysate flow path. In an embodiment, the flow of dialysate into and out of the dialyzer 14 and the balancing circuit 143 is balanced volumewise using balancing chambers in the balancing circuit 143. The directing circuit 142 includes a dialysate pump 159, which pumps dialysate from a dialysate tank 169 through a heater 72 and/or the ultrafilter 73 to the balancing circuit 143. The directing circuit 142 also receives waste fluid from balancing circuit 143 and directs it to a drain 31. In some cases, the blood flow circuit 141 can be connected via conduits 67 to the directing circuit 142, e.g., for disinfection, as discussed below. Dialysate in the dialysate tank 169 is provided by the mixing circuit 25, which produces the dialysate using water from a water supply 30 provided via the directing circuit 142 and dialysate ingredients 49 (e.g., bicarbonate and acid). A series of mixing pumps 180, 183, 184 are used to mix the various components and produce the dialysate.

Figure 3:
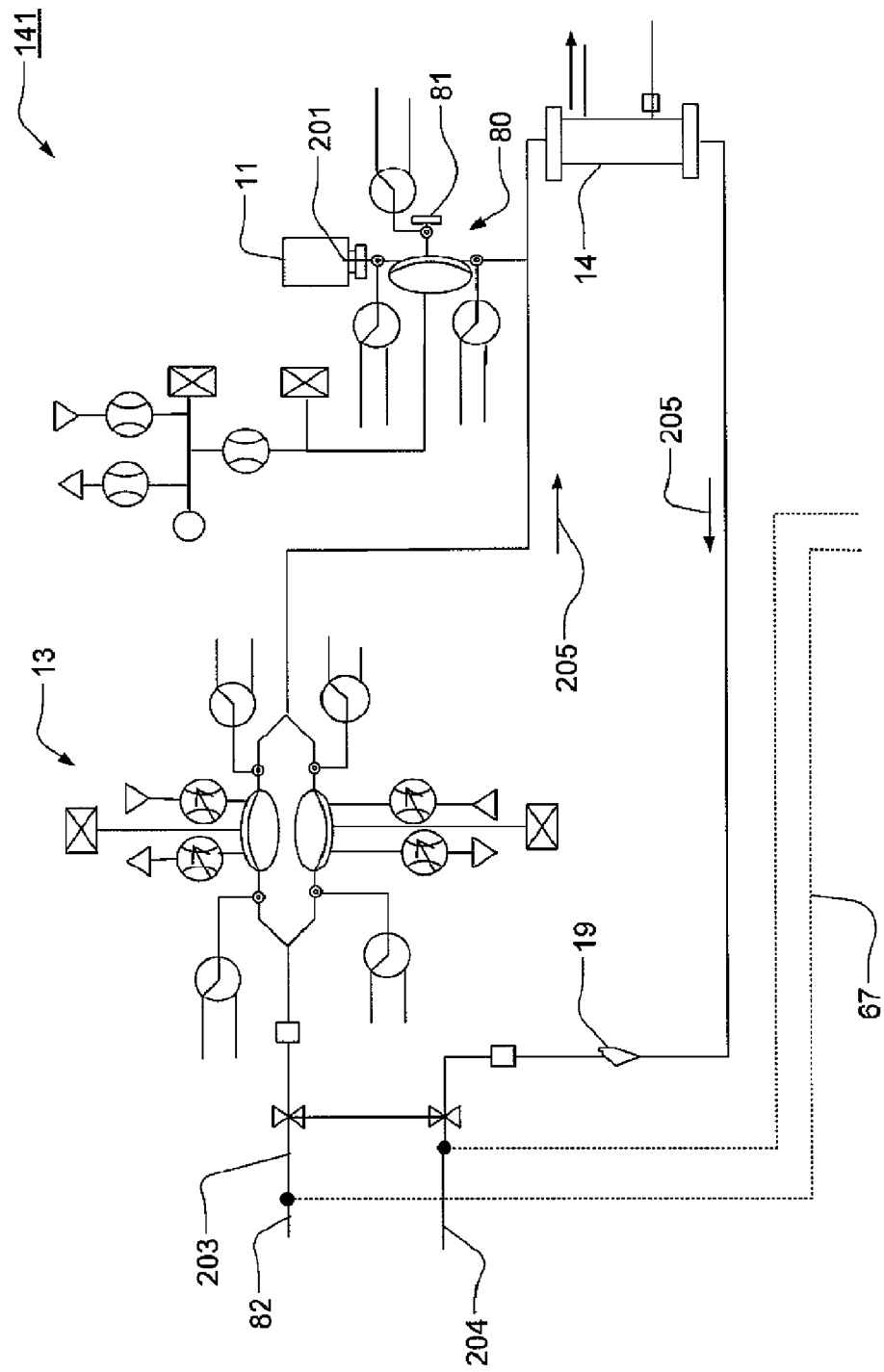
FIG. 3 is a schematic fluid flow diagram for the blood flow circuit of the FIG. 2 embodiment.

FIG. 3 shows a close-up view of the blood flow circuit 141 in this illustrative embodiment. Under normal operation, blood flows from a patient through arterial line 203 via blood flow pump 13 to the dialyzer 14 (the direction of flow during normal dialysis is indicated by arrows 205; in some modes of operation, however, the flow may be in different directions, as discussed below). Optionally, an anticoagulant may be introduced into the blood via anticoagulant pump 80 from an anticoagulant supply. After passing through dialyzer 14 and undergoing dialysis, the blood returns to the patient through venous line 204, optionally passing through an air trap and/or a blood sample port 19. The pump 13 may include, for instance, pumps 23 that are actuated by a control fluid.

For example, in one embodiment, the blood flow pump 13 may comprise two (or more) pod pumps 23. Each pod pump, in this particular example, may include a rigid chamber with a flexible diaphragm or membrane dividing each chamber into a pumping compartment and control compartment. There may be four entry/exit valves for these compartments, two for the pumping compartment and two for the control compartment. The valves for the control compartment of the chambers may be two-way proportional valves, one connected to a first control fluid source (e.g., a high pressure air source), and the other connected to a second control fluid source (e.g., a low pressure air source) or a vacuum source. The fluid valves can be opened and closed to direct fluid flow when the pod pumps 23 are operating. Non-limiting examples of pod pumps are described in U.S. Provisional Application 60/792,073, filed Apr. 14, 2006, or in U.S. patent application Ser. No. 11/787,212, filed Apr. 13, 2007 and published as U.S. Patent Application Publication No. 2008/0175719 on Jul. 24, 2008, each incorporated herein by reference. If more than one pod pump is present, the pod pumps may be operated in any suitable fashion, e.g., synchronously, asynchronously, in-phase, out-of-phase, etc. For instance, in some embodiments, the two-pump pumps can be cycled out of phase to affect the pumping cycle, e.g., one pump chamber fills while the second pump chamber empties. A phase relationship anywhere between 0° (the pod pumps fill and empty in unison) and 180° (one pod pump fills as the other empties) can be selected in order to impart any desired pumping cycle. A phase relationship of 180° may yield continuous flow into and out of the set of pod pumps. This is useful, for instance, when continuous flow is desired, e.g., for use with dual needle or dual lumen catheter flow. Setting a phase relationship of 0°, however, may be useful in some cases for single needle/single lumen flow or in other cases. In a 0° relationship, the pod pumps will first fill from the needle, then deliver blood through the blood flow path and back to the patient using the same needle. In addition, running at phases between 0° and 180° can be used in some cases, to achieve a push/pull relationship (hemodiafiltration or continuous back flush) across the dialyzer.

An anticoagulant (e.g., heparin, or any other suitable anticoagulant) may be contained within a vial 11 (or other anticoagulant supply, such as a tube or a bag), and blood flow circuit 141 may include a spike 201 (which, in one embodiment, is a needle) that can pierce the seal of the vial. The spike 201 may be formed from plastic, stainless steel, or another suitable material, and may be a sterilizable material in some cases, e.g., the material may be able to withstand sufficiently high temperatures and/or radiation so as to sterilize the material.

An anticoagulant pump 80, which can act as a metering chamber in some cases, can be used to control the flow of anticoagulant into the blood circuit. The anticoagulant pump 80 may be a pod pump or a membrane-based metering pump, and/or may be actuated by a control fluid, such as air. For example, the anticoagulant pump 80 may include a rigid chamber with a flexible diaphragm dividing the chamber into a pumping compartment and a control compartment. One valve for the control compartment of the chamber may be connected to a first control fluid source (e.g., a high pressure air source), and the other valve connected to a second control fluid source (e.g., a low pressure air source) or a vacuum source. Valves for the pumping compartment of the chamber can be opened and closed in coordination with the control compartment, thus controlling the flow of anticoagulant into the blood. In one set of embodiments, air provided through a filter 81 may also be introduced into the blood flow path by the anticoagulant pump 80, e.g., to provide air into the vial 11 after or before anticoagulant is withdrawn from the vial.

Fluid Management System ("FMS") measurements may be used to measure the volume of fluid pumped through a pump chamber during a stroke of the membrane, or to detect air in the pumping chamber. FMS methods are described in U.S. Pat. Nos. 4,808,161; 4,826,482; 4,976,162; 5,088,515; and 5,350,357, which are hereby incorporated herein by reference in their entireties. In one illustrative embodiment, the volume of liquid delivered by an anticoagulant pump, a dialysate pump, or other membrane-based fluid pump is determined using an FMS algorithm in which changes in chamber pressure are used to calculate a volume measurement at the end of a fill stroke and at the end of a delivery stroke. The difference between the computed volumes at the end of fill and delivery strokes may be used to determine the actual stroke volume. This actual stroke volume can be compared to an expected stroke volume for the particular sized chamber. If the actual and expected volumes are significantly different, the stroke has not properly completed and an error message can be generated.

The blood flow circuit 141 may also include an air trap 19 to remove air bubbles that may be present within the blood flow path. In some cases, the air trap 19 is able to separate any air that may be present from the blood due to gravity, and/or may include a port for sampling blood.

Figure 4:
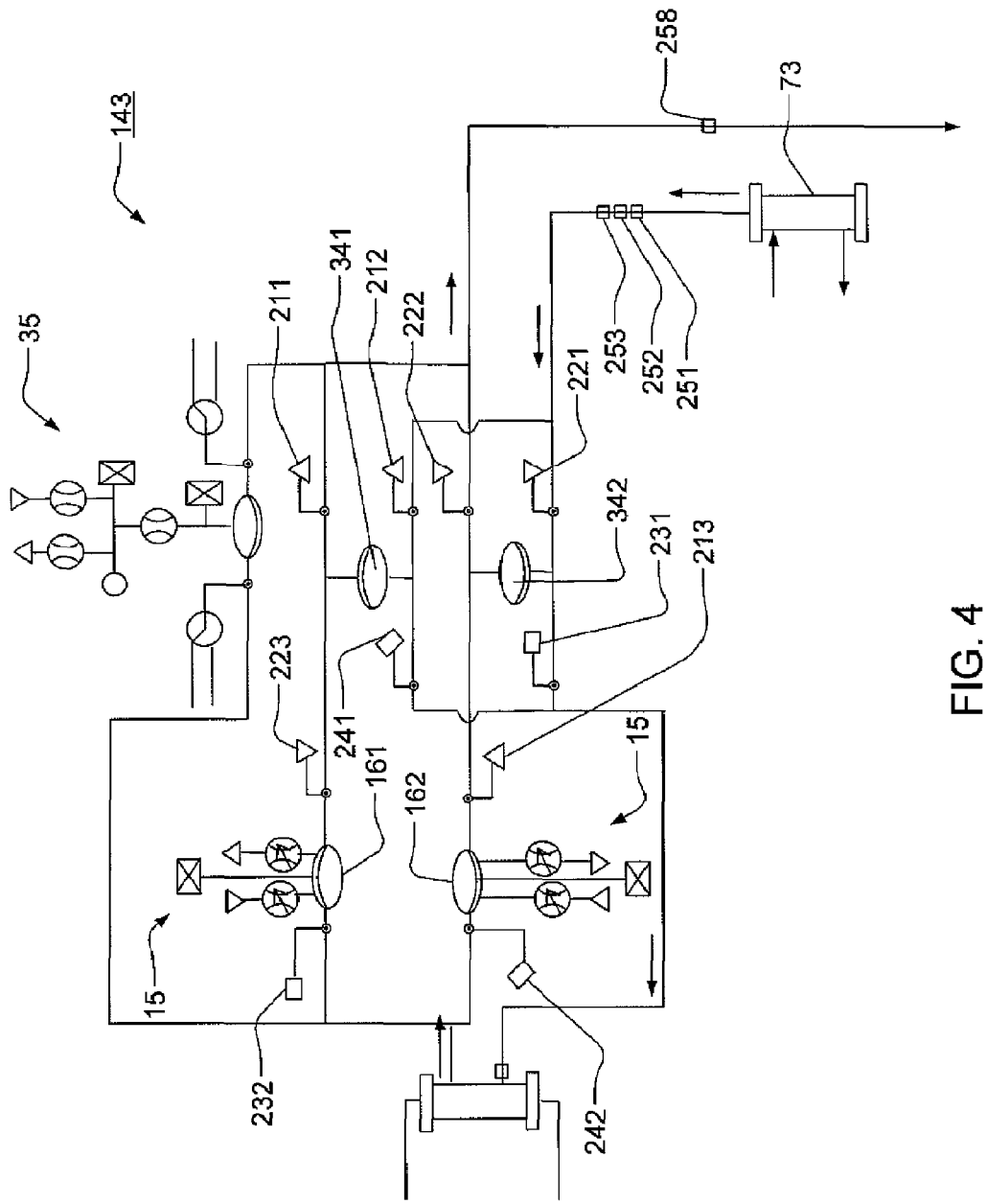
FIG. 4 is a schematic fluid flow diagram for the balancing circuit of the FIG. 2 embodiment.

FIG. 4 shows a close-up view of the balancing circuit 143 in the FIG. 2 embodiment. In the balancing circuit 143, dialysate flows from the optional ultrafilter 73 into a dialysate pump 15. In this embodiment, the dialysate pump 15 includes two pod pumps 161, 162, two balancing chambers 341, 342, and a pump 35 for bypassing the balancing chambers 341, 342. The balancing chambers 341, 342 may be constructed such that they are formed from a rigid chamber with a flexible diaphragm dividing the chamber into two separate fluid compartments, so that entry of fluid into one compartment can be used to force fluid out of the other compartment and vice versa. Non-limiting examples of pumps that can be used as pod pumps and/or balancing chambers are described in U.S. Provisional Application 60/792,073, filed Apr. 14, 2006, or in U.S. patent application Ser. No. 11/787,212, filed Apr. 13, 2007 and published as U.S. Patent Application Publication No. 2008/0175719 on Jul. 24, 2008.

In one embodiment, balancing of flow in the internal dialysate circuit works as follows. A set of pneumatically operated valves 211, 212, 213, 241, 242 has its operation synchronized and controlled together, where valves 211, 212, 213 are ganged and valves 241 and 242 are ganged, and a second set of pneumatically operated valves 221, 222, 223, 231, 232 similarly have its operation synchronized and controlled together, where valves 221, 222, 223 are ganged, and valves 231 and 232 are ganged. At a first point of time, the first set of valves 211, 212, 213, 241, 242 is opened while the second set of valves 221, 222, 223, 231, 232 is closed. Fresh dialysate flows into balancing chamber 341 while used dialysate flows from dialyzer 14 into pod pump 161. Fresh dialysate does not flow into balancing chamber 342 since valve 221 is closed. As fresh dialysate flows into balancing chamber 341, used dialysate within balancing chamber 341 is forced out and exits balancing circuit 143 (the used dialysate cannot enter pod pump 161 since valve 223 is closed). Simultaneously, pod pump 162 forces used dialysate present within the pod pump into balancing chamber 342 (through valve 213, which is open; valves 242 and 222 are closed, ensuring that the used dialysate flows into balancing chamber 342). This causes fresh dialysate contained within balancing chamber 342 to exit the balancing circuit 143 into dialyzer 14. Also, pod pump 161 draws in used dialysate from dialyzer 14 into pod pump 161.

Once pod pump 161 and balancing chamber 341 have filled with dialysate, the first set of valves 211, 212, 213, 241, 242 is closed and the second set of valves 221, 222, 223, 231, 232 is opened. Fresh dialysate flows into balancing chamber 342 instead of balancing chamber 341, as valve 212 is closed while valve 221 is now open. As fresh dialysate flows into balancing chamber 342, used dialysate within the chamber is forced out and exits balancing circuit, since valve 213 is now closed. Also, pod pump 162 now draws used dialysate from the dialyzer into the pod pump, while used dialysate is prevented from flowing into pod pump 161 as valve 232 is now closed and valve 222 is now open. Pod pump 161 forces used dialysate contained within the pod pump (from the previous step) into balancing chamber 341, since valves 232 and 211 are closed and valve 223 is open. This causes fresh dialysate contained within balancing chamber 341 to be directed into the dialyzer 14 (since valve 241 is now open while valve 212 is now closed). At the end of this step, pod pump 162 and balancing chamber 342 have filled with dialysate. This puts the state of the system back into the configuration at the beginning of this description, and the cycle is thus able to repeat, ensuring a constant flow of dialysate to and from the dialyzer 14. In an embodiment, the fluid (e.g. pneumatic) pressures on the control side of the balancing chamber valves are monitored to ensure they are functioning (e.g., opening and closing) properly.

As a specific example, a vacuum (e.g., 4 p.s.i. of vacuum) can be applied to the port for the first set of valves, causing those valves to open, while positive pressure (e.g., 20 p.s.i. of air pressure) is applied to the second set of valves, causing those valves to close (or vice versa). The pod pumps each urge dialysate into one of the volumes in one of the balancing chambers 341, 342. By forcing dialysate into a volume of a balancing chamber, an equal amount of dialysate is squeezed by the diaphragm out of the other volume in the balancing chamber. In each balancing chamber, one volume is occupied by fresh dialysate heading towards the dialyzer and the other volume is occupied by used dialysate heading from the dialyzer. Thus, the volumes of dialysate entering and leaving the dialyzer are kept substantially equal.

The bypass pump 35 can direct the flow of dialysate from the dialyzer 14 through balancing circuit 143 without passing through either of pod pumps 161 or 162. In this embodiment, the bypass pump 35 is a pod pump, similar to those described above, with a rigid chamber and a flexible diaphragm dividing each chamber into a fluid compartment and a control compartment. This pump may be the same or different from the other pod pumps and/or metering pumps described above. When control fluid is used to actuate the bypass pump 35, the additional drop in pressure on the exiting (spent) dialysate side of the dialyzer causes additional ultrafiltration of fluid from the blood in the dialyzer. This may cause a net efflux of fluid from the patient's blood, through the dialyzer, and ultimately to drain. Such a bypass may be useful, for example, in reducing the amount of fluid a patient has, which is often increased due to the patient's inability to excrete excess fluid (primarily water) through the kidneys. As shown in FIG. 4, the bypass pump 35 may be controlled by a control fluid (e.g., air), irrespective of the operation of pod pumps 161 and 162. This configuration may allow for easier control of net fluid removal from a patient, without having to operate the inside dialysate pumps either out of balance or out of phase with the blood pumps in order to achieve such fluid withdrawal from the patient.

To achieve balanced flow across the dialyzer, the blood flow pump, the pumps of the balancing circuit, and the pumps of the directing circuit (discussed below) may be operated to work together to ensure that flow into the dialyzer is generally equal to flow out of the dialyzer. If ultrafiltration is required, the ultrafiltration pump (if one is present) may be run independently of some or all of the other blood and/or dialysate pumps to achieve the desired ultrafiltration rate.

To prevent outgassing of the dialysate, the pumps of the balancing circuit may be kept at pressures above atmospheric pressure. In contrast, however, the blood flow pump and the directing circuit pumps use pressures below atmosphere to pull the diaphragm towards the chamber wall to complete a fill stroke. Because of the potential of fluid transfer across the semi-permeable membrane of the dialyzer and because the pumps of the balancing circuit run at positive pressures, the balancing circuit pumps may be able to use information from the blood flow pump(s) in order to synchronize the delivery strokes of the balancing circuit chambers to the dialyzer with the delivery strokes of the blood pumps.

In one set of embodiments, when running in such a balanced mode, if there is no delivery pressure from the blood flow pump, the balancing circuit pump diaphragm will push fluid across the dialyzer into the blood and the alternate pod of the balancing circuit will not completely fill. For this reason, the blood flow pump reports when it is actively delivering a stroke. When the blood flow pump is delivering a stroke the inside dialysate pump operates. When the blood flow pump is not delivering blood, the valves that control the flow from the dialyzer to the inside dialysate pumps (and other balancing valves ganged together with these valves, as previously discussed) may be closed to prevent any fluid transfer from occurring from the dialysate side to the blood side. During the time the blood flow pump is not delivering, the inside dialysate pumps are effectively frozen, and the inside dialysate pump delivery stroke resumes once the blood flow pump starts delivering again. The inside dialysate pump fill pressure can be set to a minimal positive value to ensure that the pump operates above atmosphere at minimal impedance. Also, the inside dialysate pump delivery pressure can be set to the blood flow pump pressure to generally match pressures on either side of the dialyzer, minimizing flow across the dialyzer during delivery strokes of the inside dialysate pump.

In another embodiment, the inside dialysate pump delivers dialysate to the dialyzer at a pressure slightly above the pressure at which blood is delivered to the dialyzer. This ensures that a full balance chamber of clean dialysate gets delivered to the dialyzer. On the return side, the inside dialysate pump can fill with spent dialysate from the dialyzer at a slightly lower pressure than the outlet pressure on the blood side of the dialyzer, ensuring that the receiving dialysate pump chamber can fill. This in turn ensures that there is enough dialysate available to complete a full stroke in the balancing chamber. Flows across the semi-permeable membrane caused by these differential pressures will tend to cancel each other; and the pumping algorithm otherwise attempts to match the average pressures on the dialysate and blood sides of the dialyzer.

It is generally beneficial to keep the blood flow as continuous as possible during therapy, as stagnant blood flow can result in blood clots. In addition, when the delivery flow rate on the blood flow pump is discontinuous, the balancing pump may pause its stroke more frequently, which can result in discontinuous and/or low dialysate flow rates. However, the flow through the blood flow pump can be discontinuous for various reasons. For instance, pressure may be limited within the blood flow pump, e.g., to +600 mmHg and/or −350 mmHg to provide safe pumping pressures for the patient. For instance, during dual needle flow, the two pod pumps of the blood flow pump can be programmed to run 180° out of phase with one another. If there were no limits on pressure, this phasing could always be achieved. However to provide safe blood flow for the patient these pressures are limited. If the impedance is high on the fill stroke (due to a small needle, very viscous blood, poor patient access, etc.), the negative pressure limit may be reached and the fill flow rate will be slower then the desired fill flow rate. Thus the delivery stroke must wait for the previous fill stroke to finish, resulting in a pause in the delivery flow rate of the blood flow pump. Similarly, during single needle flow, the blood flow pump may be run at 0° phase, where the two blood flow pump pod pumps are simultaneously emptied and filled. When both pod pumps are filled, the volumes of the two pod pumps are delivered. In an embodiment, the sequence of activation causes a first pod pump and then a second pod pump to fill, followed by the first pod pump emptying and then the second pod pump emptying. Thus the flow in single needle or single lumen arrangement may be discontinuous.

One method to control the pressure saturation limits would be to limit the desired flow rate to the slowest of the fill and deliver strokes. Although this would result in slower blood delivery flow rates, the flow rate would still be known and would be more continuous, which would allow for more accurate and continuous dialysate flow rates. Another method to make the blood flow rate more continuous in single needle operation would be to use maximum pressures to fill the pods so the fill time would be minimized. The desired deliver time could then be set to be the total desired stroke time minus the time that the fill stroke took. However, the less continuous the blood flow, the more the dialysate flow rate may have to be adjusted upward during blood delivery to the dialyzer to make up for the time that the dialysate pump is stopped when the blood flow pump is filling. If this is done with the correct timing, an average dialysate flow rate taken over several strokes can still match the desired dialysate flow rate.

Figure 5:
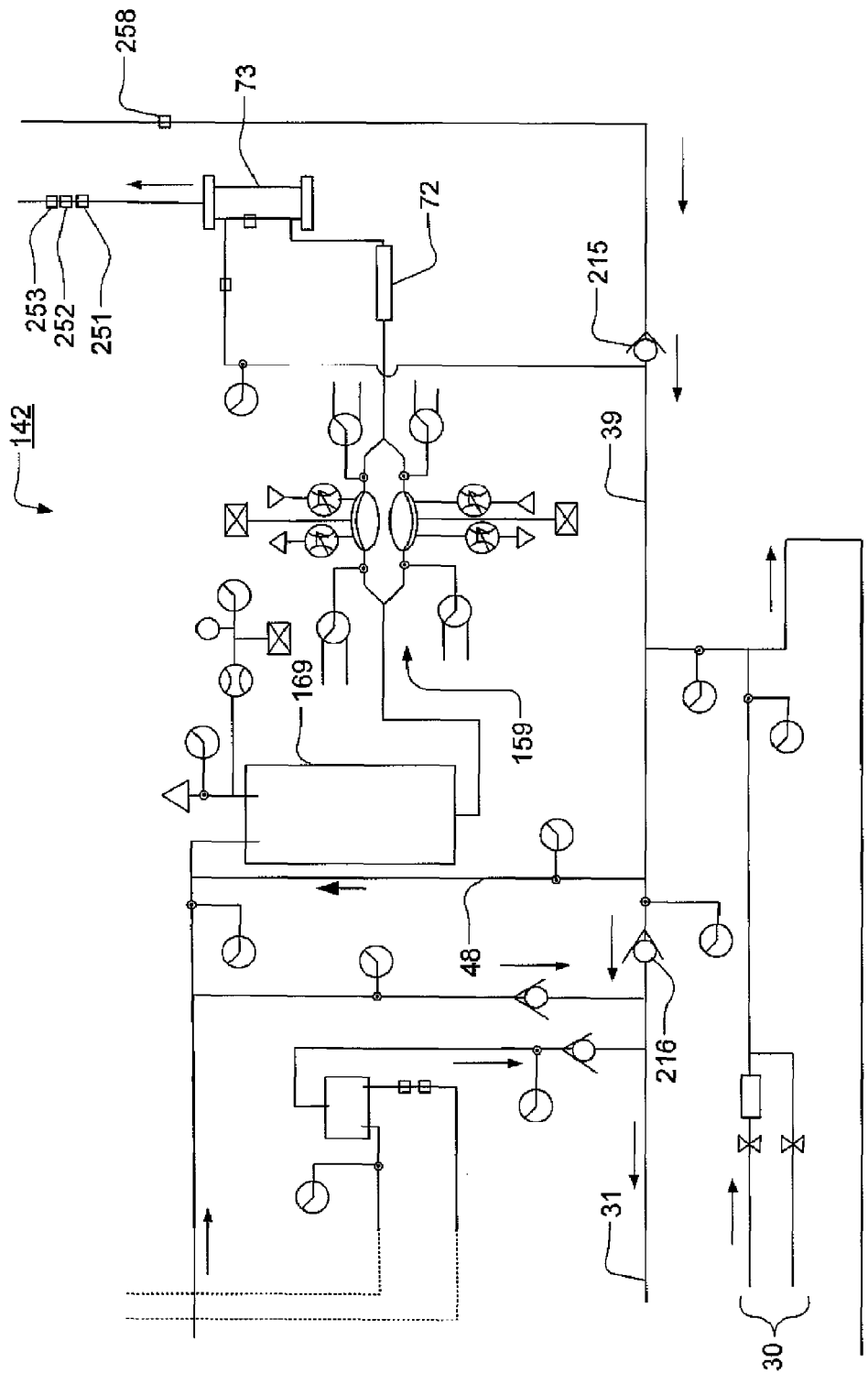
FIG. 5 is a schematic fluid flow diagram for the directing circuit of the FIG. 2 embodiment.

FIG. 5 shows a close up of the directing circuit 142 in the FIG. 2 embodiment. In this embodiment, the directing circuit 142 can provide dialysate from a dialysate tank 169 via a dialysate pump 159 to a heater 72 and the ultrafilter 73. The heater 72 may be used to warm the dialysate to body temperature, and/or a temperature such that the blood in the blood flow circuit is heated by the dialysate, and the blood returning to the patient is at body temperature or higher. In some cases, the heater 72 may be connected to a control system such that dialysate that is incorrectly heated (i.e., the dialysate is too hot or too cold) may be recycled (e.g., back to the dialysate tank 169) or sent to drain instead of being passed to the dialyzer. The heater 72 may also be used, in some embodiments, for disinfection or sterilization purposes. For instance, water may be passed through the hemodialysis system and heated using the heater such that the water is heated to a temperature able to cause disinfection or sterilization to occur, e.g., temperatures of at least about 70° C., at least about 80° C., at least about 90° C., at least about 100° C., at least about 110° C., etc.

The flow of dialysate through the directing circuit 142 may be controlled (at least in part) by operation of the dialysate pump 159. In addition, the dialysate pump 159 may control flow through the balancing circuit 143. For instance, as discussed above, fresh dialysate from the directing circuit 142 flows into balancing chambers 341 and 342 of balancing circuit 143. The dialysate pump 159 may be used as a driving force to cause the fresh dialysate to flow into these balancing chambers. In one set of embodiments, dialysate pump 159 includes a pod pump, e.g., similar to those described above.

The dialysate may also be filtered to remove contaminants, infectious organisms, pathogens, pyrogens, debris, and the like, for instance, using an ultrafilter 73. The ultrafilter 73 may be positioned in any suitable location in the dialysate flow path, for instance, between the directing circuit and the balancing circuit, e.g., as shown, and/or the ultrafilter 73 may be incorporated into the directing circuit or the balancing circuit. If an ultrafilter is used, its pore size may be chosen to prevent species such as these from passing through the filter.

In some cases, the ultrafilter 73 may be operated such that waste from the filter (e.g., the retentate stream) is passed to a waste stream, such as waste line 39 in FIG. 5.

In some cases, the ultrafilter 73 may be operated such that waste from the filter (e.g., the retentate stream) is passed to a waste stream, such as waste line 39 in FIG. 5. In some cases, the amount of dialysate flowing into the retentate stream may be controlled. For instance, if the retentate is too cold (i.e., heater 72 is not working, or heater 72 is not heating the dialysate to a sufficient temperature, the entire dialysate stream (or at least a portion of the dialysate) may be diverted to waste line 39, and optionally, recycled to dialysate tank 169 using line 48. Flow from the filter 73 may also be monitored for several reasons, e.g., using temperature sensors (e.g., sensors 251 and 252), conductivity sensors (for confirming dialysate concentration, e.g., sensor 253), or the like. An example of such sensors is discussed below; further non-limiting examples can be seen in a U.S. patent application Ser. No. 12/038,474, filed Feb. 27, 2008 and published as U.S. Patent Application Publication No. 2008/0253427 on Oct. 16 2008.

The ultrafilter and the dialyzer may provide redundant screening methods for the removal of contaminants, infectious organisms, pathogens, pyrogens, debris, and the like. Accordingly, any contaminant would have to pass through both the ultrafilter and the dialyzer before reaching a patient's blood. Even in the event that either the ultrafilter or dialyzer integrity fails, the other may still be able to maintain dialysate sterility and prevent contaminants from reaching the patient's blood.

The directing circuit 142 may also be able to route used dialysate coming from a balancing circuit to a drain, e.g., through waste line 39 to drain 31. The drain may be, for example, a municipal drain or a separate container for containing the waste (e.g., used dialysate) to be properly disposed of. In some cases, one or more check or "one-way" valves (e.g., check valves 215 and 216) may be used to control flow of waste from the directing circuit 142 and from the system 5. Also, in certain instances, a blood leak sensor (e.g., sensor 258) may be used to determine if blood is leaking through the dialyzer 14 into the dialysate flow path. In addition, a liquid sensor can be positioned in a collection pan at the bottom of the hemodialysis unit to indicate leakage of either blood or dialysate, or both, from any of the fluid circuits.

The directing circuit 142 may receive water from a water supply 30, e.g., from a container of water such as a bag, and/or from a device able to produce water, e.g., a reverse osmosis device. In some cases, the water entering the system is set at a certain purity, e.g., having ion concentrations below certain values. The water entering into the directing circuit 142 may be passed on to various locations, e.g., to a mixing circuit 25 for producing fresh dialysate and/or to waste line 39. In some cases, valves to the drain 31 and various recycle lines are opened, and conduits 67 may be connected between directing circuit 142 and blood flow circuit 141, such that water is able to flow continuously around the system. If heater 72 is also activated, the water passing through the system will be continuously heated, e.g., to a temperature sufficient to disinfect the system.

Figure 6:
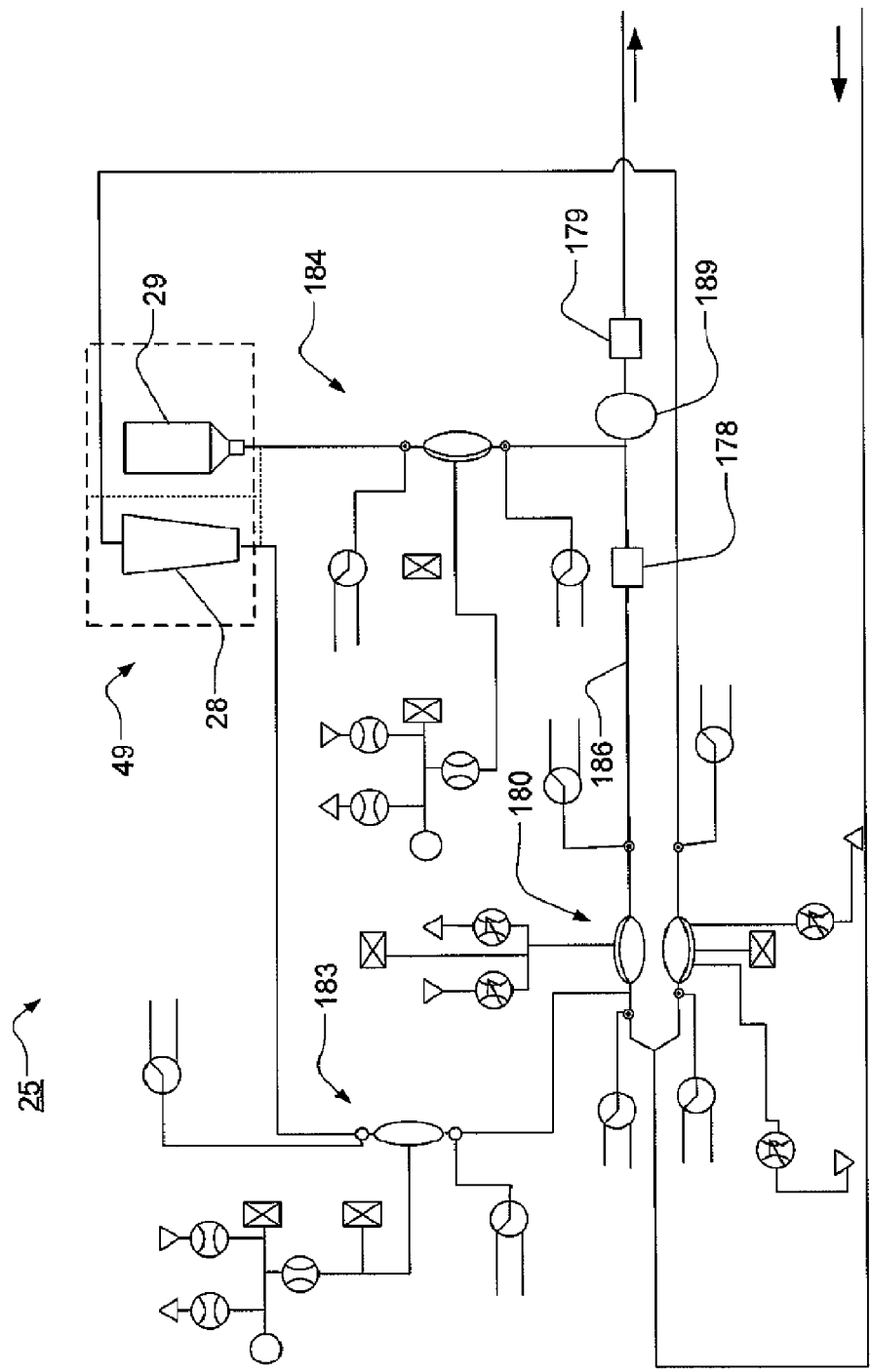
FIG. 6 is a schematic fluid flow diagram for the mixing circuit of the FIG. 2 embodiment.

FIG. 6 shows a close-up view of the mixing circuit 25 in the illustrative embodiment of FIG. 2. Water from the directing circuit 142 flows into the mixing circuit due to action of a pump 180. In this embodiment, the pump 180 includes one or more pod pumps, similar to those described above. In some cases, a portion of the water is directed to reagent ingredients 49, e.g., for use in transporting the ingredients, such as the bicarbonate 28, through the mixing circuit 25. In some cases, sodium chloride and/or the sodium bicarbonate 28 may be provided in a powdered or granular form, which is mixed with water provided by the pump 180. Bicarbonate from bicarbonate source 28 is delivered via bicarbonate pump 183 to a mixing line 186, which also receives water from the directing circuit 142. Acid from an acid source 29 (which may be in a liquid form) is also pumped via an acid pump 184 to the mixing line 186. The ingredients 49 (water, bicarbonate, acid, NaCl, etc.) are mixed in mixing chamber 189 to produce dialysate, which then flows out of mixing circuit 25 to the directing circuit 142. Conductivity sensors 178 and 179 are positioned along mixing line 186 to ensure that as each ingredient is added to the mixing line, it is added at proper concentrations. The volumes delivered by the water pump 180 and/or the other pumps may be directly related to the conductivity measurements, so the volumetric measurements may be used as a cross-check on the composition of the dialysate that is produced. This may ensure that the dialysate composition remains safe even if a conductivity measurement becomes inaccurate during a therapy.

Figure 7:
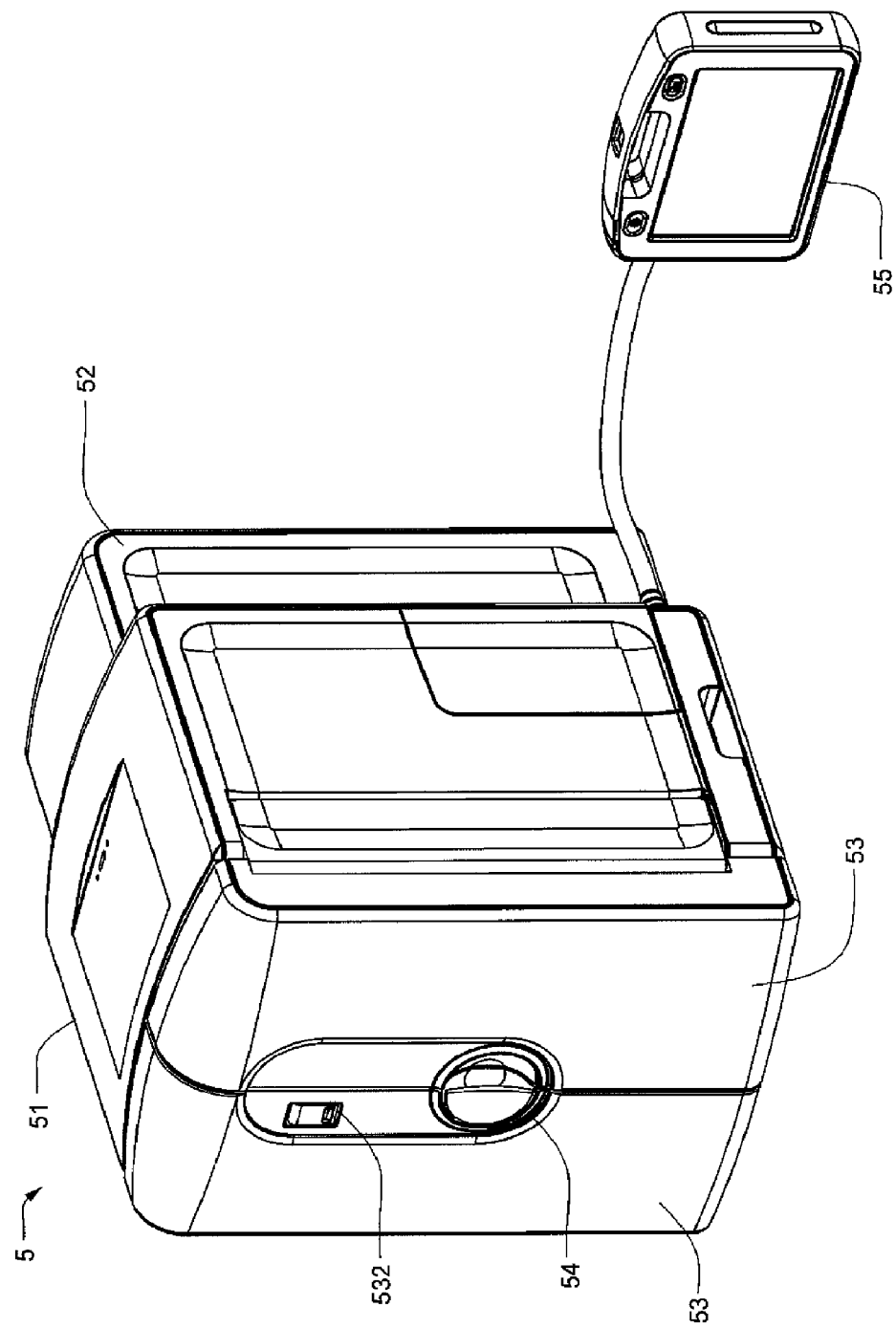
FIG. 7 is a right front perspective view of a hemodialysis system in an illustrative embodiment.

FIG. 7 shows a perspective view of a hemodialysis system 5 that incorporates various aspects of the invention. In accordance with one aspect of the invention, the system 5 includes a dialysis unit 51 and a power unit module 52 that are shown joined together. In this embodiment, the dialysis unit 51 has a housing that contains suitable components for performing hemodialysis, such as a dialyzer, one or more pumps to circulate blood through the dialyzer, a source of dialysate, and one or more pumps to circulate the dialysate through the dialyzer. For example, the dialysis unit 51 may include the mixing circuit 25, blood flow circuit 141, the balancing circuit 143 and the directing circuit 142 as described above. The dialysis unit 51 may also include all blood circuit connections and dialysate fluidic connections needed for operation of the system 5. Patient access and other connections may be revealed by opening side-by-side vertical doors 53 via a handle 54 at a front side of the dialysis unit 51 housing. In this embodiment, the dialysis unit 51 includes a control interface 55 (attached to the housing by a flexible cable in this embodiment) that a user may use to control operation of the dialysis unit 51. The control interface 55 may include a display screen with a touch sensitive overlay to allow touch control and interaction with a graphical user interface presented on the screen. The control interface 55 may also include other features, such as push buttons, a speaker, a microphone for receiving voice commands, a digital camera, and so on. The back side of the control interface 55 may include a retractable "kick-stand" (not shown) that allows the control interface 55 to be positioned on top of the dialysis unit 51 housing. Deploying the retractable "kick-stand" permits the control interface 55 to be placed in a near-vertical position to allow proper viewing of the display screen.

The power unit 52 housing may contain suitable components for providing operating power to the dialysis unit 51, e.g., pneumatic pressure/vacuum to power the pumps, valves and other components of the dialysis unit 51. "Pneumatic," as used herein, means using air or other gas to move a flexible diaphragm or other member. (It should be noted that air is used by way of example only, and in other embodiments, other control fluids, such as nitrogen ($N_2$), $CO_2$, water, an oil, etc., may be used). As discussed above, the pumps and valves of the dialysis unit 51 may operate on pneumatic power, and thus the power unit 52 may provide one or more pneumatic sources for use by the dialysis unit 51. In this way, the dialysis unit 51 need not necessarily be arranged to generate and/or store the necessary pneumatic power needed, but instead may rely on the power unit module 52. The power unit 52 may include one or more pneumatic pumps to generate desired air pressure and/or vacuum, one or more accumulators or other devices to store pneumatic power, valves, conduits and/or other devices to control flow of pneumatic power in the power unit 52, as well as a controller having suitable components, such as a programmed general purpose data processor, memory, sensors (e.g., to detect pressure, temperature, etc.), relays, actuators, and so on.

In one embodiment, the pneumatic power (e.g., air under suitable pressure/vacuum) may be supplied by the power unit 52 to the dialysis unit 51 via one or more supply tanks or other pressure sources. For instance, if two tanks are used in the power unit 52, one supply tank may be a positive pressure reservoir, and in one embodiment, has a set point of 750 mmHg (gauge pressure) (1 mmHg is about 133.3 pascals). The other supply tank can be a vacuum or negative pressure reservoir, and in one embodiment, has a set point of −450 mmHg (gauge pressure). This pressure difference may be used, for instance, between the supply tanks and the required pod pump pressure to allow for accurate control of the variable valves to the pod pumps. The supply pressure limits can be set based on maximum pressures that can be set for the patient blood flow pump plus some margin to provide enough of a pressure difference for control of the variable valves. Thus, in some cases, the two tanks may be used to supply pressures and control fluids for all of the dialysis unit 51 functions.

In one embodiment, the power unit 52 may include two independent compressors to service the supply tanks. Pressure in the tanks can be controlled using any suitable technique, for instance, with a simple "bang-bang" controller (a controller that exists in two states, i.e., in an on or open state, and an off or closed state), or with more sophisticated control mechanisms, depending on the embodiment. As an example of a bang-bang controller, for the positive tank, if the actual pressure is less than a set point, the compressor servicing the positive tank is turned on. If the actual pressure is greater than a set point, the compressor servicing the positive tank is turned off. The same logic may be applied to the vacuum tank and control of the vacuum compressor with the exception that the sign of the set point term is reversed. If the pressure tanks are not being regulated, the compressor is turned off and the valves are closed.

Tighter control of the pressure tanks can be achieved by reducing the size of the Is hysteresis band, however this may result in higher cycling frequencies of the compressor. If very tight control of these reservoirs is required, the bang-bang controller could be replaced with a proportional-integral-derivative ("PID") controller and using pulse width modulation ("PWM") signals on the compressors. Other methods of control are also possible.

Other pressure sources may be used in other embodiments, and in some cases, more than one positive pressure source and/or more than one negative pressure source may be used. For instance, more than one positive pressure source may be used that provides different positive pressures (e.g., 1000 mmHg and 700 mmHg), which may be used to minimize leakage. For example, high positive pressure can be used to control valves, whereas lower positive pressures can be used to control pumps. This limits the amount of pressure that can potentially be sent to the dialyzer or to the patient, and helps to keep actuation of the pumps from overcoming the pressures applied to adjacent valves. A non-limiting example of a negative pressure is −400 mmHg. In some cases, the negative pressure source may be a vacuum pump, while the positive pressure pump may be an air compressor.

Figure 8:
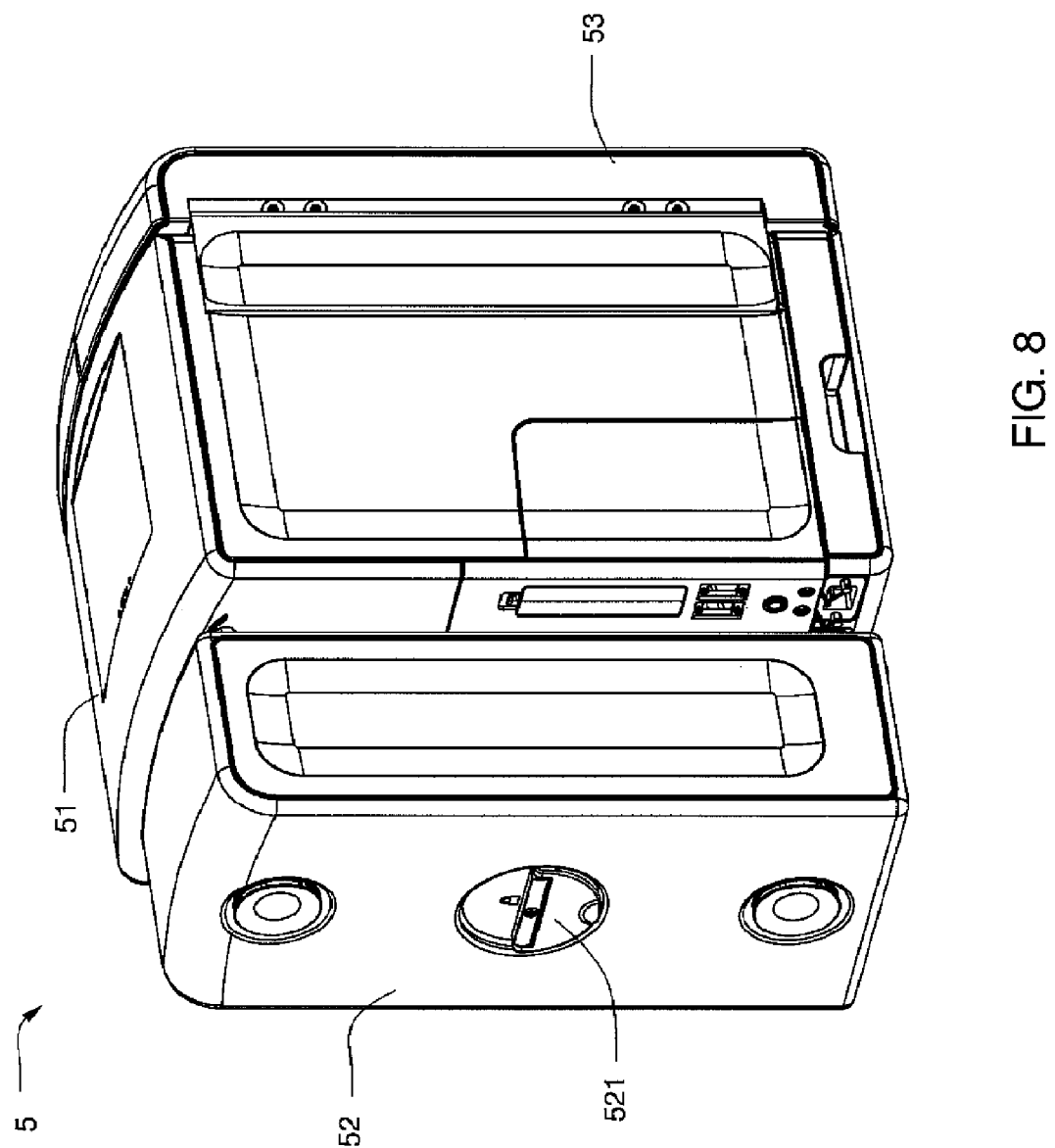
FIG. 8 is a left rear perspective view of the hemodialysis system of FIG. 7.

Moreover, the power unit 52 may be selectively connectable to the dialysis unit 51, e.g., to allow different power units 52 to be interchanged. For example, the dialysis unit 51 may be arranged to work with different types of power units 52, such as power units 52 that use electrical power to generate the pneumatic power supply, as well as power units 52 that use stored pneumatic power (e.g., pressurized air stored in one or more high pressure tanks). Thus, a power unit 52 may be interchanged for another unit 52, in case of failure or other requirements. For example, it may be desired to use the system 5 in an area where noise generation is unacceptable, such as when nearby people are sleeping. In this case, it may be desirable to use a power unit 52 that uses stored pneumatic power, rather than a unit 52 that generates pneumatic power by running pumps or other noise generating equipment. As shown in FIG. 8, the power unit 52 may be disconnected from the dialysis unit 51 by manipulating a handle 521. For example, turning the handle 521 may unlock the power unit 52 from the dialysis unit 51, disengaging not only mechanical connections between the housings, but also power and/or communications connections between the two. An interface (not shown) between the dialysis unit 51 and the power unit 52 may permit the units to exchange pneumatic power (from the power unit 52 to the dialysis unit 51) as well as electrical power, control communications, and other. The dialysis unit 51 may have connection points for electrical power (e.g., standard 115V, 15 amp power found in most home power outlets), external communication (such as Ethernet, or any other suitable connection suitable for communication), a water supply, and so on. The dialysis unit 51 may provide electrical power or other connections to the power unit 52, if desired.

The dialysis unit 51 may include a controller to control flow of control fluid for various components of the system 5, as well as perform other desired functions. In some cases, the control fluid may be held at different pressures within the various tubes or conduits. For instance, some of the control fluid may be held at positive pressure (i.e., greater than atmospheric pressure), while some of the control fluid may be held at negative pressures (less than atmospheric pressure). In addition, in certain embodiments, the controller may have components that are kept separate from the various liquid circuits. This configuration has a number of advantages. For example, in one embodiment, the liquid circuits in the dialysis unit 51 may be heated to disinfection temperatures and/or exposed to relatively high temperatures or other harsh conditions (e.g., radiation) to effect disinfection, while electronic components of the controller may not be exposed to such harsh conditions, and may even be kept separate by an insulating wall (e.g., a "firewall") or the like. That is, the dialysis unit housing may have two or more compartments, e.g., one compartment with electronic and other components that may be sensitive to heat or other conditions, and another compartment with liquid circuit components that are heated or otherwise treated for disinfection.

Thus, in some embodiments, the system 5 may include a "cold" section (which is not heated), and a "hot" section, portions of which may be heated, e.g., for disinfection purposes. The cold section may be insulated from the hot section through insulation. In one embodiment, the insulation may be molded foam insulation, but in other embodiments can be any type of insulation, including but not limited to a spray insulation, an air space, insulation cut from sheets, etc. In one embodiment, the cold section includes a circulation system, e.g., a fan and/or a grid to allow air to flow in and out of the cold box. In some cases, the insulation may be extended to cover access points to the "hot" section, e.g., doors, ports, gaskets, and the like. For instance, when the "hot" section is sealed, the insulation may completely surround the "hot" section in some cases.

Non-limiting examples of components that may be present within the "cold" section include power supplies, electronics, power cables, pneumatic controls, or the like. In some cases, at least some of the fluids going to and from the "hot" section may pass through the "cold" section; however, in other cases, the fluids may pass to the "hot" section without passing through the "cold" section.

Non-limiting examples of components that may be present within the "hot" section include cassettes (if present), fluid lines, temperature and conductivity sensors, blood leak sensors, heaters, other sensors, switches, emergency lights, or the like. In some cases, some electrical components may also be included in the "hot" section. These include, but are not limited to, a heater. In one embodiment, the heater can be used to heat the hot box itself, in addition to fluid. In some embodiments, the heater 72 heats the entire "hot" section to reach a desired temperature.

Figure 9:
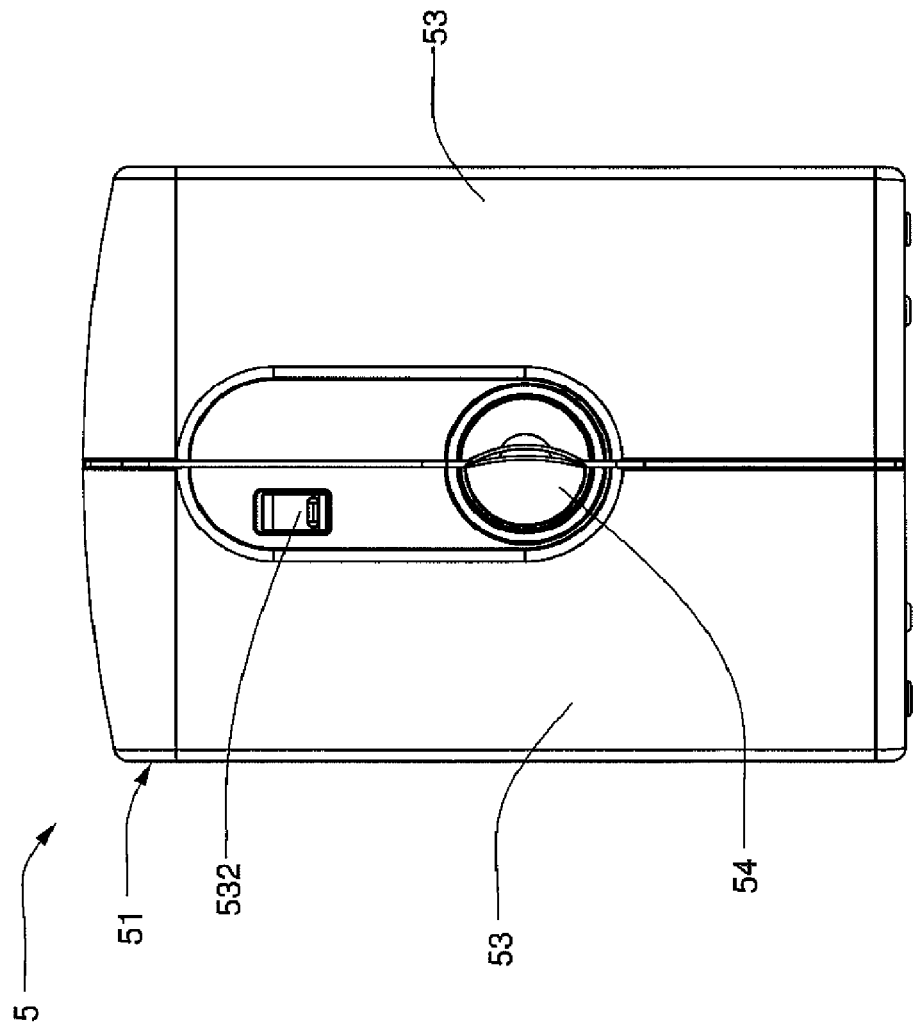
FIG. 9 is a front view of the hemodialysis system of FIG. 7.
Figure 10:
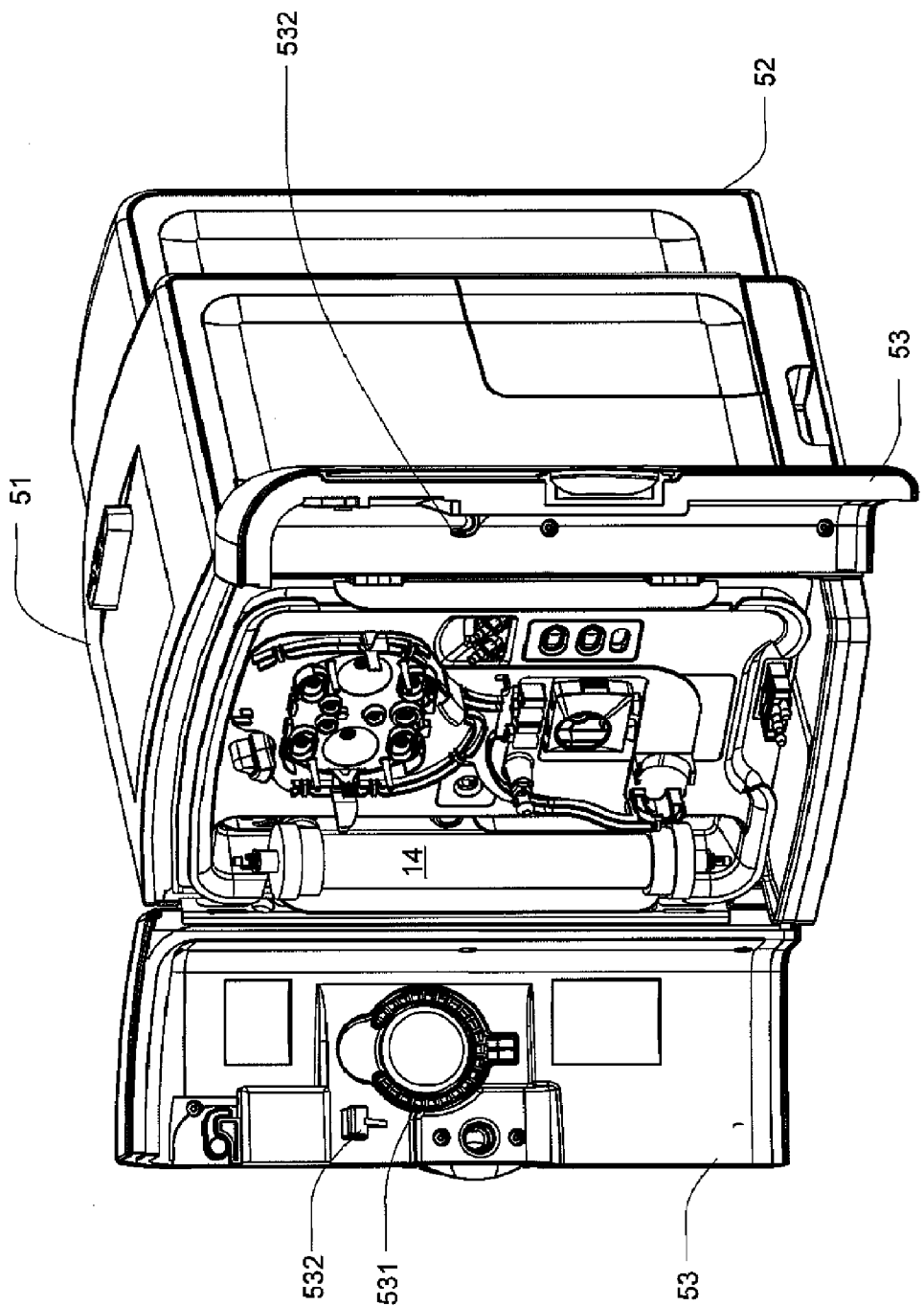
FIG. 10 is a right front perspective view of the view of the hemodialysis system of FIG. 7 with the doors in a first open position.
Figure 11:
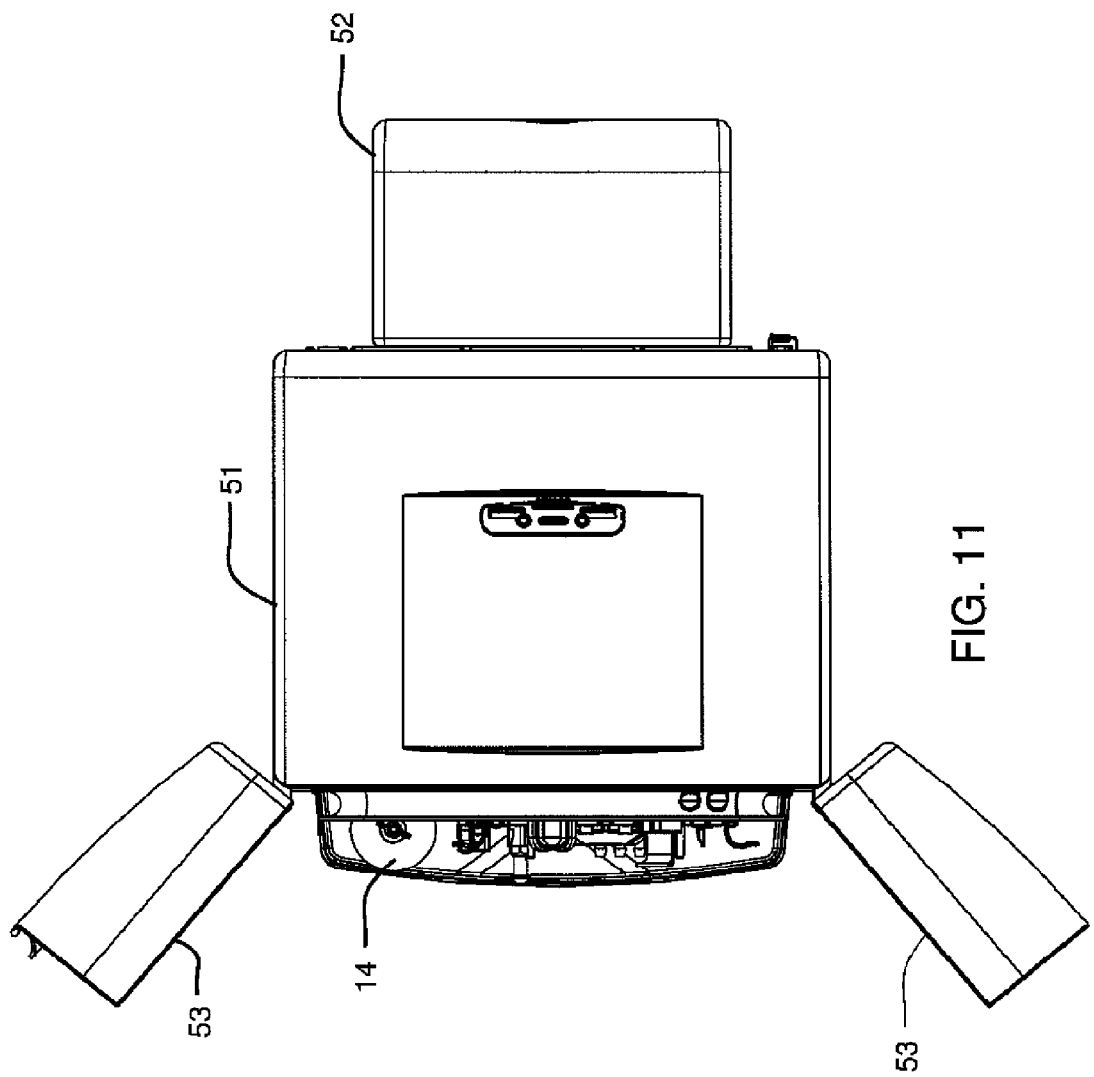
FIG. 11 is a top view of the hemodialysis system of FIG. 10.
Figure 12:
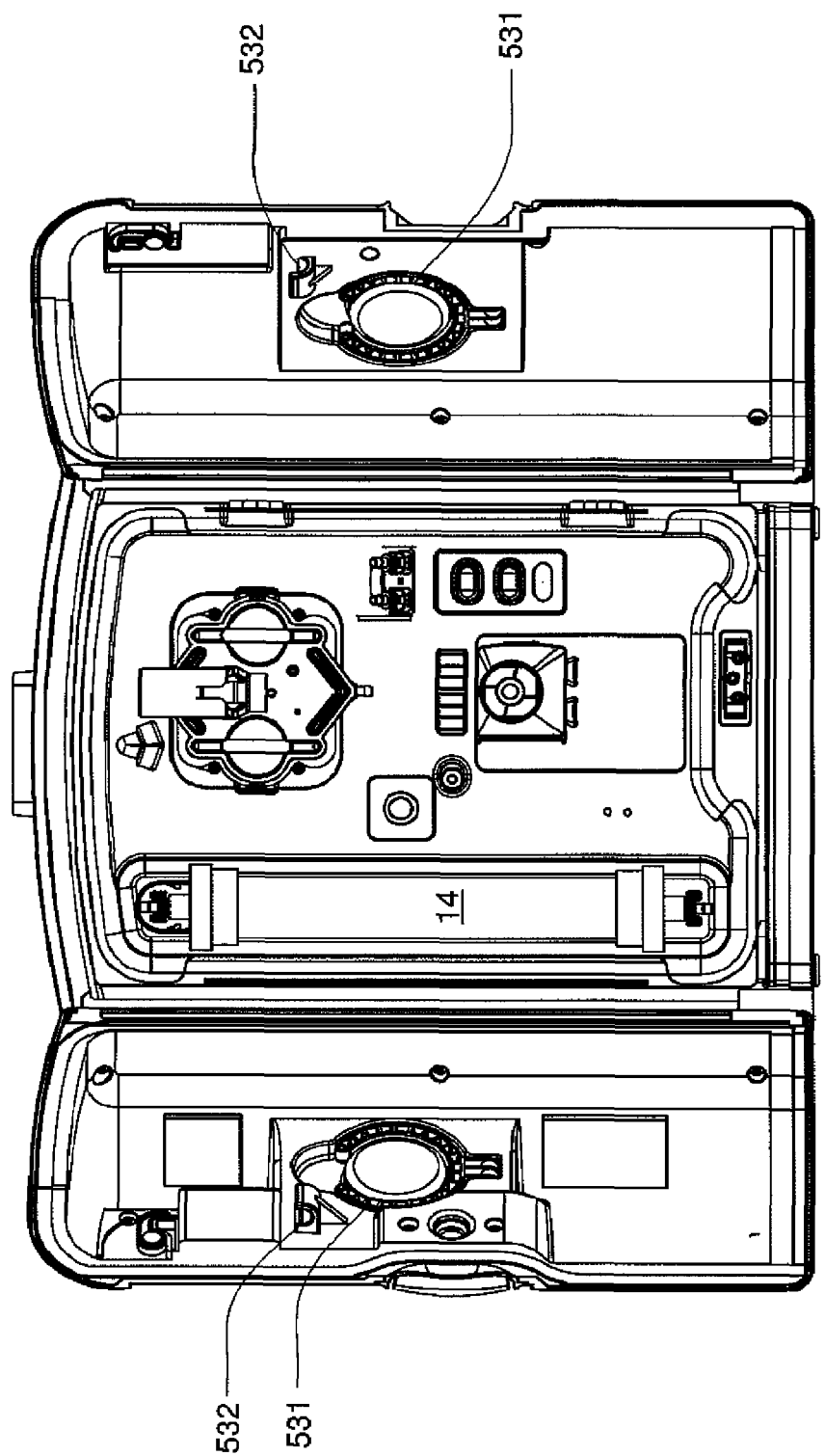
FIG. 12 is a front view of the hemodialysis system of FIG. 10.
Figure 13:
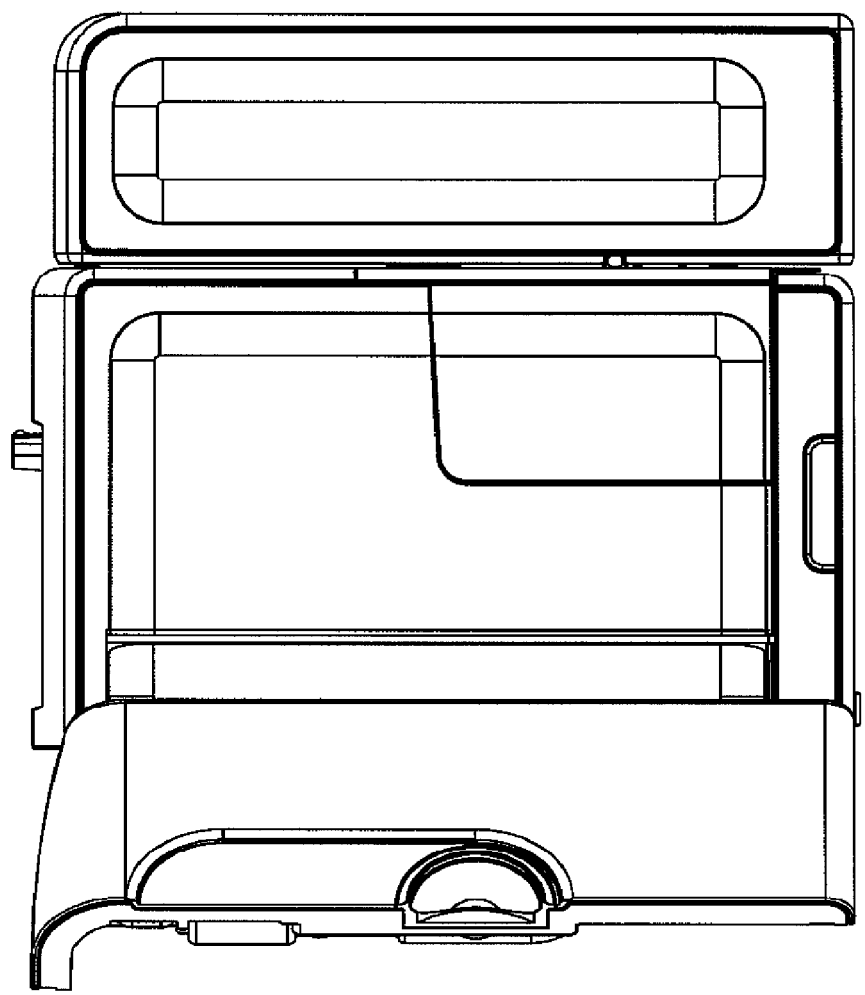
FIG. 13 is a right side view of the hemodialysis system of FIG. 10.

In accordance with an aspect of the invention, the dialysis unit 51 housing may include vertical side-by-side doors that can be opened to expose all mechanical interface points for blood flow circuitry and connections for dialysate circuitry, i.e., all connection points for patient blood connections and acid/bicarbonate connections, that must be made by a user to use the dialysis unit 51. FIG. 9 shows a front view of the dialysis unit 51 with the vertical side-by-side doors 53 in a closed state. In this arrangement, the doors 53 may block access to connection points for patient blood connections and acid/bicarbonate connections as well as seal the interior of the unit housing so as to allow heat retention suitable for disinfection. The seal provided by the doors 53 may be hermetic, preventing or substantially resisting any air exchange between the housing interior and an exterior environment, or may be of a somewhat lesser quality yet still allow for disinfection.

In this embodiment, the doors 53 are connected to the dialysis unit 51 housing by a dual hinge arrangement such that the doors 53 can be opened to two different states of opening. FIGS. 10-13 show the doors 53 in a first state of opening. In this state, the doors 53 expose all user-made connections for the blood circuit connections and for the dialyzer circuitry, including the dialyzer 14 itself and for reagent materials, such as consumable acid/bicarbonate materials. This position also exposes several other features, such as holders 531 for an acid/bicarbonate container (not shown) and hooks 532 that may be used to hold any suitable item, such as the control interface 55, which may be hung by its handle on one of the hooks 532. (See also FIG. 7 which shows a hook 532 on the front of the left door 53 which may be folded out to receive the control interface 55 or other item.) The holders 531 in this embodiment may be folded down from their position shown in the figures (i.e., folded up and into recesses in the doors 53) so as to extend horizontally from the doors 53. The holders 531 have a "C" shaped receiving section to receive and hold an acid/bicarbonate container, but of course could be shaped or otherwise arranged in any suitable way.

Figure 14:
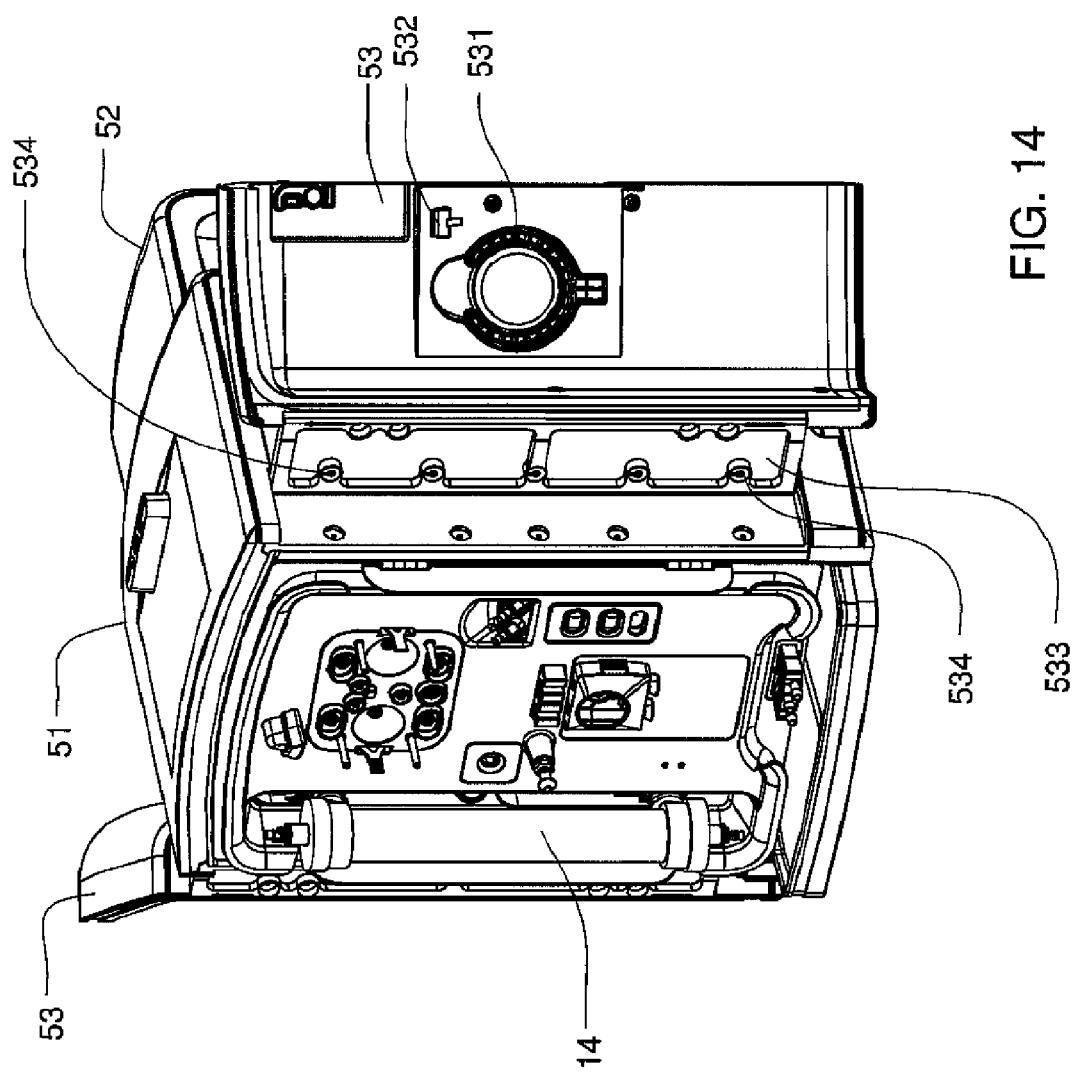
FIG. 14 is a right front perspective view of the view of the hemodialysis system of FIG. 7 with the doors in a second open position.
Figure 15:
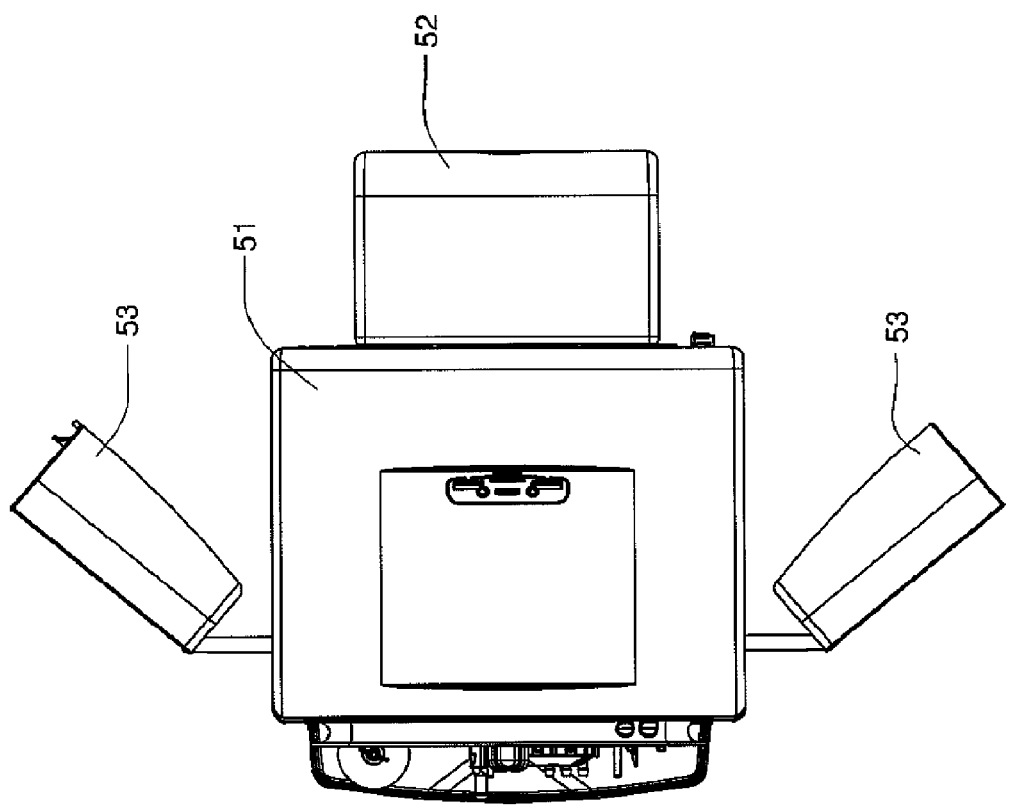
FIG. 15 is a top view of the hemodialysis system of FIG. 14.
Figure 16:
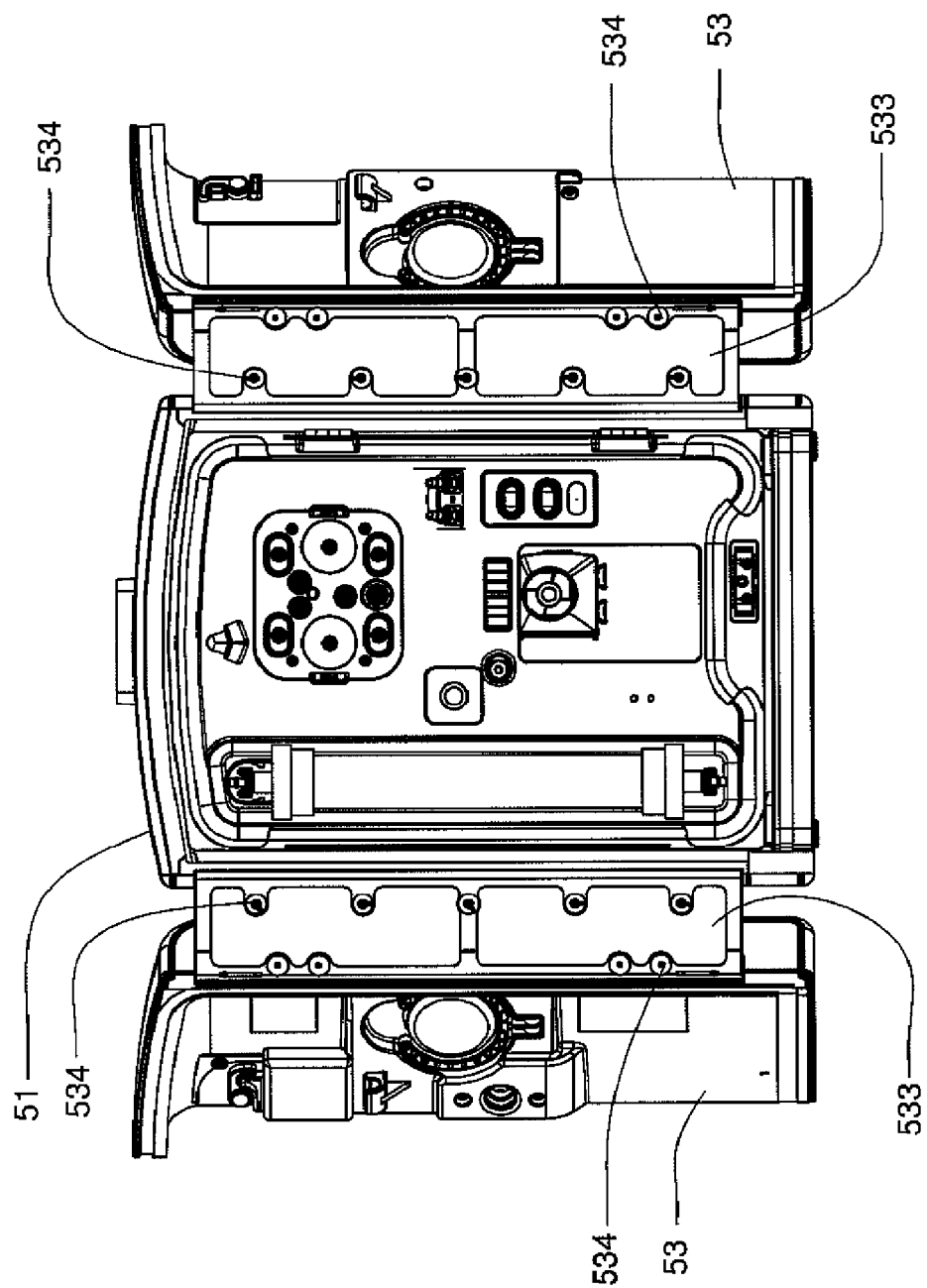
FIG. 16 is a front view of the hemodialysis system of FIG. 14.

FIGS. 14-16 show the doors 53 in a second state of opening in which a hinge plate 533 for each door 53 is pivoted outward and away from the dialysis unit housing 51. The hinge plates 533, which in this embodiment extend vertically along almost the entire height of the dialysis unit housing 51, are pivotally attached to the doors 53 at a first, outer end, and are pivotally attached at a second inner end to the dialysis unit housing 51. (Of course, it should be understood that the hinge plates 533 could be arranged and/or positioned differently, e.g., at the top and bottom of the doors 53 as is found in many refrigerator door arrangements, each plates 533 may include two or more portions that are vertically separated from each other, etc.) Magnets 534 attached to the hinge plates 533 may interact with corresponding magnets (or other suitable components, such as steel elements) attached to the dialysis unit housing 51 so as to attract the hinge plates 533 toward the dialysis unit housing 51, thus tending to keep the hinge plates 533 in the position shown in FIGS. 10-13. (Of course, the magnets 534 could be positioned on the unit housing, and the hinge plates 533 could have suitable elements (such as pieces of steel) that are attracted to the magnets 534.) The doors 53 in this embodiment also include magnets attached near the hinge plates 533 so that when the doors 53 are opened to the first state as shown in FIGS. 10-13, the magnets interact with corresponding magnets in the hinge plates 533 to help keep the doors 53 in an open position relative to the hinge plate 533. These magnets will also help maintain the relative position of the doors 53 and the hinge plates 533 when the hinge plates 533 are opened to the second state shown in FIGS. 13-16.

Although magnets are used in this illustrative embodiment as part of a retainer member to help the doors 53 and/or hinge plates 533 stay in a particular state of opening or closing, other arrangements for a retainer member are possible. For example, the hinge connection between the doors 53 and the hinge plates 533 and/or the connection between the hinge plates 533 and the housing 51 may include a detent arrangement that serves to resiliently hold the door 53 or hinge plate 533 in a particular position relative to the other part (the hinge plate or housing, respectively). In another embodiment, one or more springs may be used to help maintain the doors 53 in an open position relative to the hinge plates 533. In yet another embodiment, the hinge plates 533 may have a friction or interference fit with a portion of the housing 51 that tends to maintain the hinge plates 533 in the closed position (adjacent the housing). Accordingly, a retainer member that functions to help maintain a door 53 in a particular position relative to its hinge plate 533, and/or that functions to help maintain a hinge plate 533 in a particular position relative to the housing 51, may take any one of a number of possible arrangements.

Figure 17:
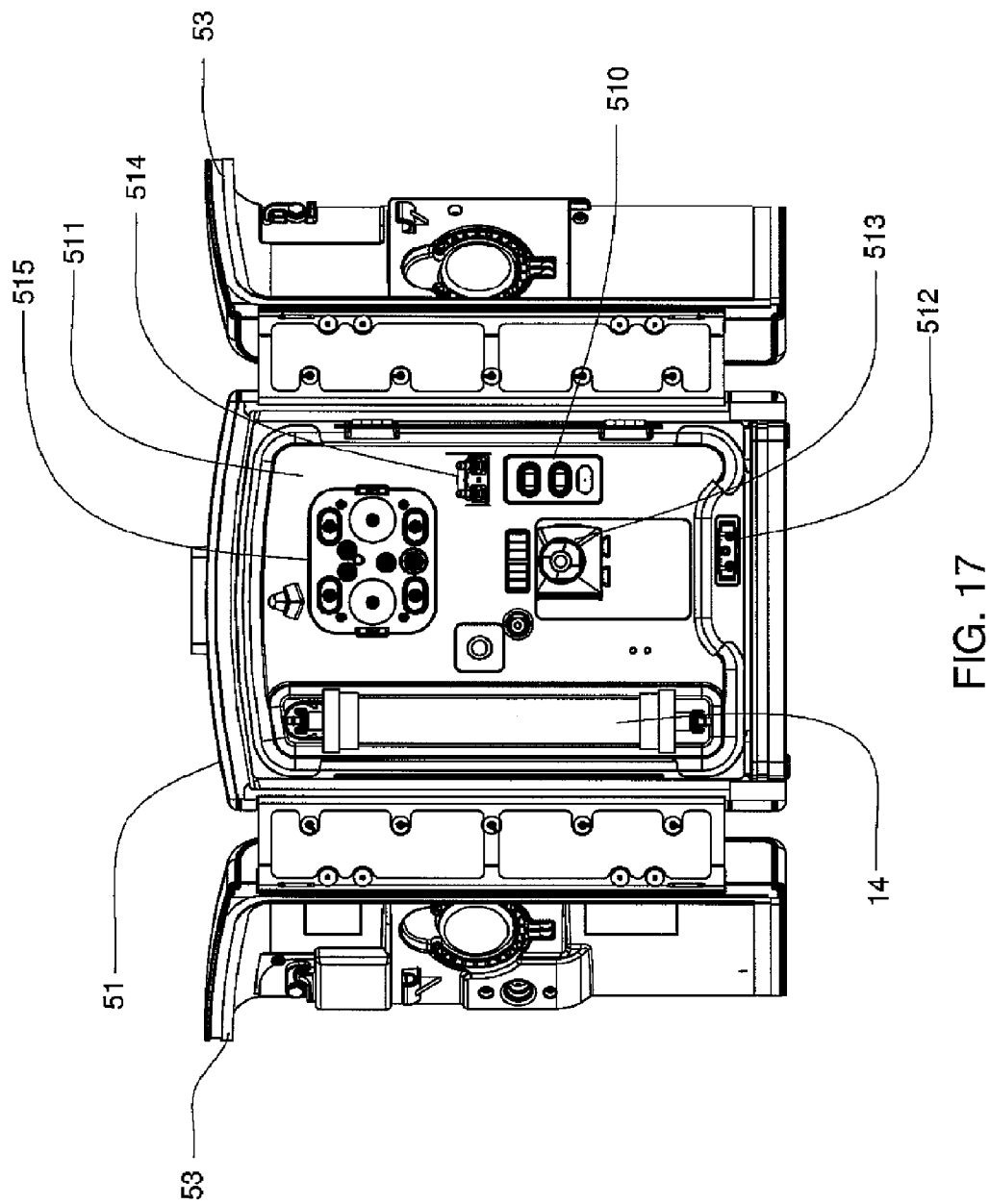
FIG. 17 is a front view of the hemodialysis system of FIG. 7 with the doors in an open position exposing a front panel of the system.

In accordance with another aspect of the invention, opening of the doors to the dialysis unit housing may reveal all of the user-made connections for blood circuit connections and dialysate fluidic connections needed for operation of the system 5. For example, as shown in FIG. 17, with the doors 53 in an open position (either the first or second state of opening) a front panel 511 of the dialysis unit 51 may be exposed. In this embodiment, the front panel 511 carries several items or connection points that must be accessed by a user. For example, the dialyzer 14, which must be periodically replaced, is mounted to the front panel 511. The dialyzer 14 must be connected not only to the blood flow circuit 141, but also the balancing circuit 143. Also, a connection point 512 for an acid/bicarbonate source 49 is located at a lower end of the front panel 511. It is at this connection point 512 that a user may connect a source of consumable reagent ingredients 49 used by the dialysis unit 51 in making dialysate. An occluder 513 is also mounted on the front panel 511. The occluder 513 receives tubes of the blood flow circuit and controls the open/closed state of the tubes based on system operation. The function of the occluder 513 is discussed in more detail in U.S. application Ser. No. 12/198,947, filed Aug. 27, 2008 (under) and below. In short, the occluder 513 allows flow through the arterial and venous lines of the blood flow circuit unless there is a system problem, such as a leak, pump failure, overpressure situation, etc. In such case, the occluder 513 automatically closes the blood lines to prevent all flow to or from the patient. Also exposed on the front panel 511 are blood line connection points 514 for connecting the arterial and venous blood lines 203, 204 of the blood flow circuit 141 with the directing circuit 142 (as explained above with reference to FIGS. 2 and 3, the blood flow circuit 141 may be connected to the directing circuit 142). This connection is normally made at the end of treatment to allow the system to clean and disinfect the blood flow circuit 141. The front panel 511 also has a set of control ports 515 that mate with corresponding control ports on the blood pump portion of the blood flow circuit 141. The control ports 515 provide controlled levels of air pressure and/or vacuum to control the open/closed state of valves and to power the pumps of the blood flow circuit 141.

Also exposed on the front panel 511 is a user control panel 510. The user control panel 510 includes one or more buttons permitting the user to bypass the graphical user interface on control interface 55, providing an alternate method to control certain functions (e.g., critical functions) during hemodialysis. This may be important, for example, if the control interface 55 should ever fail during a dialysis treatment session. Non-limiting examples of critical functions can include a "stop dialysis" or "pause dialysis" command and an "infuse dialysate solution" command.

Figure 18:
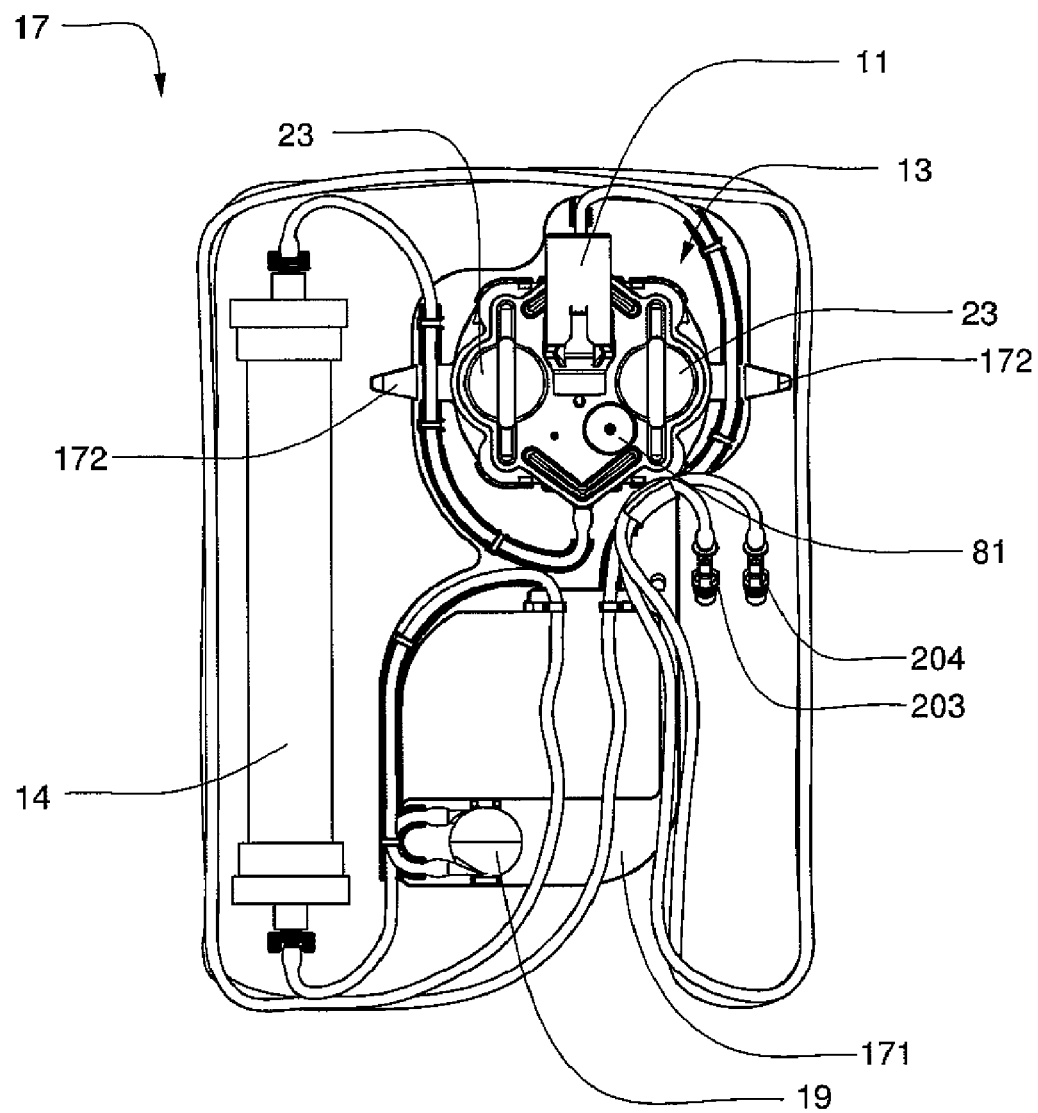
FIG. 18 is a front view of a blood circuit assembly for use with the system of FIG. 7.

FIG. 17 does not show the arterial and venous lines 203, 204 for the blood flow circuit 141 because in this embodiment and in accordance with another aspect of the invention, the blood flow circuit 141 is formed as a blood circuit assembly that is removable from the front panel 511 of the dialysis unit 51, and the blood circuit assembly is not mounted on the front panel 511 in FIG. 17. FIG. 18 shows a front view of the blood circuit assembly 17 in this embodiment along with the dialyzer 14. The blood circuit assembly 17 includes various components discussed above, for example with reference to FIG. 3, that are mounted to a blood circuit organizing tray 171. The arterial and venous lines 203 and 204 (e.g., including lengths of flexible silicone tubing) are terminated with blood line connectors that, in one aspect of the invention, are arranged to provide a plug-in or press-in connection with the blood line connection points 514 as well as provide a screw-type connection used with standard patient access points (e.g., luer type patient access connectors). The arterial line 203 leads to an inlet at the top of the blood pump 13, which includes two pod pumps 23, valves and other components for controlling blood flow. Associated with the blood pump 13 are an air filter 81, an anticoagulant pump 80 (not shown), and an anticoagulant supply 11 (such as a vial of heparin). (Details regarding the blood pump 13 in this illustrative embodiment may be found in U.S. patent application Ser. No. 11/871,680, filed Oct. 12, 2007 and published as U.S. Patent Application Publication No. 2008/0208103 on Aug. 28, 2008, entitled "Pumping Cassette"; U.S. patent application Ser. No. 11/871,712, filed Oct. 12, 2007, entitled "Pumping Cassette"; U.S. patent application Ser. No. 11/871,787, filed Oct. 12, 2007 and published as U.S. Patent Application Publication No. 2008/0253911 on Oct. 16, 2008, entitled "Pumping Cassette"; U.S. patent application Ser. No. 11/871,793, filed Oct. 12, 2007 and published as U.S. Patent Application Publication No. 2008/0253912 on Oct. 16, 2008, entitled "Pumping Cassette"; and U.S. patent application Ser. No. 11/871,803, filed Oct. 12, 2007 and published as U.S. Patent Application Publication No. 2008/0202591 on Aug. 28, 2008, entitled "Cassette System Integrated Apparatus.") Blood output from the blood pump 13 (the outlet is located at a bottom of the pump 13) flows to an inlet of the dialyzer 14 (at the top of the dialyzer 14), and out of the dialyzer (the dialyzer blood outlet is located at the bottom of the dialyzer 14) to the inlet of the air trap 19. The outlet of the air trap 19 is connected to the venous blood line 204. Connections to the inlet and outlet blood ports of the dialyzer 14 are made with typical screw-type connections.

In accordance with another aspect of the invention, the air trap 19 is placed in the blood flow path after the blood exits the dialyzer and before it is returned to the patient. In an embodiment, air trap 19 can have a spherical or spheroid-shape container (i.e., a container having an approximately spherical inner wall), and have its inlet port located near the top and offset from the vertical axis of the container, and an outlet at a bottom of the container. (The vertical axis of the container is arranged in a vertical direction passing through the top and bottom "poles" of the approximately spherical container.) With the inlet port offset from the vertical axis (in this case set back toward the tray 171), blood is introduced into the container in a direction that is approximately perpendicular to the vertical axis of the container and that is approximately tangential to the spherical inner wall of the container. The curved shape of the inside wall of the trap can thus direct the blood to circulate along the inside wall as the blood gravitates to the bottom of the container (e.g., in a spiral like fashion), facilitating the removal of air bubbles from the blood. Air present in the blood exiting the outlet of the dialyzer 14 will enter at the top of the air trap 19 and remain at the top of the container as blood flows out the outlet at the bottom and to the venous blood line 204. By locating the inlet port near the top of trap 19, it is also possible to circulate blood through the trap with minimal or no air present within the container (as a "run-full" air trap. The ability to avoid an air-blood interface for routine circulation of blood in the trap can be advantageous. Placing the inlet port at or near the top of the container also allows most or all of the air present in the trap to be removed from the trap by reversing the flow of fluid through the blood tubing (i.e. from the bottom to the top of the trap 19, exiting through the inlet port of the trap 19).

In an embodiment, a self-sealing port, such as a self-sealing stopper with a split septum or membrane, or another arrangement, is located at the top of the trap, allowing the withdrawal of air from the container (e.g., by syringe). The blood-side surface of the self-sealing membrane can be situated nearly flush with the top of the interior of the trap, in order to facilitate cleaning of the self-sealing port during disinfection, e.g., by reversing flow through the air trap using a dialysate or other cleaning fluid. Also, the inlet, outlet and internal wall of the container and the self-sealing port may be arranged to substantially eliminate stagnation regions, i.e., allow for few or no regions where blood can stagnate or clot. The self-sealing port can also serve as a blood sampling site, and/or to allow the introduction of liquids, drugs or other compounds into the blood circuit. A sealed rubber-type stopper can be used if access with a needle is contemplated. Using a self-sealing stopper with split septum permits sampling and fluid delivery using a needleless system.

Figure 19:
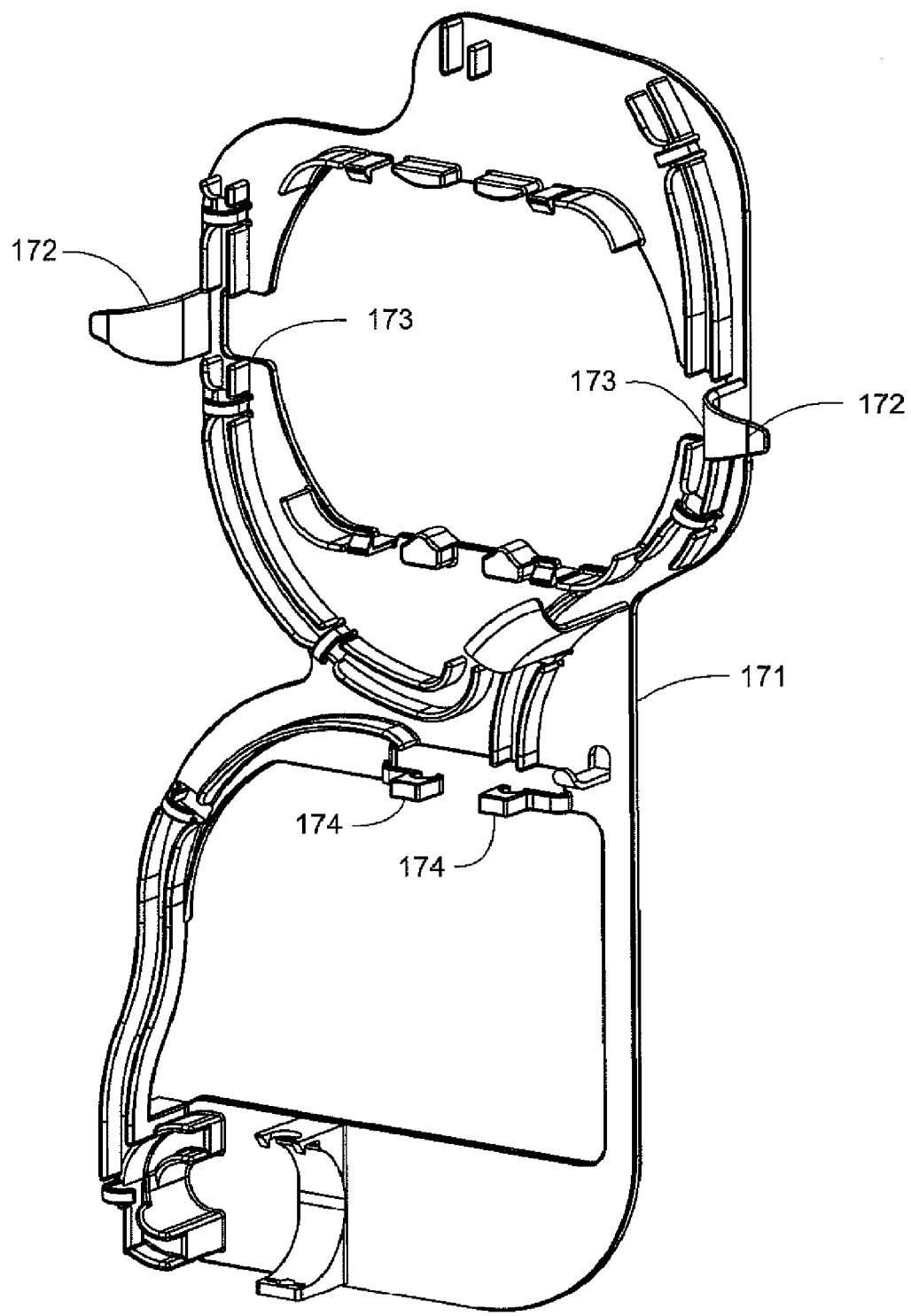
FIG. 19 right perspective view of a organizing tray for the blood circuit assembly of FIG. 18.

FIG. 19 shows the organizing tray 171 for the blood circuit assembly 17 without the various blood circuit assembly 17 components mounted. In accordance with one aspect of the invention, the organizing tray 171 includes handles 172 (in this embodiment, finger pulls) that a user can grip when mounting/dismounting the blood circuit assembly 17 to the front panel 511. Inward of the handles 172 are openings 173 that allow spring tabs on the front panel 511 to pass through and engage with the organizing tray 171 and/or the blood pump 13 cassette to hold the blood circuit assembly 17 in place on the front panel 511. In accordance with another aspect of the invention, the organizing tray 171 includes blood line engagement members 174 that each have a C-shaped recess or other hole through which a corresponding blood line 203, 204 passes. (In this context, a "hole" includes a recess like that shown in FIG. 19, a throughbore that has a continuous wall, e.g., as may be made by a drill, or other suitable opening.) As described in more detail below, the blood line engagement members 174 are used when mounting the blood lines 203, 204 in the occluder 513. In short, when mounting the blood lines 203, 204 in the occluder 513, the blood lines 203, 204 must be pulled and stretched downwardly (so as to reduce the outside diameter of the line) while being pushed horizontally into slots for the occluder 513. The blood line engagement members 174 function to both resist downward pulling on the blood lines 203, 204 (e.g., each line 203, 204 may include a stop ring above the respective engagement member 174 that cannot be pulled through the recess in the engagement member 174) as well as permit the user to press inwardly on the engagement member 174 to seat the lines 203, 204 in the occluder slots. The engagement members 174 are formed integrally with the organizing tray 171 so that a "living hinge" or relatively flexible portion of the organizing tray is positioned between the engagement member 174 and the main body of the organizing tray 171. This arrangement allows the engagement members 174 to be pushed inwardly relative to the organizing tray 171 as the connection portion between the engagement members 174 and the organizing tray main body flexes.

Figure 20:
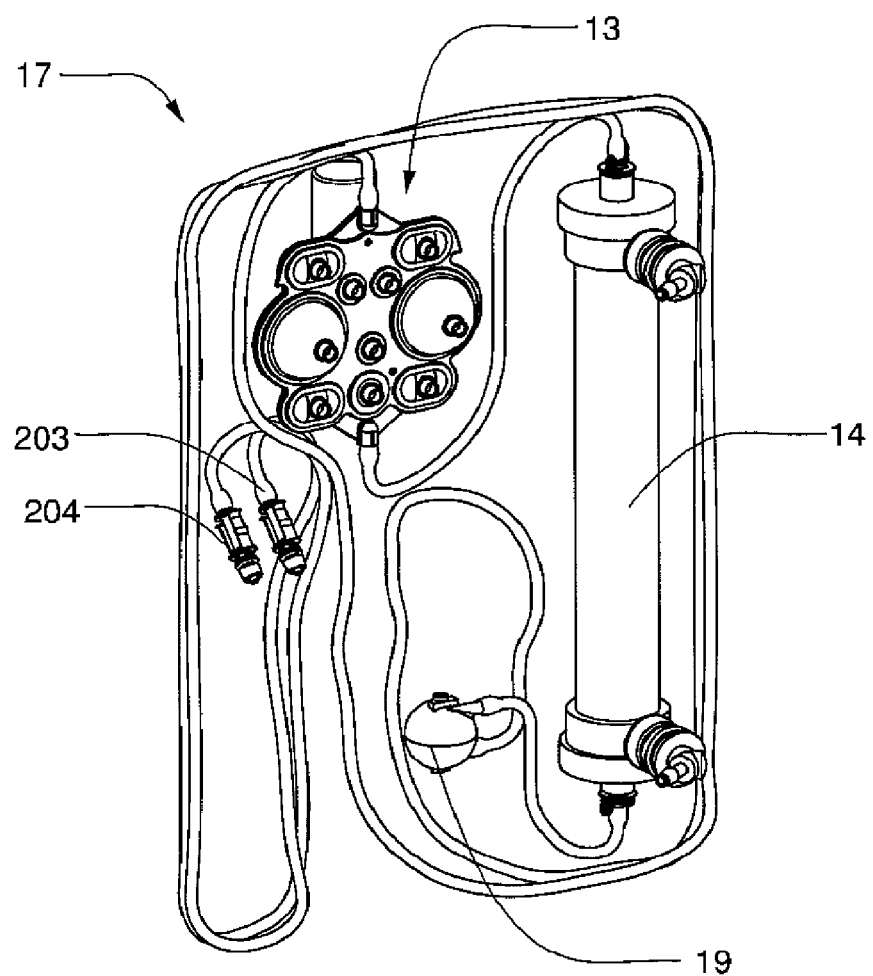
FIG. 20 is a left rear perspective view of the blood circuit assembly of FIG. 18.

FIG. 20 shows a rear view of the blood circuit assembly 17 with the organizing tray 171 removed. This view shows the rear side of the blood pump 13 section with control ports exposed. These control ports mate with corresponding ports 515 on the front panel 511 (see FIG. 17) so that pneumatic control (e.g., suitable air pressure or vacuum) can be applied to the pumps and valves to control their operation and flow through the blood circuit assembly 17. FIG. 20 also shows the offset of the inlet port of the air trap 19, i.e., the inlet port at the top of the air trap 19 is arranged to the rear of the vertical axis of the generally spherical container portion of the air trap 19.

Figure 21:
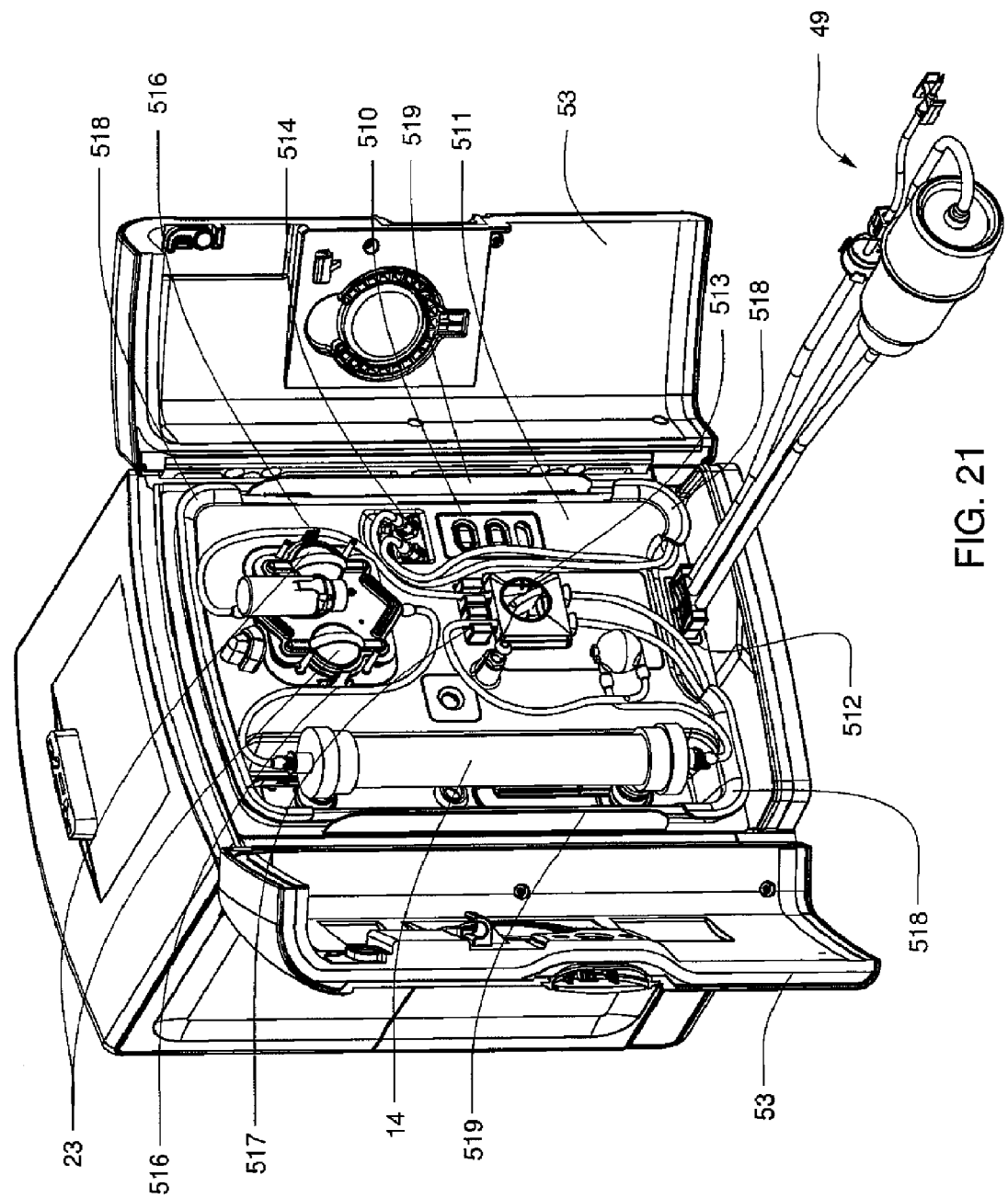
FIG. 21 shows a left front perspective view of the front panel of the system of FIG. 7.
Figure 22:
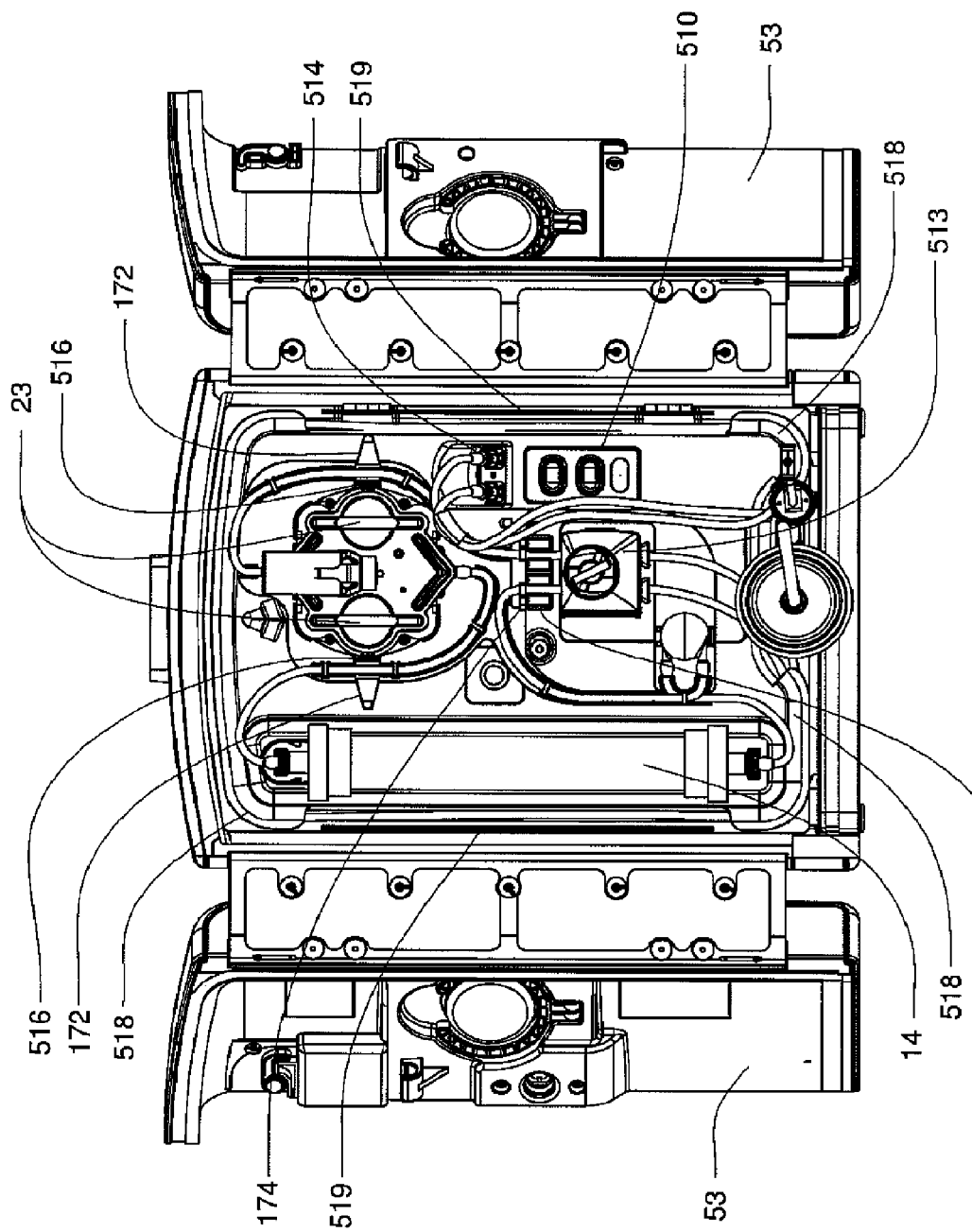
FIG. 22 shows a front view of the front panel of the system of FIG. 7.

FIG. 21 shows a perspective view of the front panel 511 of the dialysis unit 51 with the blood circuit assembly 17 mounted to the front panel 511 without the organizing tray 171. (Normally, the blood circuit assembly 17 would include the organizing tray 171, but the tray 171 is not shown in the example so as to more clearly show components at the front panel 511.) On opposite sides of the blood pump 13 cassette, the front panel 511 has spring tabs 516 that extend forwardly and resiliently engage with the blood pump cassette and/or the organizing tray 171 to retain the blood circuit assembly 17 in place. The tabs 516 may include a barb or other feature to help retain the blood circuit assembly 17 in place. The spring tabs 516 may be flexed outwardly to release their hold on the blood circuit assembly 17, allowing its removal. However, in the absence of an outwardly directed force on the spring tabs 516, the tabs 516 will remain engaged with the blood circuit assembly 17. FIG. 22 shows a front view of the front panel 511 with the organizing tray 171 of the blood circuit assembly 17 included. To remove the blood circuit assembly 17 from the front panel 511, a user may place index fingers behind the handles 172 while simultaneously placing thumbs on the inner side of the spring tabs 516 (the sides nearest the blood pumps 23) and flexing the spring tabs 516 outwardly and away from the pumps 23. This causes the spring tabs 516 to release the blood circuit assembly 17, e.g., disengagement of barbs on the tabs 516 from the blood pump 13 and/or the organizing tray 171. Of course, to remove the blood circuit assembly 17, other connections must be removed, including connections to the dialyzer 14 and the blood line connection points 514, as well as removal of the lines 203, 204 from the occluder 513. When mounting the blood circuit assembly 17 to the front panel 511, the organizing tray 171 may be grasped at the handles 172 and properly aligned, e.g., so that the spring tabs 516 are aligned to pass through the openings 173 and the control ports of the blood pump 13 cassette are aligned with the corresponding ports 515 on the front panel 511. The blood circuit assembly 17 may then be simply pushed into place, so that the spring tabs 516 engage with the organizing tray 171 and/or the blood pump cassette. Other connections can then be made, such as connections to the dialyzer 14, mounting of the blood lines 203,204 with the occluder 513, etc.

FIG. 21 also shows the slots 517 that hold the blood lines 203, 204 for leading into the occluder 513. The slots 517 define a channel that is slightly smaller than the outside diameter of the blood lines 203, 204 so that the lines 203, 204 tend to remain in the slots 517 after placement in the slots. This helps to ensure proper association of the lines with the occluder 513. Once the blood circuit assembly 17 is mounted on the spring tabs 516, the user may then engage the blood lines 203, 204 with the slots 517 by stretching the lines 203, 204 downward (with the engagement members 174 on the organizing tray 171 engaging the stop ring or other feature on the respective line 203, 204 and resisting the downward pull) and pushing the lines 203, 204 into a corresponding slot. The lines 203, 204 can be pushed into place by pressing inwardly on the engagement members 174, which as described above, are flexible and bend inwardly relative to the organizing tray 171. The lines 203, 204 can then be routed through the occluder 513.

In accordance with another aspect of the invention, the front panel 511 includes a blood line wrap feature around the periphery of the front panel 511. In this illustrative embodiment, the front panel 511 includes flanged portions 518 along the top edge and at lower corners of the front panel 511. This allows a user to wrap the blood lines 203, 204 around the periphery of the front panel 511 by placing the lines 203, 204 in a channel defined by the flanged portions 518. The lines 203, 204 may be wrapped in a clockwise direction, starting from a point near the bottom of the dialyzer 14, and ending at a point near the lower right corner of the front panel 511. The blood lines 203, 204 may then be connected at the blood line connection points 514, e.g., to allow disinfecting fluid to be circulated through the blood lines 203, 204. As a result, the blood lines 203, 204 can be neatly retained on the front panel 511, allowing easy access to other components on the front panel 511 and allowing the user to close the doors 53 with minimal concern for pinching the blood lines 203, 204 between the doors 53 and the dialyzer unit housing 51. Alternatively, the blood lines 203, 204 may be first connected at the blood line connection points 514, and then wrapped in a clockwise direction, starting from a point near the bottom of the dialyzer 14, and ending at a point near the lower right corner of the front panel 511. This ensures that the blood lines are properly distributed along the flanged portions 518 to reach the connection points 514. Vertical fences 519 may also be provided along the left and right sides of the front panel 511 to help keep the blood lines 203, 204 in a desired position and away from the hinge plates 533 and other possible pinch points.

Figure 23:
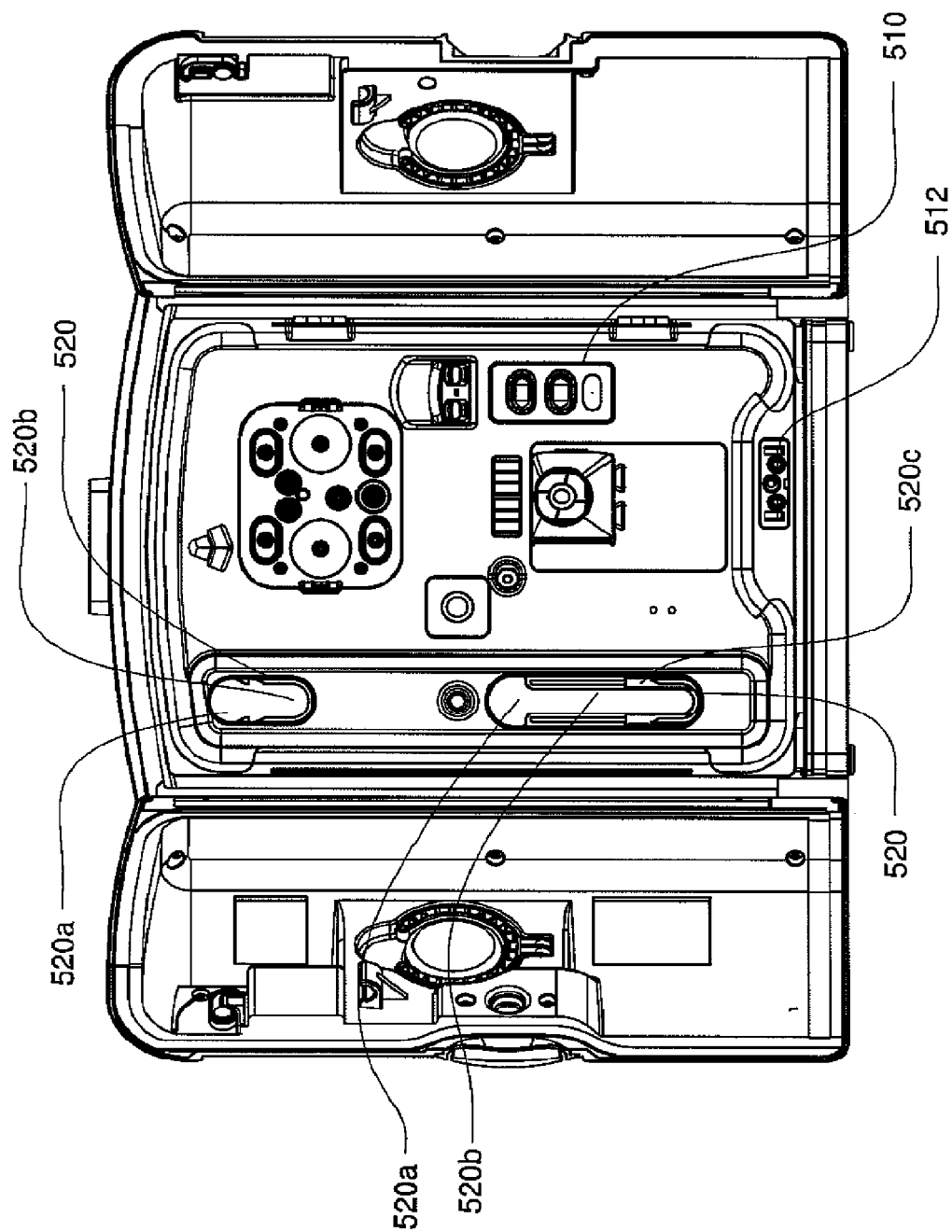
FIG. 23 shows a front view of the front panel of the system of FIG. 7 with a pair of mounting features for the dialyzer.
Figure 24:
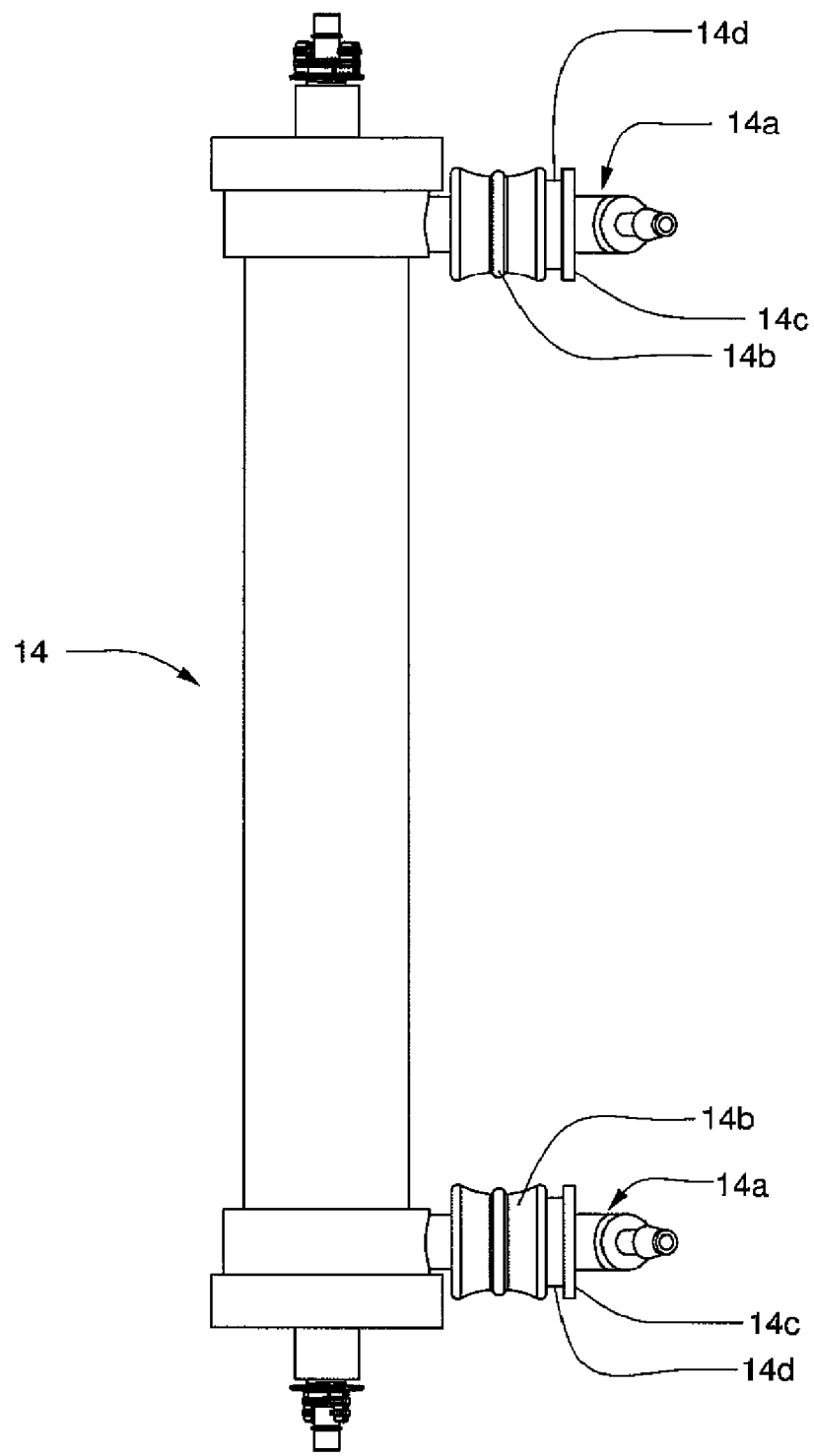
FIG. 24 shows a side view of a dialyzer with quick-connect fittings attached to the dialysate inlet/outlet ports of the dialyzer.

In accordance with another aspect of the invention, the front panel 511 of the dialysis unit 51 (or other suitable component) may be arranged to accommodate a variety of differently sized and/or shaped dialyzer units 14. Different patients, and in some cases even the same patient over time, may be prescribed different dialyzers so as to provide different treatment conditions. Thus, the dialysis unit 51 is preferably arranged to operate with multiple different types of dialyzers 14. In many cases, different dialyzers 14 have different dimensions, such as the overall diameter and/or length of the dialyzer unit. In this illustrative embodiment as shown in FIG. 23, the front panel 511 includes a dialyzer mount with a pair of "keyhole" features 520 that are arranged to engage with a respective dialysate quick-connect fitting on the dialyzer 14. Each keyhole feature 520 includes an upper insertion area 520a sized to receive a portion of the quick-connect fitting and a lower flanged portion 520b that has a width that is smaller than an overall diameter of the quick-connect fitting and that engages with a grooved area of the quick-connect fitting. So as to aid in understanding of these features, FIG. 24 shows a dialyzer 14 with quick connect fittings 14a attached at dialysate inlet and outlet ports of the dialyzer 14. (Blood inlet and outlet ports are located at the extreme top and bottom of the dialyzer 14 shown in FIG. 24.) The quick connect fittings 14a shown are of a standard type, and most, if not all, dialyzers 14 have dialysate inlet/outlet ports that are arranged to engage with the standard quick connect fittings 14a. The quick connect fittings 14a each include a slide element 14b that is moved to the right (as shown in FIG. 24) relative to a base 14c to allow the fitting 14a to be engaged with a dialysate port on the dialyzer 14. When the slide element 14b is moved to allow the fitting 14a to be attached to the dialyzer 14, a groove 14d is closed. However, once the fitting 14a is properly seated on the inlet/outlet port of the dialyzer 14, the slide element 14b may be Is released, allowing a spring (not shown) to move the slide to the left as shown in FIG. 24, reestablishing the groove 14d to the condition shown in FIG. 24. Thus, when the quick connect fitting 14a is properly engaged with the dialyzer 14, the groove 14d will be present as shown in FIG. 24.

To mount the dialyzer 14 to the keyhole features 520, the quick connect fittings 14a may be partially inserted into the upper insertion area 520a of the top and bottom keyhole features, respectively, so that the groove 14d of each fitting 14a is aligned with a flange of the lower flanged portion 520b of the keyhole features 520. (Note that the upper insertion area 520 of the bottom keyhole feature 520 may be made longer than that shown in FIG. 23 to allow the accommodation of a wider range of dialyzer lengths.) With the grooves 14d aligned with the flanges, the dialyzer 14 may be lowered so that the quick connect fittings 14a are fully received into the lower flanged portions 520b of the keyhole features 520.

In accordance with another aspect of the invention, one or both of the keyhole features 520 may be adjustable so that the weight of the dialyzer 14 is shared by both lower flanged portions 520b of the keyhole features 520. For example, in this illustrative embodiment, the bottom keyhole feature 520 has part of the lower flanged portion 520b adjustable in vertical position relative to the top keyhole feature 520. In this way, the portion of the lower flanged portion 520b may be adjusted in vertical position so that, with the top quick connect fitting 14a supported by the flanged portion 520b of the top keyhole feature 520, the movable portion of the flanged portion 520b of the bottom keyhole feature can be moved, e.g., upwardly, so that the bottom quick connect fitting 14a is also supported by the flanged portion 520b. Thus, the weight of the dialyzer 14 can be shared by both keyhole features 520. The flanged portion 520b may be made adjustable in any suitable way. In this embodiment, the flanged portion 520b has a "U" shaped member 520c that is vertically slidable along the vertical flanges and can be fixed in place by tightening a set of thumb screws. The "U" shaped member 520c may engage the quick connect fitting 14a so that the "U" shaped member 520c supports the weight (at least in part) of the dialyzer 14.

Although in the embodiment above, the dialyzer 14 is supported by keyhole features in the front panel 511, a support arrangement for the dialyzer may be configured in other ways. For example, the upper insertion area 520a is not necessarily required. Instead, only flange portions (e.g., in the shape of a "U" shaped flange having opposed flange portions) may be provided to engage the dialyzer quick connect fittings. The flange portions may be offset from the front surface of the front panel 511 to provide clearance for the fitting and allow the flange portions to engage with the grooves of the quick connect fittings. Also, the flange portions need not be provided in a vertical orientation as shown, but instead may be oriented at an angle to the vertical, e.g., in a horizontal arrangement. The flange portions may have a detent, catch, or other feature to help maintain the dialyzer in place as well.

Figure 25:
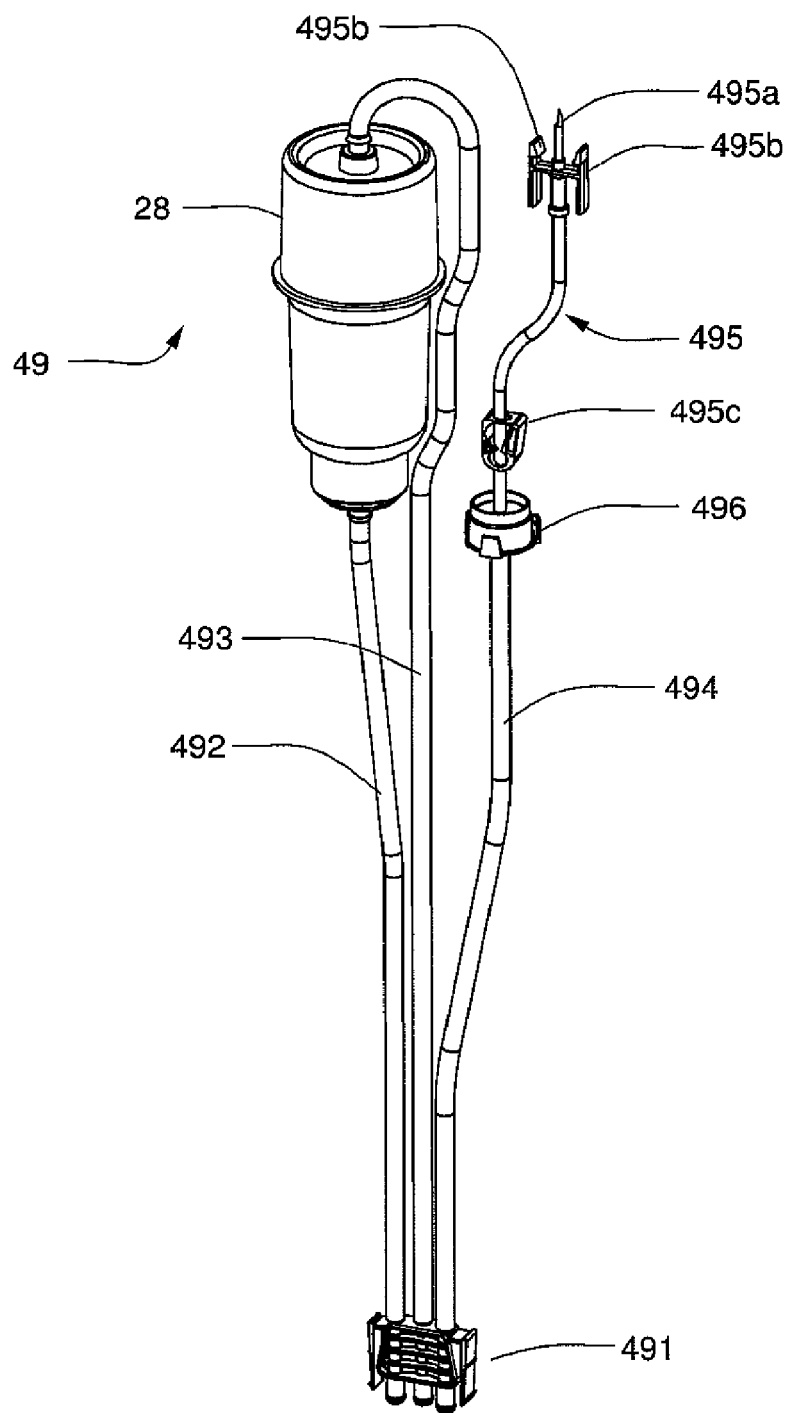
FIG. 25 shows a right perspective view of a reagent supply for use with the system of FIG. 7.

In accordance with another aspect of the invention, a bicarbonate, acid and/or other reagent supply device may be selectively associated with the dialysis unit. As described above, the dialysis unit 51 requires a supply of certain chemicals to generate dialysate and/or other materials needed for system operation. FIG. 25 shows a reagent supply 49 used to provide acid, bicarbonate and/or other materials to the dialysis unit 52. (FIG. 21 shows the reagent supply 49 attached to the acid/bicarbonate connection point 512 on the front panel 511.) The reagent supply 49 in this illustrative embodiment includes an E-prong connector 491 that is arranged to mate with the acid/bicarbonate connection point 512. As with other connections made by the user at the front panel 511, e.g., including the blood line connections at the connection point 514, the mating connectors may be color coded or otherwise marked to help ensure proper connections are made. For example, the E-prong connector 491 and the acid/bicarbonate connection point 512 may be colored orange, while the arterial line 203 and its mating connection at the connection point 514 may be colored red, and the venous line 204 and its mating connection at the connection point 514 are colored blue. Leading from the E-prong connector 491 are a bicarbonate supply line 492, a water supply line 493 and an acid supply line 494. (See FIG. 6 and the accompanying description regarding the function of these lines.) The water supply line 493 provides water to a bicarbonate supply 28 (which in this embodiment is a 750 g Altracart Bicarbonate cartridge (#500750A) sold by Baxter International Inc. that includes a powdered bicarbonate material, but may be any suitable supply), which provides bicarbonate to the dialysis unit 51 via the bicarbonate supply line 492. In this embodiment, the acid supply line 494 leads to an acid bag spike 495, which may be used to pierce and draw a suitable acid from a IV-type bag or other container. In this embodiment, the acid bag spike 495 includes a spike member 495a and a pair of spring clips 495b. The spring clips 495b are joined together at center portions by a connecting bar such that the spring clips 495b and the connecting bar form an "H" shape and allow the spring clips 495b to be pivoted relative to each other when proximal ends of the spring clips 495b are squeezed toward each other. The spring clips 495b may be arranged to engage with a connector element on an acid bag (or other acid supply, not shown) so that the spike member 495a remains engaged with the bag until a user disengages the clips 495b. For example, distal ends of the clips 495b may include barbs that engage with the acid supply, and the clips may be disengaged from the acid supply by squeezing proximal ends of the clips 495b together to disengage the barb elements at the distal ends of the clips 495b from the acid supply. The acid bag spike 495 may also include a valve 495c (in this case, a pinch clamp) to open/close the line of the acid bag spike 495. In accordance with one aspect of the invention, the acid bag spike 495 may be replaced (disconnected from the acid supply line 494 at a cap connector 496) with another component, such as an acid jug straw (not shown) or other arrangement. When used with a jug straw, the cap connector 496 may be engaged with an acid jug opening such that the cap connector 496 covers the opening, like a cap. Alternatively, the jug straw can terminate in a spike, which then has the ability to penetrate a self-sealing (e.g. rubber) membrane covering the opening of the acid jug. Thus, different types of components may be attached to the acid supply line 494 depending on the acid supply arrangement (such as a jug, bottle, bag, or other).

Figure 26:
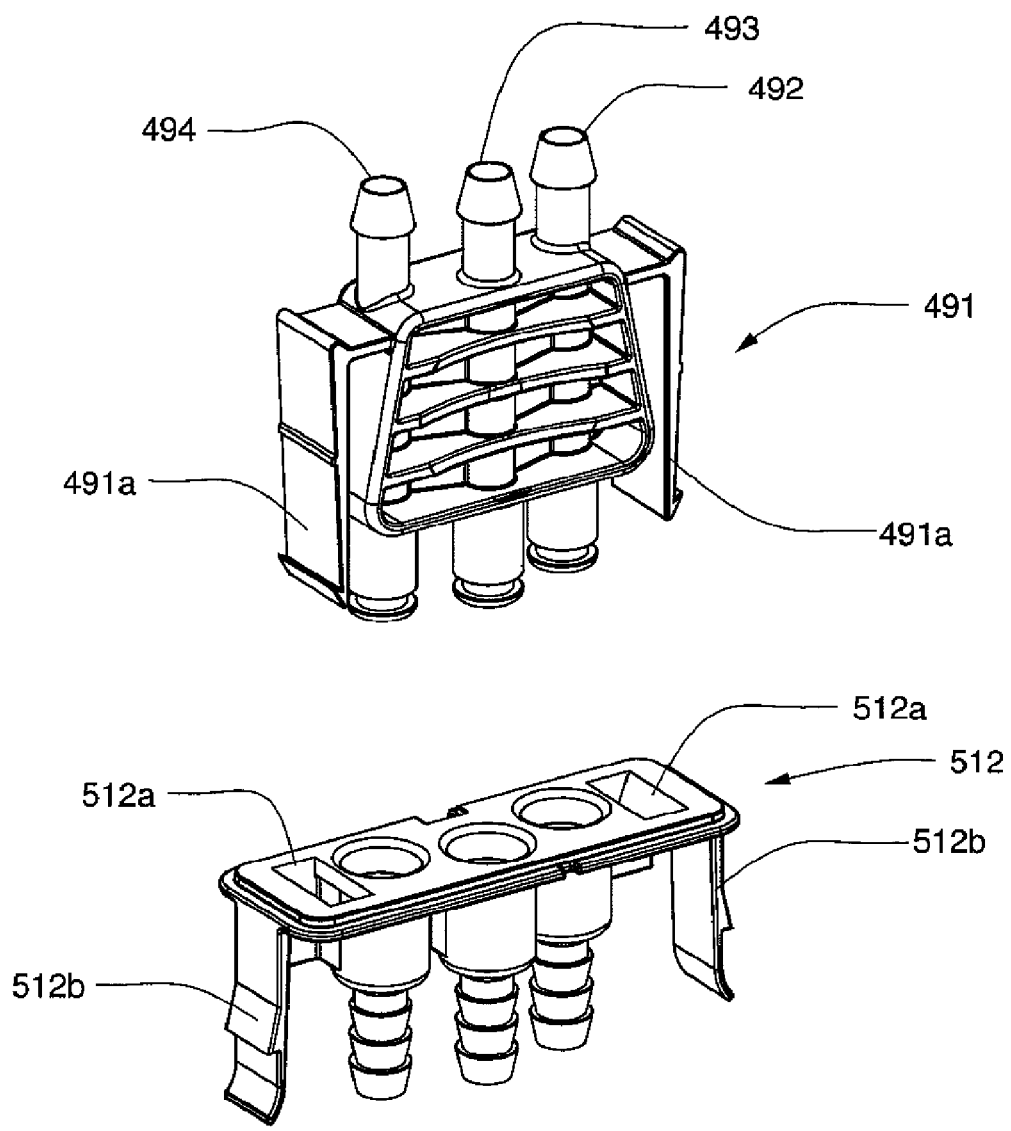
FIG. 26 shows a perspective view of an E-prong connector for the reagent supply of FIG. 25 and a corresponding connection point at the front panel of the hemodialysis system.

FIG. 26 shows a close up view of the E-prong connector 491 and the corresponding connection point 512 at the front panel 511. The E-prong connector 491 has three parallel prongs (corresponding to the bicarbonate and acid supply lines 492 and 494 and the water supply line 493) that that engage with corresponding receiving holes in the connection point 512. The E-prong connector 491 and receiving holes in the connection point 512 are arranged so that a center lumen (the water supply line 493) is arranged above, or otherwise out of, a common plane of the two outer lumens (the bicarbonate and acid supply lines 492 and 494). In this way, it is ensured that the bicarbonate and acid supply lines 492 and 494 are properly connected since the E-prong connector 491 cannot be engaged with the connection point 512 unless appropriately oriented. The E-prong connector 491 includes a pair of spring tabs 491a that can be engaged with corresponding slots 512a in the connection point 512, e.g., when the prongs are properly seated in receiving holes of the connection point 512. With the tabs 491a engaged in the slots 512a, the E-prong connector 491 cannot be easily removed from the connection point 512, helping reduce the likelihood of an accidental disconnection. The E-prong connector 491 may be disconnected by pressing the tabs 491a toward each other so that barbs at the distal ends of the tabs 491a disengage from the slots 512a. The connection point 512 has similar spring tabs 512b which allow the connection point 512 to be connected to and disconnected from the front panel 511.

In accordance with another aspect of the invention, a disinfect connector (not shown) engages with connection point 512 for use during a disinfection procedure. The disinfect connector has three parallel prongs having a similar orientation as the E-prong connector 491, so that the prongs may engage with the receiving holes in connection point 512. The channels in the prongs of the disinfect connector terminate within a common chamber within the disinfect connector. Thus, during a disinfect procedure, the bicarbonate flow line, acid flow line and water flow line are all interconnected, permitting disinfection of each of these flow lines during the disinfect procedure. (This is shown as a dashed inverted "T" line at 49 in FIG. 6).

Figure 27:
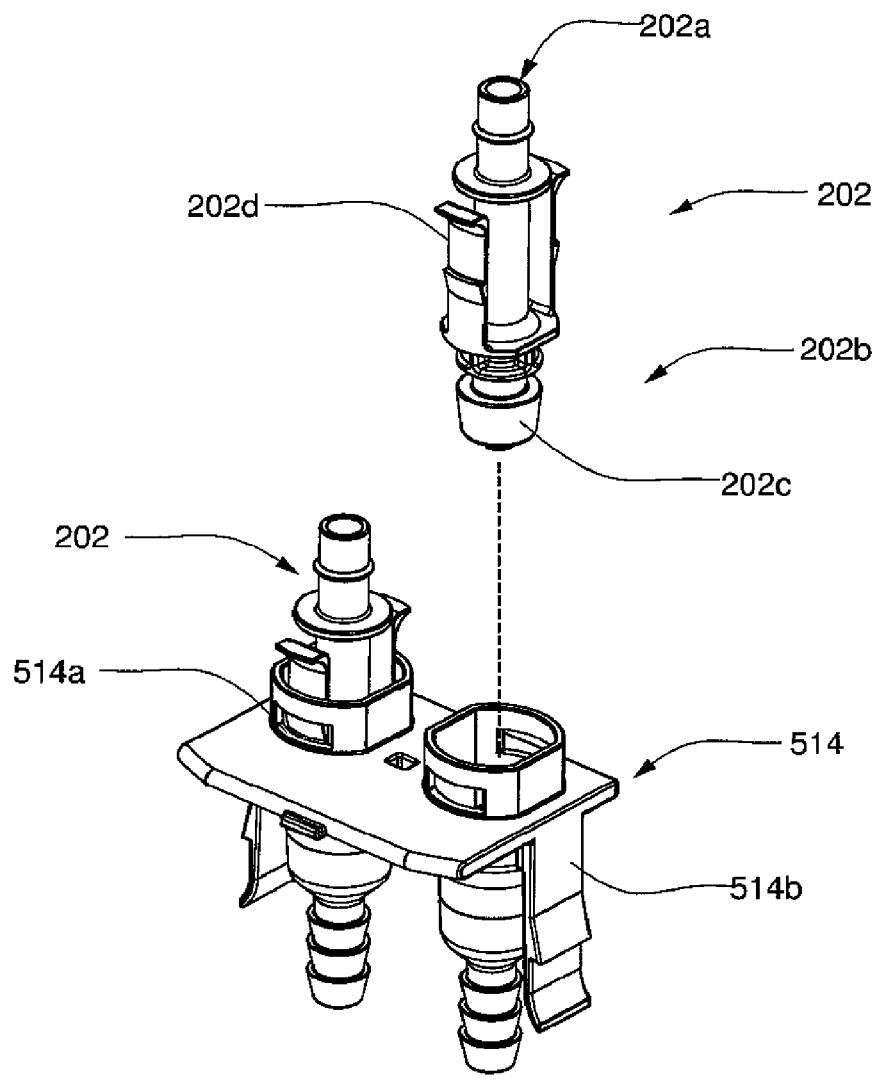
FIG. 27 shows a perspective view of a pair of blood line connectors for the blood circuit assembly and a corresponding connection point at the front panel of the hemodialysis system.
Figure 28:
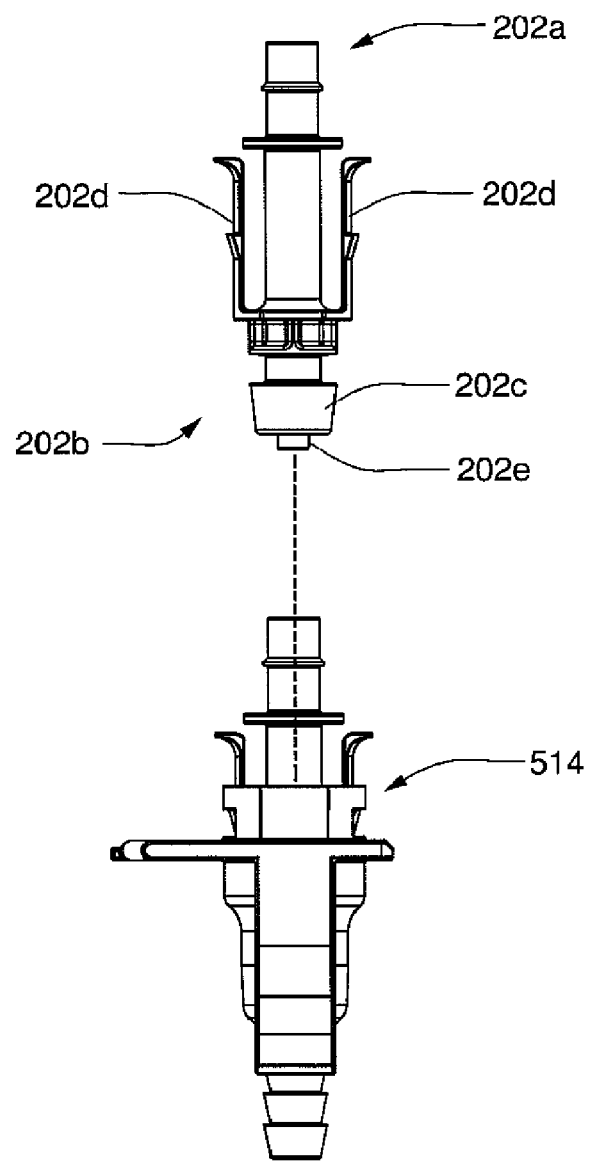
FIG. 28 shows a side view of a blood line connector and connection point of FIG. 27.

In accordance with another aspect of the invention, the blood lines 203, 204 are equipped with a connector that enables two types of connections to be made. One type of connection is a plug-in or press-in connection by which the connector can be pushed into a receiving lumen and a leakfree connection made without requiring rotation of the connector or the receiving lumen. A second type of connection is a screw-type connection by which a leakfree connection can be made by a threaded engagement of the connector with a complementary element. For example, FIGS. 27 and 28 show a perspective view and a side view of a blood line connector 202 that is used with the blood lines 203, 204 and that can engage with the blood line connection point 514 on the front panel 511. The connector 202 includes a tube connection end 202a that connects to the corresponding blood line 203, 204, and a patient access connection end 202b that is arranged to connect to both a patient access as well as the connection point 514 to establish a leakfree connection. At the patient access connection end 202b, the connector 202 includes a frustoconical member 202c that has an internally threaded portion arranged to engage with an externally threaded patient access. For example, the frustoconical member 202c may be part of a male-type luer connector that includes the central tube 202e extending from the center of the frustoconical member 202c. When making the luer connection, the tube 202e may extend into a female luer connector at the patient access and the threaded portion on the interior of the frustoconical member 202c may engage with a thread on the female luer connector of the patient access (whether arterial or venous). Such luer connections are standard when connecting blood lines to a patient access. However, the connector 202 may also be engaged with the connection point 514 by simply pushing the patient access connection end 202b into a receiving hole of the connection point 514. When making this connection, the exterior of the frustoconical member 202c may engage with a suitable seat, or other surface or element in the connection point 514 (such as a valve seat, O-ring, or other) so that a seal is formed between the frustoconical member 202c and the connection point 514. The central tube 202e may also, or instead, be used to engage with the connection point 514 to establish a suitable seal. Locking arms 202d that extend rearwardly from the frustoconical member 202c may engage with holes 514a in the connection point 514 (e.g., barbed portions on the arms 202d may engage with the holes 514a) to help maintain the connector 202 in the receiving hole of the connection point 514. The connector 202 may be released by pressing the arms 202d toward each other (e.g., by pressing on finger depression portions at the distal ends of the arms 202d), thereby disengaging the barbs from the holes 514a, and withdrawing the connector 202. Note that the connection point 514 may include spring tabs 514b to allow the connection point 514 to be selectively engaged/disengaged at the front panel 511. The connectors 202 may be made in any suitable way, such as by molding of plastic as a single unitary part.

The following are each incorporated herein by reference in their entireties: U.S. Provisional Patent Application Serial No. 60/903,582, filed Feb. 27, 2007, entitled "Hemodialysis System and Methods"; U.S. Provisional Patent Application Ser. No. 60/904,024, filed Feb. 27, 2007, entitled "Hemodialysis System and Methods"; U.S. patent application Ser. No. 11/787,213, filed Apr. 13, 2007 and published as U.S. Patent Application Publication No. 2008/0058697 on Mar. 6, 2008, entitled "Heat Exchange Systems, Devices and Methods"; U.S. patent application Ser. No. 11/787,212, filed Apr. 13, 2007 and published as U.S. Patent Application Publication No. 2008/0175719 on Jul. 24, 2008, entitled "Fluid Pumping Systems, Devices and Methods"; U.S. patent application Ser. No. 11/787,112, filed Apr. 13, 2007 and published as U.S. Patent Application Publication No. 2007/0253463 on Nov. 1, 2007, entitled "Thermal and Conductivity Sensing Systems, Devices and Methods"; U.S. patent application Ser. No. 11/871,680, filed Oct. 12, 2007 and published as U.S. Patent Application Publication No. 2008/0208103 on Aug. 28, 2008, entitled "Pumping Cassette"; U.S. patent application Ser. No. 11/871,712, filed Oct. 12, 2007, entitled "Pumping Cassette"; U.S. patent application Ser. No. 11/871,787, filed Oct. 12, 2007 and published as U.S. Patent Application Publication No. 2008/0253911 on Oct. 16, 2008, entitled "Pumping Cassette"; U.S. patent application Ser. No. 11/871,793, filed Oct. 12, 2007 and published as U.S. Patent Application Publication No. 2008/0253912 on Oct. 16, 2008, entitled "Pumping Cassette"; and U.S. patent application Ser. No. 11/871,803, filed Oct. 12, 2007 and published as U.S. Patent Application Publication No. 2008/0202591 on Aug. 28, 2008, entitled "Cassette System Integrated Apparatus." In addition, the following are incorporated by reference in their entireties: U.S. Pat. No. 4,808,161, issued Feb. 28, 1989, entitled "Pressure-Measurement Flow Control System"; U.S. Pat. No. 4,826,482, issued May 2, 1989, entitled "Enhanced Pressure Measurement Flow Control System"; U.S. Pat. No. 4,976,162, issued Dec. 11, 1990, entitled "Enhanced Pressure Measurement Flow Control System"; U.S. Pat. No. 5,088,515, issued Feb. 18, 1992, entitled "Valve System with Removable Fluid Interface"; and U.S. Pat. No. 5,350,357, issued Sept. 27, 1994, entitled "Peritoneal Dialysis Systems Employing a Liquid Distribution and Pumping Cassette that Emulates Gravity Flow." Also incorporated herein by reference are a U.S. patent application Ser. No. 12/038,474, filed Feb. 27, 2008 and published as U.S. Pat. Application Publication No. 2008/0253427 on Oct. 16, 2008, entitled "Sensor Apparatus Systems, Devices and Methods," and a U.S. patent application Ser. No. 12/038,648, filed Feb. 27, 2008 and published as U.S. Patent Application Publication No. 2008/0216898 on Sep. 11, 2008, entitled "Cassette System Integrated Apparatus".

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed.

The indefinite articles "a" and "an," as used herein in the specification and in the claims, unless clearly indicated to the contrary, should be understood to mean "at least one."

What is claimed is:

1. A reagent supply arrangement for a hemodialysis system, including:
    an E-prong connector, having three parallel prongs that are separate from each other, with two outer prongs extending lengthwise in a common plane and a center prong extending lengthwise outside of and above the common plane;
    a first supply line for a first reagent connected in fluid communication with one of the outer prongs; a second supply line for a second reagent connected in fluid communication with the other of the outer prongs;
    a liquid line connected in fluid communication with the center prong; and
    a container for housing the first reagent having an inlet connected to the liquid line and an outlet connected to the first supply line for the first reagent,
    wherein the three parallel prongs of the E-prong connector are arranged to allow connection of the prongs to corresponding receiving holes of a connection point of the hemodialysis system in only a single orientation of the E-prong connector and thus prevent improper connection of the prongs with the connection point.

2. The arrangement of claim 1, wherein the container includes a bicarbonate material suitable for use in generating a dialysate for the hemodialysis system.

3. The arrangement of claim 2, wherein the liquid line is a water supply line that provides water to the container.

4. The arrangement of claim 3, wherein the first supply line is a bicarbonate supply line that provides bicarbonate material and water to the E-prong connector.

5. The arrangement of claim 1, wherein the second supply line is an acid supply line that provides acid material to the E-prong connector.

6. The arrangement of claim 5, wherein the acid supply line includes a connector opposite the E-prong connector.

7. The arrangement of claim 6, further comprising an acid bag spike removably engaged with the connector of the acid supply line.

8. The arrangement of claim 7, wherein the acid bag spike includes a spike member and a pair of spring clips at an end of the acid bag spike opposite the connector of the acid supply line.

9. The arrangement of claim 8, wherein the spike member and the spring clips are molded as a single unitary piece.

10. The arrangement of claim 9, wherein the acid bag spike includes a pinch clamp to occlude flow in the acid bag spike.

11. The arrangement of claim 9, wherein the spike member and the spring clips are arranged to enable the spring clips to maintain engagement of the spike member with an acid supply.

12. The arrangement of claim 11, wherein the spring clips are manipulable to allow disengagement of the spring clips and the spike member from the acid supply.

13. The arrangement of claim 8, wherein the spring clips are joined together at center portions by a connecting bar such that the spring clips and the connecting bar form an "H" shape.

14. The arrangement of claim 13, wherein the spring clips include a barb member at a distal end.

* * * * *